United States Patent
Mehrpour et al.

(10) Patent No.: US 11,573,241 B2
(45) Date of Patent: Feb. 7, 2023

(54) TOTAL CELLULAR IRON AS A MARKER OF CANCER STEM CELLS AND USES THEREOF

(71) Applicants: Institut National de la Sante et de la Recherche Medicale (INSERM), Paris (FR); Centre National de la Recherche Scientifique (CNRS), Paris (FR); Universite Paris Descartes, Paris (FR)

(72) Inventors: Maryam Mehrpour, L'hay les Roses (FR); Raphael Rodriguez, Vers-Pont-du-Gard (FR); Ahmed Hamai, Villetaneuse (FR); Trang Mai, Ho Chi Minh Ville (VN)

(73) Assignees: Institute National de la Sante et de la Recherche Medicale (INSERM), Paris (FR); Centre National de la Recherche Scientifique (CNRS), Paris (FR); Université de Paris, Paris (FR)

( * ) Notice: Subject to any disclaimer, the term of this patent is extended or adjusted under 35 U.S.C. 154(b) by 54 days.

(21) Appl. No.: 16/082,970

(22) PCT Filed: Mar. 8, 2017

(86) PCT No.: PCT/EP2017/055450
§ 371 (c)(1),
(2) Date: Sep. 7, 2018

(87) PCT Pub. No.: WO2017/153475
PCT Pub. Date: Sep. 14, 2017

(65) Prior Publication Data
US 2019/0101549 A1   Apr. 4, 2019

(30) Foreign Application Priority Data
Mar. 9, 2016 (EP) .................................. 16305266

(51) Int. Cl.
*G01N 33/84* (2006.01)
*G01N 33/574* (2006.01)
*A61K 31/7048* (2006.01)

(52) U.S. Cl.
CPC ......... *G01N 33/84* (2013.01); *A61K 31/7048* (2013.01); *G01N 33/57415* (2013.01); *G01N 33/57496* (2013.01); *G01N 2800/52* (2013.01)

(58) Field of Classification Search
USPC ....................................................... 436/84
See application file for complete search history.

(56) References Cited

U.S. PATENT DOCUMENTS

| 2005/0214219 A1 | 9/2005 | Green et al. |
| 2013/0012409 A1 | 1/2013 | Frank et al. |
| 2013/0203800 A1 | 8/2013 | Cabantchik et al. |

FOREIGN PATENT DOCUMENTS

WO   WO 2015/198334 A2   12/2015

OTHER PUBLICATIONS

Huang, A. et al. Breast cancer stem cell selectivity of synthetic nanomolar-active salinomycin analogs, BMC Cancer, 16(145), 1-12 (Year: 2016).*
Andersen et al., *Cancer treatment: the combination of vaccination with other therapies*, 57(11) Cancer Immunol Immunother 1735-1743 (Nov. 2008).

(Continued)

*Primary Examiner* — Xiaoyun R Xu
(74) *Attorney, Agent, or Firm* — Panitch Schwarze Belisario & Nadel LLP; Erin M. Dunston

(57) ABSTRACT

The present invention relates to a novel use of total cellular iron, preferably under the form of ferrous iron ($Fe^{2+}$), as a marker of cancer stem cells (CSCs). The invention also relates to methods using said iron marker, in particular for (Continued)

Figure 1A:
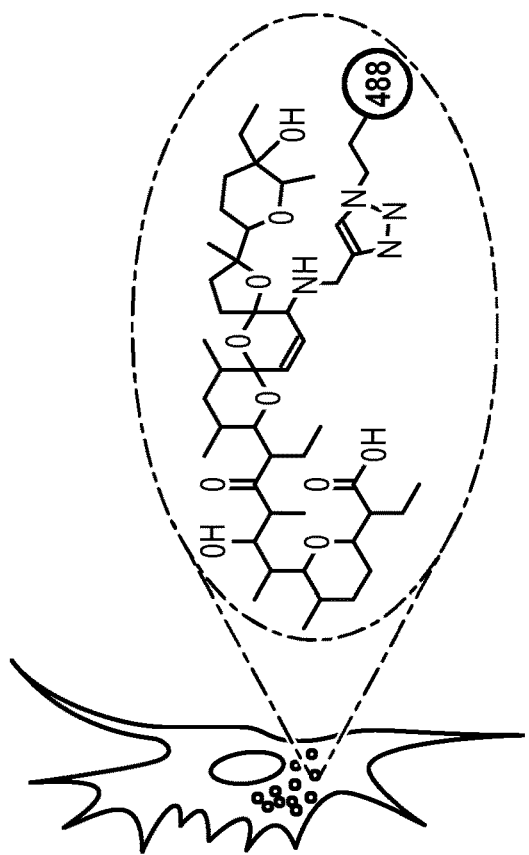
Figure 1A:
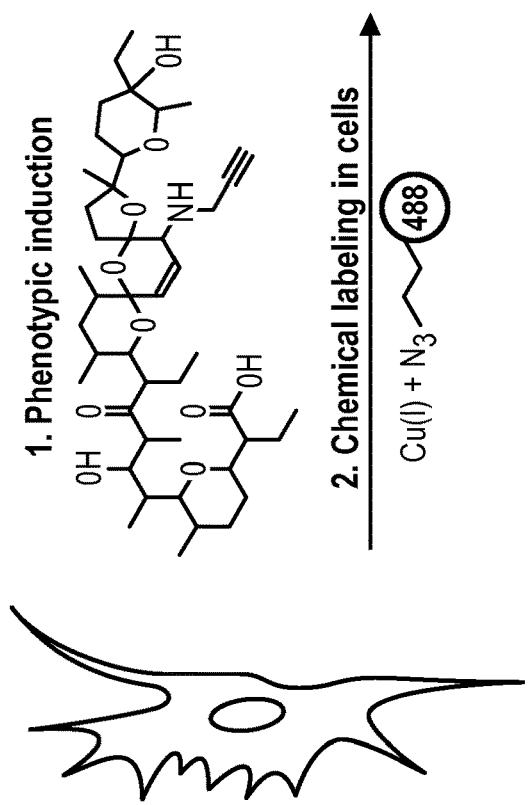

metastatic cancer diagnosis or treatment, for screening for compounds of interest, as well as for killing CSCs.

8 Claims, 45 Drawing Sheets

(56) References Cited

OTHER PUBLICATIONS

Baskar et al., *Cancer and Radiation Therapy: Current Advances and Future Directions*, 9(3) International Journal of Medical Sciences 193-199 (2012).
Brown et al., *Identification of Small Molecule Inhibitors that Distinguish between Non-Transferrin Bound Iron Uptake and Transferrin-Mediated Iron Transport*, 11(3) Chemistry & Biology 407-416 (Mar. 2004).
Charafe-Jauffret et al., *ALDH1-Positive Cancer Stem Cells Predict Engraftment of Primary Breast Tumors and Are Governed by a Common Stem Cell Program*, 73(24) Cancer Research 7290-7300 (Dec. 15, 2013).
Déry et al., *Automated Morphometric Analysis of Mammospheres: Characterization of Breast Cancer Drugs*, AACR Annual Meeting, Nexcelom Bioscience (2010).
Eberhard et al., *Chelation of intracellular iron with the antifungal agent ciclopirox olamine induces cell death in leukemia and myeloma cells*, 114(14) Blood 3064-3073 (Oct. 1, 2009).
González-Bártulos et al., *Pro-Oxidant Activity of Amine-Pyridine-Based Iron Complexes Efficiently Kills Cancer and Cancer Stem-Like Cells*, 10(9) PLOS ONE 1-25 (Sep. 14, 2015).
Gupta et al., *Identification of Selective Inhibitors of Cancer Stem Cells by High-Throughput Screening*, 138(4) Cell 645-659 (Aug. 21, 2009).
Gusterson et al., *Basal cytokeratins and their relationship to the cellular origin and functional classification of breast cancer*, 7(4) Breast Cancer Research 143-148 (Jul. 2005).
Hamai et al., *Autophagy and cancer stem cells or tumor-initiating cells in human breast cancer*, Frontiers in Pharmacology Conference Abstract: 4$^{th}$ Annual Meeting of the International Society of Proton Dynamics in Cancer (abstract only).
Hirooka et al., *A Combination Therapy of Gemcitabine with Immunotherapy for Patient with Inoperable Locally Advanced Pancreatic Cancer*, 38(3) Pancreas e69-e74 (Apr. 2009).
Horan et al., *Fluorescent Cell Labeling for in Vivo and in Vitro Cell Tracking*, 33 Methods in Cell Biology 469-490 (1990).
Lis et al., *Mesenchymal Cell Interaction with Ovarian Cancer Cells Triggers Pro-Metastatic Properties*, 7(5) PLOS ONE 1-10 (May 2012).
Liseth et al., *Combination of Intensive Chemotherapy and Anticancer Vaccines in the Treatment of Human Malignancies: The Hematological Experience*, 10 Journal of Biomedicine and Biotechnology 1-15 (2010).
Manz et al., *Iron and cancer: recent insights*, 1368(1) Annals of the New York Academy of Sciences 149-161 (2016).
Miller et al., *An Iron Regulatory Gene Signature Predicts Outcome in Breast Cancer*, 71(21) Cancer Research 6728-6737 (Nov. 1, 2011).
Naujokat et al., *Salinomycin as a Drug for Targeting Human Cancer Stem Cells*, 2012 Journal of Biomedicine and Biotechnology 1-17 (2012).
Perou et al., *Molecular portraits of human breast tumours*, 406 Nature 747-752 (Aug. 2000).
Quoix et al., *Therapeutic vaccination with TG4010 and first-line chemotherapy in advanced non-small-cell lung cancer: a controlled phase 2B trial*, 12(12) The Lancet Oncology 1125-1133 (Nov. 2011).
Schonberg et al., *Preferential Iron Trafficking Characterizes Glioblastoma Stem-Like Cells*, 28 Cancer Cell 441-455 (Oct. 12, 2015).
Shterman et al., *Comparison of Transferrin Receptors, Iron Content and Isoferritin Profile in Normal and Malignant Human Breast Cell Lines*, 59 Pathobiology 19-25 (1991).
Yue et al., *Inhibition of the autophagic flux by salinomycin in breast cancer stem-like/progenitor cells interferes with their maintenance*, 9(5) Autophagy 714-729 (May 2013).
Zhang et al., *Salinomycin Inhibits the growth of colorectal carcinoma by targeting tumor stem cells*, 34 Oncology Reports 2469-2476 (2015).

\* cited by examiner

Control samples        Samples containing $FeCl_2$

Rhonox-1        Rhonox-1 Fluorescence

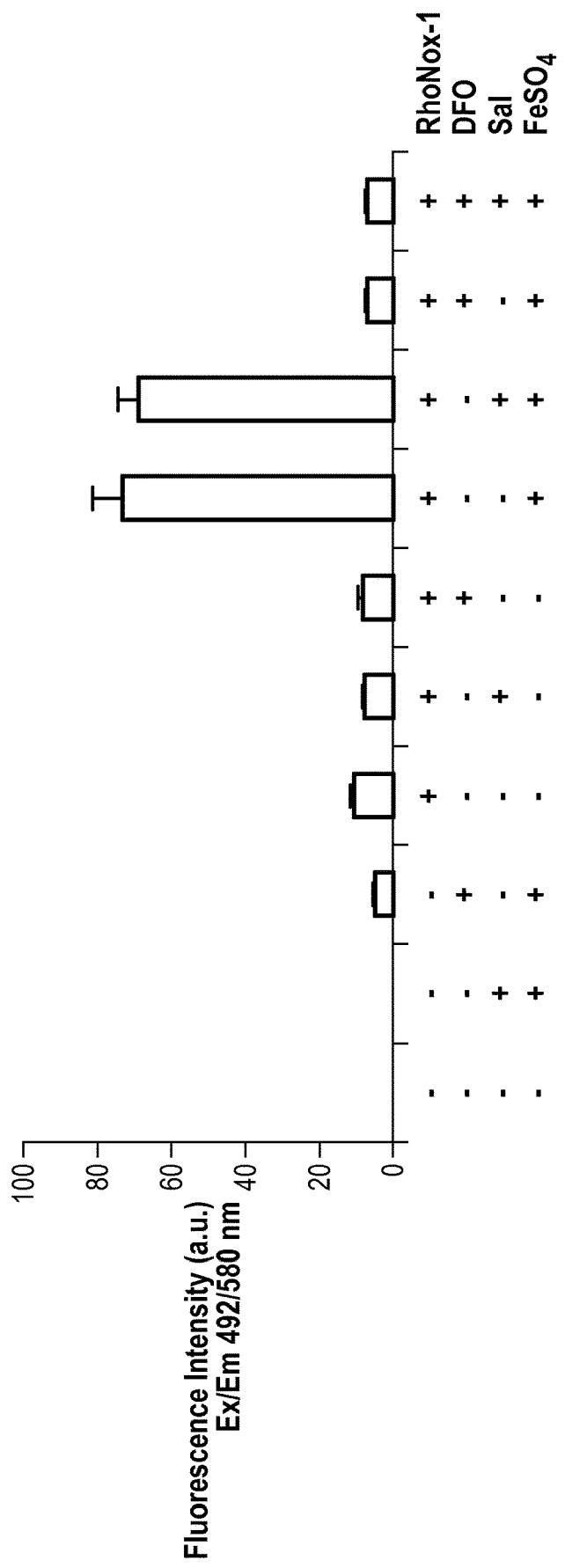

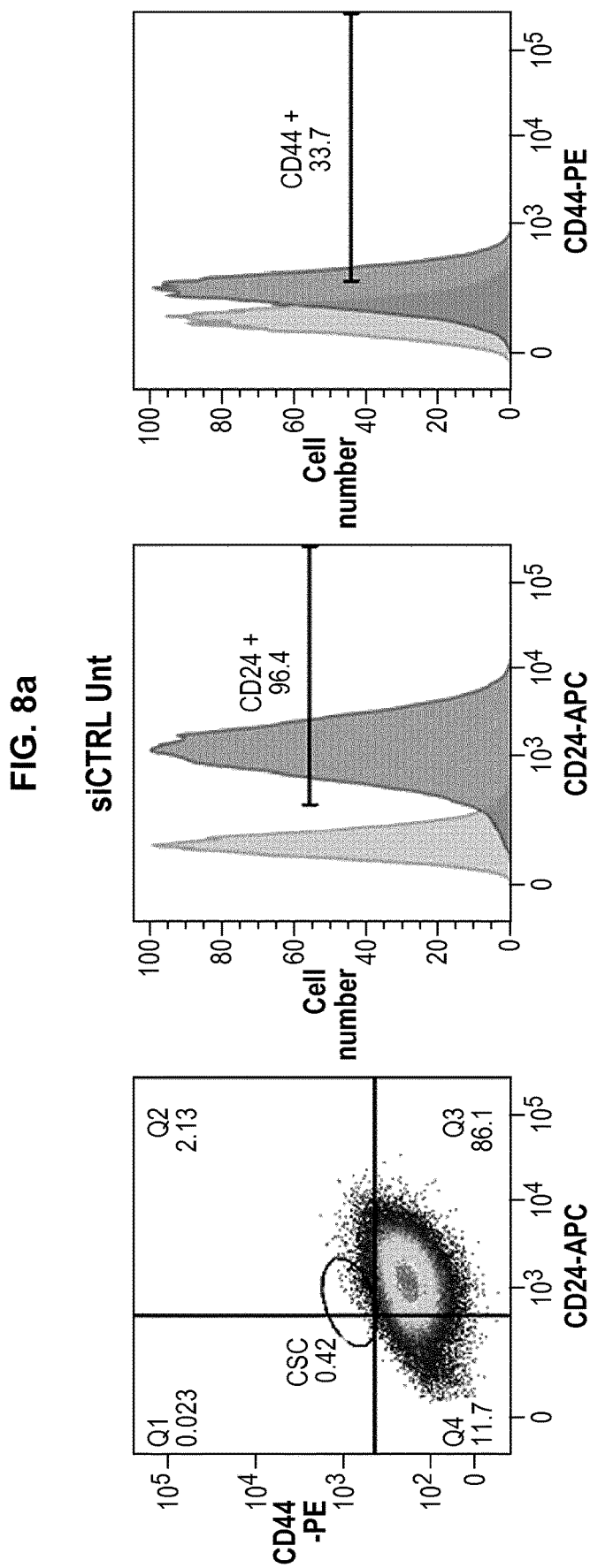

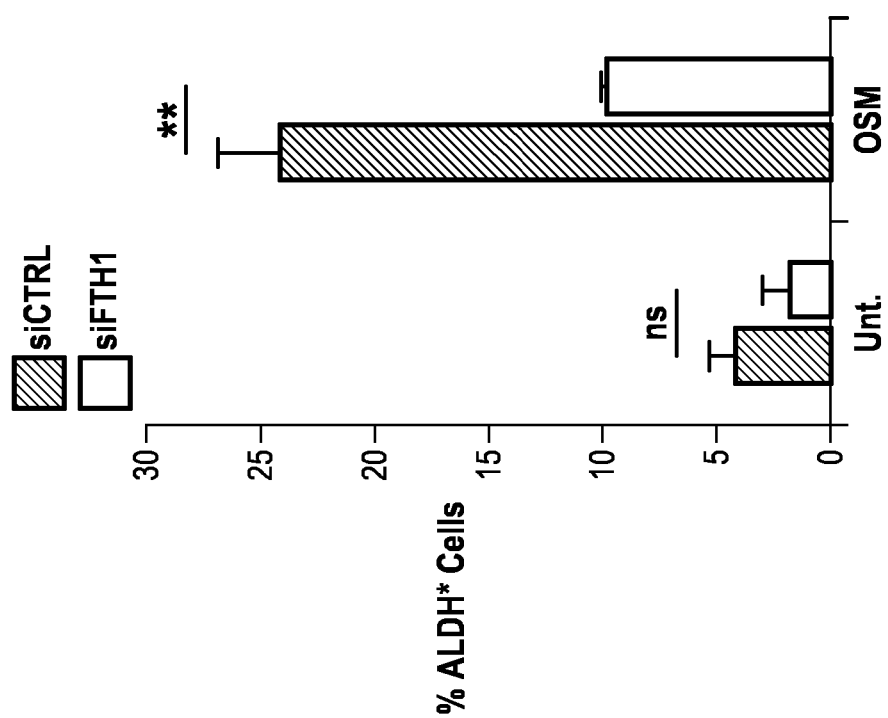

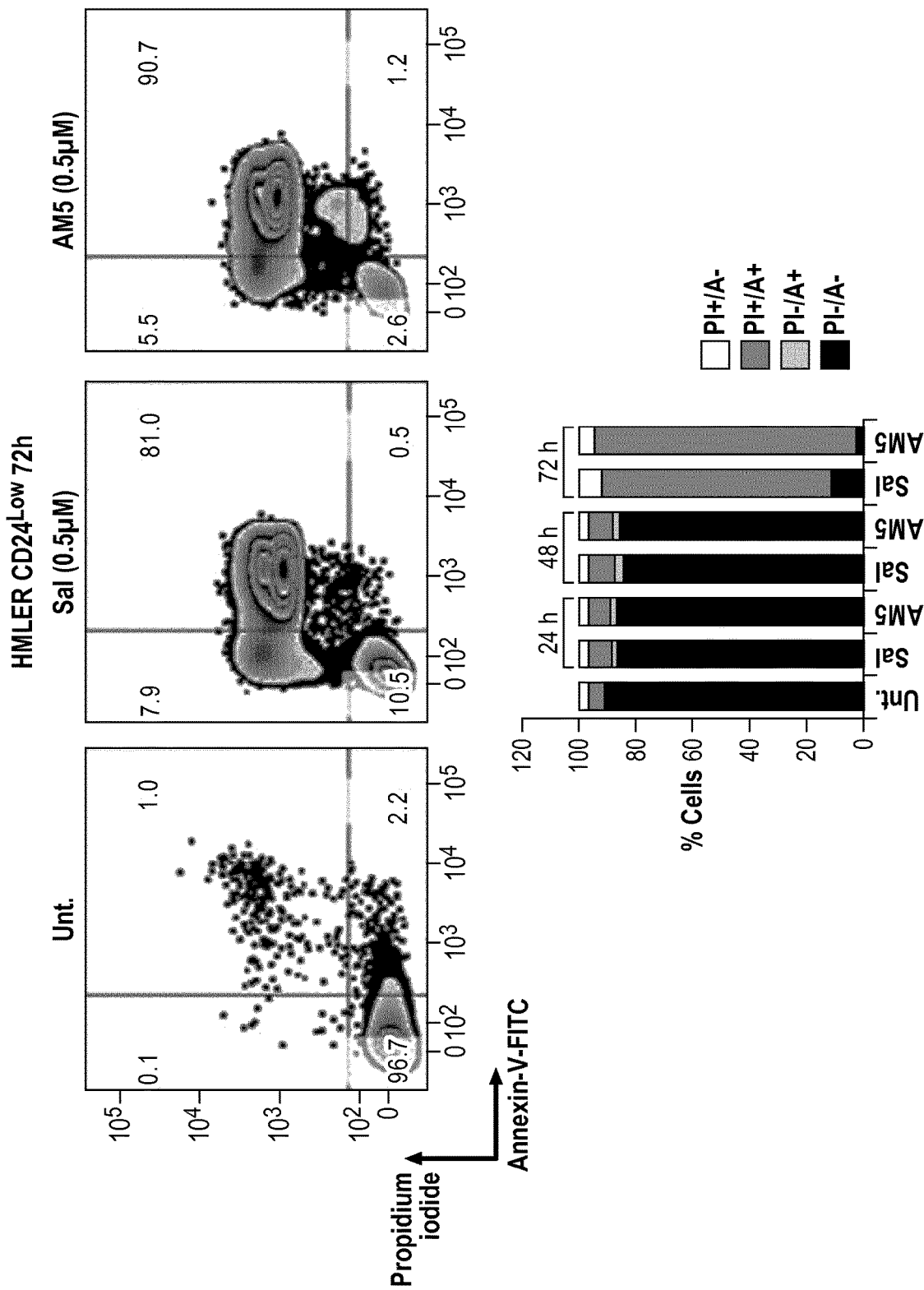

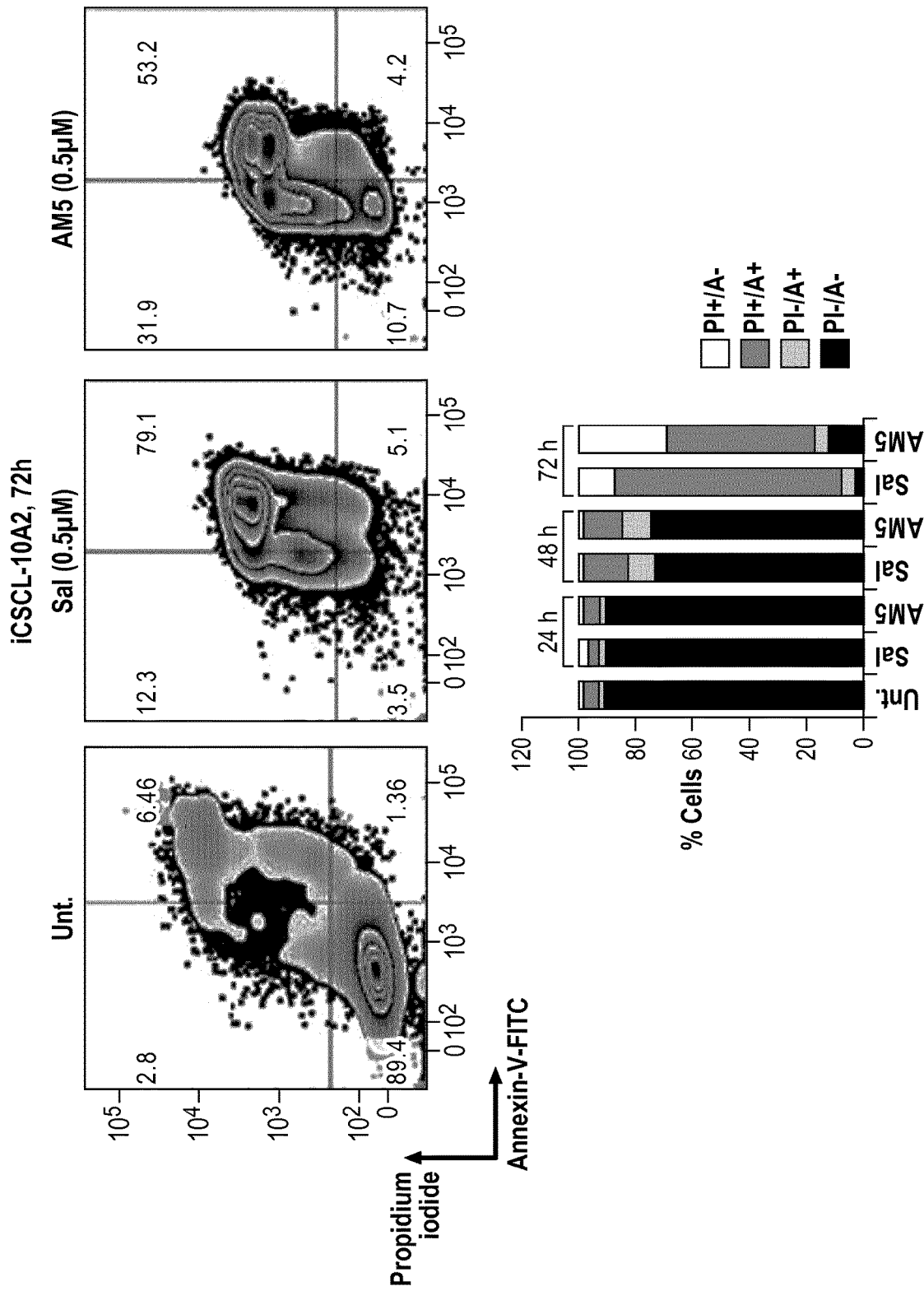

A - Unt.
B - Doc (10mg/kg/week)
C - Sal (3mg/kg/day)
D - AM5 (1mg/kg/week)
E - Doc (10mg/kg/week) + Sal (0.6mg/kg/day)
F - Doc (10mg/kg/week) + AM5 (0.2mg/kg/day)

TOTAL CELLULAR IRON AS A MARKER OF CANCER STEM CELLS AND USES THEREOF

CROSS-REFERENCE TO RELATED APPLICATIONS

This application is a U.S. National Stage Application pursuant to 35 U.S.C. § 371 of International Patent Application PCT/EP2017/055450, filed on Mar. 8, 2017, and published as WO 2017/153475 on Sep. 14, 2017, which claims priority to European Patent Application 16305266.5, filed on Mar. 9, 2016, all of which are incorporated herein by reference in their entireties for all purposes.

BACKGROUND OF THE INVENTION

Increasing evidence suggests that initial cancer development is due to a rare population of cells, termed Cancer Stem Cells (CSCs) (also known as "tumor-initiating cells" (TICs) or "tumor side-populations" or "cancer stem-like cells") that are able to initiate and sustain this disease. These cells have indeed been demonstrated to be responsible for tumorigenesis, cancer metastasis, and cancer reoccurrence in particular cancers. CSCs have self-renewal capacity and they can differentiate into multiple cell types, although the equilibrium between self-renewal and differentiation potential shifts towards enhanced self-renewal, leading to limited differentiation capacity.

It is well known by one skilled in the art that cancer is among the most important and most difficult diseases of the $21^{st}$ century to treat. Conventional anticancer therapies include surgery, immunotherapy and radiotherapy, as well many forms of drug treatments such as tamoxifen.

Currently available chemotherapies and radiotherapies are known to kill differentiated or differentiating cells, which form the bulk of the tumor (but that are unable to regenerate tumors). However, the population of CSCs remains unaffected by said treatments and often causes a relapse of the disease.

Given the variety of therapies to which they are resistant, it is possible that CSCs would exhibit a resistance to apoptosis, suggesting that it might not be possible in practice to find therapies that specifically target CSCs.

Classical anticancer therapy is able to kill actively dividing cancerous cells but cannot kill CSCs. Exposure to drugs or radiation causes some mutations in surviving CSCs which produce in turn secondary tumors with more resistance towards conventional anticancer therapy. Until now, unique pattern of surface proteins as well as cellular activity have been used as a marker for various forms of CSCs.

In this context, it is imperative that anti-cancer therapies include strategies affecting at least CSCs. As a matter of fact, by targeting CSCs, it will be possible to treat patients with aggressive and non-resectable tumors, as well as preventing tumor metastasis and recurrence.

Moreover, the identification of molecules that target CSCs in a selective manner, i.e., while sparing non-cancerous or normal stem cells, is critical to provide new anti-cancer drugs having few side effects.

It is therefore important to identify and validate pathways that are selectively implicated in CSC self-renewal and survival. Yet, though multiple pathways underlying properties of embryonic or adult stem cells have been already elucidated, few pathways have been identified for CSC self-renewal and survival.

Recent discoveries regarding the nature of stem cell niche, and the key pathways involved in stem cell-renewal, have provided information that would encourage finding a means for selectively targeting CSCs. Iron and cancer are suggested to form a complex partnership in the maintenance of cancer cells.

Thus, CSCs remain an important issue in cancer therapy.

There is a need in the art for a new therapeutic strategy, in particular for anticancer therapy that would more particularly target CSCs.

In this respect, markers are not just the identity of CSCs but are functionally important in maintaining CSCs as well as cancer. CSC markers can be targeted to inhibit the cancer growth.

However, CSC markers are diverse in nature. The current lack of universal markers appears to be the major obstacle in the treatment of cancer.

The inventors showed that, surprisingly, the amount of iron used by CSC cells is higher and suggests an important role of iron in the maintenance, proliferation and survival of CSCs.

The inventors proposed to alter iron availability in CSCs by targeting iron, more particularly iron II, which is shown here for the first time to be the point of fragility of CSCs.

According to their results, impairing the $Fe^{2+}/Fe^{3+}$ balance alters CSC survival and self-renewal. Targeting Iron II/III thus opens a new therapeutic strategy, and the monitoring of the progress and the response to such a treatment. Thus, they provide visual evidence that a synthetic derivative of salinomycin (Sal) exhibits a more potent and selective activity against breast CSCs.

The invention thus relies on a new therapeutic strategy that specifically targets CSCs.

The invention relies on a method to kill CSCs.

SUMMARY OF THE INVENTION

An aspect of the present invention is the use of total cellular iron, preferably under the form of ferrous iron ($Fe^{2+}$), as a marker of CSCs in a mammal.

Another aspect of the present invention is an in vitro method for detecting CSCs in a subject, comprising at least:

a) Measuring the amount of total cellular iron in a biological sample from said subject; and b) Comparing said amount measured in step a) to a reference value range for total cellular iron.

Another aspect of the invention is the use of a combination of markers comprising total cellular iron and one or more biomarkers selected from IRP2, ferritin, Wnt1, TfR, ALDH, IRGS, and Cathepsin B to detect CSCs.

Another aspect of the invention is the use of total cellular iron, in particular of body ferrous ($Fe^{2+}$) and ferric ($Fe^{3+}$) iron balance, as a lever of CSC death in a mammal, wherein said CSC death is preferably mediated by Reactive Oxygen Species (ROS) production.

Still another aspect of the invention is an in vitro method for diagnosing cancer in a subject, comprising at least:

a) Measuring the amount of total cellular iron, preferably under the form of ferrous iron ($Fe^{2+}$), in a biological sample from a subject; and b) Comparing said amount measured in step a) to a reference value range for total cellular iron, wherein an amount of total cellular iron as measured in step a) higher than said reference value range is indicative of the presence of CSCs, thereby indicating that said subject has a cancer.

According to a preferred embodiment, said in vitro method is for diagnosing cancer having a high risk of recurrence, a high risk of metastasis and/or a cancer with resistance to therapy, in a subject.

Another aspect of the invention relates to a method for selectively killing CSCs in a mammal, comprising: administering to said mammal having CSCs a therapeutically-effective amount of an iron-chelating composition, wherein said composition binds total cellular iron under the form of ferrous ($Fe^{2+}$) and ferric ($Fe^{3+}$) iron in said mammal, thereby inducing ferritinophagy and ROS production responsible for specific/selective CSC death in said mammal, while optionally preventing drug-resistance in said mammal by selectively targeting CSCs.

Another aspect of the invention relates to an iron-chelating pharmaceutical composition for use in a method for selectively killing CSCs.

Said iron-chelating pharmaceutical composition or composition for use in the method for selectively killing CSCs in a mammal preferably comprises at least one component selected from: salinomycin, analogs of salinomycin, more preferably AM5, AM23, or AM23S, autophagy inhibitors and combinations thereof.

Another aspect of the invention relates to an in vitro method for determining the prognosis of a subject diagnosed with cancer, comprising:

a) Measuring the amount of total cellular iron in a biological sample from said subject after the subject has been treated with an appropriate antitumoral agent and/or an iron-chelating pharmaceutical composition, b) Comparing said amount measured in step a) to a reference value range for total cellular iron.

According to a preferred embodiment, said in vitro method is for determining the prognosis of a subject diagnosed with cancer having a high risk of recurrence, a high risk of metastasis and/or a cancer with resistance to therapy.

Another aspect of the invention relates to an in vitro method for monitoring the efficacy of an antitumoral therapy in a subject undergoing said therapy, comprising at least:

a) Measuring the amount of total cellular iron in a biological sample from said subject at a time T1 before or during or after the subject has been administered said antitumoral therapy comprising an appropriate antitumoral agent and/or an iron-chelating pharmaceutical composition;

b) Measuring the amount of total cellular iron in a biological sample from said subject at a time T2 before or during or after the subject has been administered said antitumoral therapy comprising an appropriate antitumoral agent and/or an iron-chelating pharmaceutical composition, wherein said time T2 is posterior to said time T1;

c) Comparing said amount measured in step a) to said amount measured in step b) above, wherein an amount of total cellular iron as measured in step b) identical or higher than said amount measured in step a) is indicative that the subject is not responsive to said therapy, and wherein an amount of total cellular iron as measured in step b) less than said amount measured in step a) is indicative that the subject is responsive to said therapy.

Another aspect of the invention relates to an in vitro method for determining the antitumoral effect of a candidate agent in a subject, comprising at least:

a) Measuring the amount of total cellular iron in a biological sample from said subject before the subject is treated with said agent;

b) Comparing said amount measured in step a) to a reference value range for total cellular iron, thereby obtaining a first value;

c) Measuring the amount of total cellular iron in a biological sample from said subject after the subject has been treated with said agent;

d) Comparing said amount measured in step c) to said reference value range for total cellular iron, thereby obtaining a second value.

DETAILED DESCRIPTION OF THE INVENTION

Surprisingly, the present invention shows that a reliable diagnosis and decrease of the risk of relapse is allowed by using iron as a metal marker of CSCs. Using iron as such a marker allowed the inventors to identify new therapeutic strategies.

Iron as Marker of CSCs

In CSCs, the TfR is overexpressed. They will therefore have a higher concentration of iron in the form of $Fe^{3+}$ in the cell and of $Fe^{2+}$ in the lysosome. This higher amount of iron is used by the cells, which raises and suggests the important role of iron in the maintenance, proliferation and survival of CSCs.

Surprisingly, the inventors found a new marker of CSCs which is independent from mutations and which may be characterized according to the type of tumors.

An aspect of the invention concerns the use of total cellular iron as a marker of CSCs in a mammal.

As used herein, the term "Cancer Stem Cell" (CSC) refers to a cell that can be a progenitor of a highly proliferative cancer cell. A CSC has the ability to re-grow a tumor as demonstrated by its ability to form tumors in immunocompromised mice. CSCs are also typically slow-growing relative to the bulk of a tumor, i.e., CSCs are generally quiescent. The CSCs may represent only a portion, such as approximately 0.1 to 10% of a tumor. CSCs may have one or more or all of the following characteristics or properties: (i) they can harbor the ability to initiate a tumor and/or to perpetuate tumor growth, (ii) they can be generally relatively less mutated than the bulk of a tumor (e.g. due to slower growth and thus fewer DNA replication-dependent errors, improved DNA repair, and/or epigenetic/non-mutagenic changes contributing to their malignancy), (iii) they can have many features of normal stem cells (e.g., similar cell surface antigen and/or intracellular expression profile, self-renewal programs, multi-drug resistance, an immature phenotype, etc., characteristic of normal stem cells) and may be derived from normal stem cells, (iv) they can be the source of metastases, (v) they can be slow-growing or quiescent, (vi) they can be tumorigenic (e.g. as determined by NOD/SCID implantation experiments), (vii) they can be relatively resistant to traditional therapies (i.e. chemoresistant), and (viii) they can comprise a subpopulation of a tumor (e.g. relative to the tumor bulk).

By "total cellular iron", it is meant herein the total amount of iron in the cells of a mammal regardless of a particular iron form, thus encompassing $Fe^{2+}$, $Fe^{3+}$ and ferritin. "Total cellular iron" thus refers to the total amount of iron within a cell or a tumor.

As used herein, the term "marker" refers to the interesting property of total cellular iron to specifically "track" CSCs. Preferably, the marker is iron $Fe^{2+}$, which is highly concentrated in breast CSCs, as compared to the normal breast cells.

As used herein, the term "mammal" refers to animals and human beings.

A preferred embodiment of the present invention concerns the use of total cellular iron as a marker of CSCs, in a mammal wherein said mammal is a human being.

According to various embodiments, total cellular iron is useful as a marker for:

1—Diagnosing cancer in a subject.
2—Determining the prognosis of a subject diagnosed with cancer.
3—Monitoring the efficacy of an antitumoral therapy in a subject.

The term "diagnosis", as used herein, means detection of a pathological state or condition. With respect to the objects of the present invention, the diagnosis aims at confirming or not the presence of CSCs, preferably of breast CSCs, via measuring iron level. The term "confirming the presence or not" can be interpreted by "detecting" the presence of CSCs.

The term "prognosis", as used herein, refers to the prediction of the likelihood of CSCs attributable death or progression of cancer, including recurrence following tumor resection, metastatic spread, and drug resistance. With respect to the objects of the present invention, the "prognosis" thus means prediction of the survival rate of patients harboring CSCs, and preferably prognosis of cancer patients who have undergone breast tumor resection or after chemotherapy or after radiotherapy.

With respect to the objects of the present invention, the "prognosis" thus means prediction of the outcome of patients harboring breast CSCs, and preferably prognosis of breast cancer patients for:

i) Progression-free survival—the length of time during and after medication or treatment during which the cancer being treated does not get worse,
ii) Survival rate—indicating the percentage of people in a study or treatment group who are alive for a given period of time after diagnosis, and
iii) Survival time—the remaining duration of life. If not otherwise specified, it generally starts from the time of diagnosis.

The term "treatments" or "therapy" refers not only to the alleviation or amelioration of symptoms associated with cancer, but also the prevention or delay of the onset or recurrence of the disease, and/or lessening the severity or frequency of symptoms and metastatic spread of cancer.

By "antitumoral therapy" it is meant a treatment by a compound or a combination of compounds or compositions to a subject in order to prevent or eliminate a tumoral disease, including decreasing effect on the size of a tumor or the number of tumors in a subject, and/or to arrest or slow disease progress in a subject, and/or to inhibit or slow the development of a new pathological condition, and/or to decrease the frequency or severity of symptoms and/or recurrences in a subject who has currently or has previously had a disease, and/or to prolong or increase or expand the lifespan of the subject. In particular, the term "treatment of a disease" includes curing, shortening the duration, ameliorating, alleviating, preventing, slowing down or inhibiting or decreasing or preventing or delaying the onset of the disease or the symptoms thereof.

In a particular embodiment, the total cellular iron is used under the form of ferrous iron ($Fe^{2+}$) which is required for many biological processes and in particular for the epigenetic regulation of gene expression.

In a preferred embodiment, said subject is a mammal as defined herein, it is preferably a human being.

According to another aspect, the present invention relates to an in vitro method for detecting CSCs of a subject, comprises at least:

a) Measuring the amount of total cellular iron in a biological sample from said subject; and
b) Comparing said amount measured in step a) to a reference value range for total cellular iron.

Preferably, the total cellular iron as measured is step a) is under the form $Fe^{2+}$ and/or $Fe^{3+}$.

Preferably, the in vitro method for detecting CSCs in a subject, comprises at least:

a) Measuring the amount of total cellular iron in a biological sample from said subject; and
b) Comparing said amount measured in step a) to a reference value range for total cellular iron, wherein if said amount is higher than said range, thereby indicating a poor prognosis,
and if said amount is in said range, thereby indicating a good prognosis.

Preferably, the total cellular iron is under the form $Fe^{2+}$ and/or $Fe^{3+}$.

According to another aspect, the present invention relates to an in vitro method for detecting CSCs in a tumor of a subject, comprising at least:

a) Measuring the amount of total cellular iron in a biological sample from said tumor of a subject; and
b) Comparing said amount measured in step a) to a reference value range for total cellular iron.

By "reference value range" or "data of reference", it is meant herein appropriate data that are obtained from control subjects who are healthy and/or diseased subjects, and that are used for qualitatively and/or quantitatively comparing to the data obtained from the subject under consideration. In particular, by "reference value range" or "data of reference," it is meant herein the level of total iron as determined in said control subjects. The reference value may vary according to other parameters. For example, in a diseased subject, the overall reference value range is from about 0 pg per cell to about 0.30 pg per cell, preferably from about 0 pg/cell to about 0.08 pg/cell. In CSCs, the amount of iron is at least 4 times higher than in cancer cells, preferably at least 7 times higher than in cancer cells.

As an example, the value range of 0 to 0.04 pg per cell is indicative of the presence of cancer cells. Preferably, the value range of 0.001 to 0.03 pg/cell, more preferably 0.002 to 0.02 pg/cell, even more preferably 0.005 to 0.02 pg/cell is indicative of the presence of cancer cells.

The value range superior or equal to 0.05 pg/cell, preferably superior to 0.06 pg/cell, more preferably superior to 0.07 pg/cell, more preferably superior to 0.08 pg/cell, more preferably superior to 0.09 pg/cell, more preferably superior to 0.10 pg/cell, more preferably superior to 0.11 pg/cell, more preferably superior to 0.12 pg/cell, more preferably superior to 0.13 pg/cell, more preferably superior to 0.14 pg/cell, more preferably superior to 0.20 pg/cell, more preferably superior to 0.24 pg/cell, more preferably higher than 0.30 pg/cell is indicative of the presence of CSCs. As a particular example, the value of 0.08 pg per cell is indicative of the presence of CSCs.

The protocol may involve sub-dividing the tumor in smaller fractions and titrating iron in various areas of the tumor plotted against a given number of cells. The titration method used to quantify iron is atomic adsorption spectrometry for the iron titrated ex vivo. Alternatively, the patient may be treated with radiolabeled iron prior MRI evaluation of the tumor content of iron. This can be done prior to surgery. Finally, histological analysis of several parts of the tumor may be used to detect and quantify iron. An iron detection assay using Ferene S (complex absorption at 593 nm) can be used to quantify iron levels with high accuracy.

No discrimination between iron(II)/iron(III) should be made given that both degrees of oxidation are interchangeable over time.

In the context of the invention, "quantitative" means superior or equal to 0.05 pg of total iron per cell, preferably about 0.08 pg of total iron per cell, can be considered a suitable threshold above which cells exhibit a stem character. This threshold may be used to apply a therapy based on iron targeting and as a predictor of relapse.

The total level of iron can be measured from the tumor mass obtained from surgery where cells can be counted by means of cell sorting. Alternatively, the total level of iron can be plotted against the tumor mass.

In particular, the reference value could be defined (total level of iron/tumor mass). In practice, quantifying iron against a number of cells is durable and will be more accurate.

By "biological sample", it is meant tumor mass obtained from surgery where cells can be counted by means of cells sorting. The biological sample is obtained by biopsy.

In a preferred embodiment, the invention relates to the use of a combination of markers comprising total cellular iron and one or more biomarkers selected from IRP2, ferritin, Wnt1, TfR, ALDH, IRGS, and cathepsin B to detect CSCs.

The term "biomarker" as used herein, means a material capable of distinguishing CSCs from cancer cells, preferably breast cells, of assessing disease progression, survival, or disease-free survival after treatment of breast cancer such as resection, and may include an organic biomolecule such as a polypeptide, a nucleic acid (e.g. mRNA, etc.), a lipid, a glycolipid, a glycoprotein, and a sugar (monosaccharide, disaccharide, oligosaccharide, etc.), which is expressed at a higher or lower level, as compared to its level in normal cells. With respect to the objects of the present invention, the biomarker for breast cancer of the present invention is IRP2, ferritin, Wnt1, TfR, ALDH and/or cathepsin B, which are highly concentrated in breast CSCs, as compared to the cancer breast cancer cells. The biomarker of breast cancer of the present invention may further comprise, either additionally or alternatively, the Iron Regulatory Gene Signature or IRGS, as described in Miller et al., 2011, An Iron Regulatory Gene Signature Predicts Outcome in Breast Cancer, Cancer Res. 71(21): 6728-6737. The use of these biomarkers is in the context of breast cancer and the skilled man would consider other combinations of biomarkers for other cancers.

As used herein, "IRP2" has a 73-amino acid insertion, and this insertion mediates the IRP2 degradation in iron-replete cells.

As used herein, "ferritin" is a ubiquitous intracellular protein that stores iron and releases it in a controlled fashion. The protein is produced by almost all living organisms, including algae, bacteria, higher plants, and animals. In humans, it acts as a buffer against iron deficiency and iron overload. Ferritin is found in most tissues as a cytosolic protein, but small amounts are secreted into the serum where it functions as an iron carrier. Plasma ferritin is also an indirect marker of the total amount of iron stored in the body, hence serum ferritin is used as a diagnostic test for iron deficiency anemia.

As used herein "Wnt1" is a protein of the Wnt family encoded by the gene Wnt1. The transduction is under the control of the Wnt/β-catenin signal transduction pathway plays a central role in stem cell development, and its aberrant activation can cause cancer. Wnt/β-catenin signaling regulates OCT4 at transcriptional level the expression. OCT4, in concert with other transcription factors such as Nanog and Sox2, controls the self-renewal and the maintenance of CSCs. The Wnt/β-catenin signaling pathway is also involved in the induction of EMT, which is closely related to the acquisition of a stemness phenotype. Wnt-1 is upregulated in tumors.

As used herein "TfR" is Transferrin receptor, is a carrier protein for transferrin. It is needed for the import of iron into the cell and is regulated in response to intracellular iron concentration. It imports iron by internalizing the transferrin-iron complex through receptor-mediated endocytosis. Low iron concentrations promote increased levels of transferrin receptor, to increase iron intake into the cell. Thus, transferrin receptor maintains cellular iron homeostasis. TfR production in the cell is regulated according to iron.

As used herein "ALDH" comprises aldehyde dehydrogenase enzymes, including ALDHA1 and other isozymes. ALDH is originally known for its role in detoxifying aldehyde substrates, oxidizing them to carboxylic acid, but has also been implicated in other biological activities including stem cell differentiation and expansion. ALDH expression may be inducible or constitutive, and has notably been shown to be highly expressed in adult stem cells, including those isolated from breast tissue.

As used herein "IRGS" or "Iron Regulatory Gene Signature" comprises 16 iron regulatory genes, including CYBRD1, STEAP1, STEAP2, HFE, SCARA5, LTF, TFRC, SLC40A1, ISCU, SFXN1, EPAS1, SLC25A37, ABCG2, SFXN5, HIF1AN, and ALAD for predicting breast cancer outcome, as described in Miller et al., 2011.

As used herein "Cathepsin B" is an enzymatic protein belonging to the peptidase (or protease) families. A wide array of diseases result in elevated levels of cathepsin B, which causes numerous pathological processes including cell death, inflammation, and production of toxic peptides.

Use of the Total Cellular Iron Balance for Killing CSCs

In another aspect, the invention concerns the use of total cellular iron, in particular of body ferrous ($Fe^{2+}$) and ferric ($Fe^{3+}$) iron balance, as a lever of CSC death in a mammal, wherein said CSC death is preferably mediated by ROS production.

As used herein, "iron balance" means that iron II is oxidized by hydrogen peroxide to iron III, forming a hydroxide ion in the process. Iron (III) is then reduced back to iron (II) by another molecule of hydrogen peroxide, forming a hydroperoxyl radical and a proton. The net effect is a disproportionation of hydrogen peroxide to create two different oxygen-radical species, with water ($H^+ + OH^-$) as a byproduct.

$$Fe^{2+} + H_2O_2 \rightarrow Fe^{3+} + HO. + OH^- \quad (1)$$

$$Fe^{3+} + H_2O_2 \rightarrow Fe^{2+} + HOO. + H+ \quad (2)$$

The Fenton reaction has importance in biology because it involves the creation of free radicals by chemicals that are present in vivo. Transition-metal ions such as iron and copper donate or accept free electrons via intracellular reactions and help in creating free radicals. Most intracellular iron is in ferric (+3 ion) form and must be reduced to the ferrous (+2) form to take part in the Fenton reaction. Since superoxide ions and transition metals act in a synergistic manner in the creation of free radical damage, iron supplementation must not be done in patients with any active infections or in general any diseases.

As used herein "lever of CSC death" means that $Fe^{3+}$ allows the generation of ROS production in cells, thereby triggering cell death, which may comprise one or more of iron mediated cell death, lysosomal mediated cell death, and ferroptosis.

A preferred embodiment is the use of total cellular iron, wherein said CSC death is mediated by ROS production. Preferably, the total cellular iron is under the form $Fe^{2+}$ and or $Fe^{3+}$.

Another embodiment is the use of total cellular iron, as defined above, for selecting an iron chelating agent, wherein said iron chelating agent is a weak iron chelating agent.

In particular, in the context of the invention, the molecule, also called "weak iron-chelating agent," as defined above, allows binding $Fe^{2+}$ and $Fe^{3+}$ in CSCs. This generates a need for $Fe^{3+}$ in the cytosol. Then, ferritin releases $Fe^{3+}$, which stays free and generates ROS. Thus, it refers to compounds that are capable of binding iron. They are used as a treatment for metal poisoning. Typically, the binding constant (Kd) of DFO (deferoxamine) for iron is very low which means that the affinity is very strong. In the context of the invention, compounds that have a lower affinity than DFO are of interest. Analogs of salinomycin are considered as weak iron-chelating agents.

As used herein "weak" means defined by a binding constant, itself defined by on and off rates. Weak chelation refers to chelation that occurs in the millimolar range while strong chelation means within the nanomolar range. There is a gradation between the two.

Diagnosis of Cancer

A high level of iron in a tumor sample of a patient with cancer correlates to the presence of CSCs, preferably breast CSCs. Another aspect of the invention is thus an in vitro method for diagnosing cancer in a subject, comprising at least:

a) Measuring the amount of total cellular iron, preferably under the form of ferrous iron ($Fe^{2+}$) in a biological sample from a subject; and b) Comparing said amount measured in step a) to a reference value range for total cellular iron, wherein an amount of total cellular iron as measured in step a) higher than said reference value range is indicative of the presence of CSCs, thereby indicating that said subject has a cancer.

According to another embodiment of the in vitro method wherein said total cellular iron is under the form of ferrous iron ($Fe^{2+}$).

According to a preferred embodiment, said in vitro method is for diagnosing cancer having a high risk of recurrence, a high risk of metastasis and/or a cancer with resistance to therapy, in a subject.

The term "subject has a cancer" means, according to the invention, a subject who needs a treatment, in particular it is a diseased subject, including human beings, nonhuman primates or other animals, in particular mammals such as cows, horses, pigs, sheep, goats, dogs, cats or rodents such as mice and rats. In a particularly preferred embodiment, the term "subject has a cancer" can be used interchangeably with the term "patient" and preferably it is a human being.

In a preferred embodiment, the present invention concerns the in vitro method as defined above, wherein said reference value range is the amount of total cellular iron in a control sample from one or more normal subjects In still another embodiment, the present invention concerns the in vitro method as defined above, wherein said biological sample and/or said control sample is a biopsy.

In the context of the invention "control sample" means that in a first case only the test samples could be taken from cancer cells, if it is considered that the control consists of healthy samples. Alternatively, control could consist of samples in subjects which are already known to have cancer, and in this case only the test samples could be healthy. All biological samples are from biopsies. In a particular embodiment, the present invention concerns the in vitro method, wherein the presence of CSCs is indicative of breast cancer.

In the context of the invention, "breast cancer" means the cancer that develops from breast tissue.

The differences in tumor subtypes are hypothesized to reflect different mutation profiles, as well as differences in the cell of origin (Perou et al. 2000; Gusterson et al. 2005).

In a preferred embodiment, the in vitro method is as described above, wherein the presence of CSCs is indicative of invasive cancer.

In the context of the invention, "invasive cancer" means the cancer cells break out from inside the lobules or ducts and invade nearby tissue. With this type of cancer, the abnormal cells can reach the lymph nodes, and eventually make their way to other organs (metastasis), such as the bones, liver or lungs. The abnormal (cancer) cells can travel through the bloodstream or the lymphatic system to other parts of the body; either early on in the disease, or later. For example, in the context of the invention, the invasive cancer is an invasive breast cancer.

In a preferred embodiment, the in vitro method is as described above, wherein said subject is a human being.

In a preferred embodiment, the in vitro method of the invention is as described above, wherein said step a) is performed by at least one method selected from: atomic adsorption spectrometry, colorimetric test, and any methods well known by the skilled man, for example, electrospray ionization, tandem mass spectrometry, and mass spectrometry. The cited methods are purely illustrative.

As used herein, "atomic adsorption spectrometry" or "AAS" refers to a spectroanalytical procedure for the quantitative determination of chemical elements using the absorption of optical radiation (light) by free atoms in the gaseous state.

In the present invention, the term "mass spectrometry" or "MS" refers to an analytical chemistry technique that helps identify the amount and type of chemicals present in a sample by measuring the mass-to-charge ratio (m/z ratio) and abundance of gas-phase ions.

In the present invention, the term "electrospray ionization" or "ESI" refers to a technique used in mass spectrometry to produce ions using an electrospray, in which a high voltage is applied to a liquid to create an aerosol. Mass spectrometry using ESI is called electrospray ionization mass spectrometry (ESI-MS) or electrospray mass spectrometry (ES-MS).

In the present invention, the term "tandem mass spectrometry" or MS/MS refers to any general method involving at least two stages of mass analysis, either in conjunction with a dissociation process or in a chemical reaction that causes a change in the mass or charge of an ion.

In the present invention, the term "colorimetric test" is a technique used to determine the concentration of colored compounds in solution. A colorimeter is a device used to test the concentration of a solution by measuring its absorbance of a specific wavelength of light (not to be confused with the tristimulus colorimeter used to measure colors in general).

To use the colorimeter, different solutions must be made, including a control or reference of known concentration.

By "reference concentration of iron" or "normal iron levels" is meant the iron concentration in a normal cell, or in a cell that is not a CSC. For example, normal serum iron contains 10-40 µM, while cells such as non-tumoral or non-CSC cancer cells typically contain 0.01 to 0.04 pg iron/cell. Advantageously, in the context of the invention, the reference concentration of iron is 0 to 0.04 pg iron/cell. Preferably, the reference concentration of iron is 0.001 to 0.03 pg/cell, more preferably 0.002 to 0.02 pg/cell, even more preferably 0.005 to 0.02 pg/cell.

In a preferred embodiment, the in vitro methods defined above further comprise a step c) of measuring the amount of one or more biomarkers selected from IRP2, ferritin, Cathepsin B, Wtn1, ALDH, IRGS, Tfr, and a step d) of comparing said amount measured in step c) to a reference value for said biomarker.

More preferably, the cathepsin is in the activated form.

In still another preferred embodiment, said step c) is performed by at least one method selected from: Western blot, ELISA, dot-blot.

Thus, specific embodiments of quantifying the selected biomarkers according to the in vitro diagnosis method described herein encompass those wherein:
  (i) the selected biomarkers are quantified by immuno-chemical methods, which encompass quantification of one or more protein biomarkers of interest by immuno-detection methods, for example using antibodies directed specifically against each of the said one or more protein biomarkers, according to well-known immuno-detection methods, e.g. flow cytometry, and
  (ii) the selected biomarkers are quantified by gene expression analysis, which encompasses quantification of one or more biomarker mRNAs of interest, for example by performing a Real-Time PCR Taqman PCR analysis, according to well-known methods.

Quantifying one or more biomarkers can be accomplished by methods well-known in the art.

According to this embodiment of the in vitro diagnosis method described herein, quantifying the level of cellular protein expression may be performed for instance (i) by measuring the amount of said protein contained in a whole cell sample or (ii) by measuring the amount of said protein that is present at the cell surface, for example Tfr.

Measuring the amount of a protein biomarker of interest contained in a whole cell sample may be performed by Western blotting starting from the soluble fraction of a cell lysate and using an antibody directed against said protein biomarker of interest, according to methods that are well-known by one skilled in the art.

The term "antibody" as used herein designates a polypeptide that exhibits binding specificity to a specific antigen. More particularly, an antibody (or "immunoglobulin") consists of a glycoprotein comprising at least two heavy (H) chains and two light (L) chains inter-connected by disulfide bonds. Each heavy chain comprises a heavy chain variable region (or domain) (known as $V_H$) and a heavy chain constant region (known as $C_H$). Heavy chains are classified as gamma, mu, alpha, delta, or epsilon, and define the antibody's isotype as IgG, IgM, IgA, IgD, and IgE, respectively. The $C_H$ region of the immunoglobulin IgG, IgD, and IgA ($\gamma$, $\delta$ and $\alpha$ chains respectively) comprises three domains (CH1, CH2, and CH3) and a hinge region for added flexibility, while the CH region of the immunoglobulin IgM and IgE contains 4 domains (CH1, CH2, CH3, and CH4). The antibodies can be polyclonal or monoclonal antibodies. For example, antibodies can be rabbit polyclonal antibodies or mouse monoclonal antibodies. Or, for example, the antibodies can be VHH antibodies.

Measuring the amount of a protein biomarker of interest that is present at the cell surface may be performed by immunochemistry, either by immuno-labeling of fixed cells or by flow immuno-cytometry, according to methods that are well-known by one skilled in the art.

In a preferred embodiment, the in vitro method as defined above uses a combination of markers comprising total cellular iron and one or more biomarkers selected from IRP2, Wnt1, Tfr, ALDH, IRGS, cathepsin B for diagnosing cancer.

Method of Treatment

The inventors have shown that iron could be used as a novel marker for the diagnosis or the detection of CSCs. They also provided evidence that a weak iron chelating agent such as a derivative of salinomycin (Sal) exhibits a more potent and selective activity against CSCs, preferably breast CSCs. They show that Sal and its derivatives interact with iron and sequester the metal in the lysosomes, thereby initiating ferritinophagy, iron-dependent ROS production and lysosomal cell death.

Thus, iron could be used as a novel target in therapy.

According to another aspect, the invention relates to a method for specifically killing CSCs in a mammal, comprising: administering to said mammal having CSCs a therapeutically-effective amount of an iron-chelating composition, wherein said composition binds total cellular iron under the form of ferrous ($Fe^{2+}$) and ferric ($Fe^{3+}$) iron in said mammal, thereby inducing ferritinophagy and ROS production responsible for specific CSC death in said mammal, optionally preventing drug resistance in said mammal by selectively targeting CSCs.

As used herein, "specifically" means the iron-chelating pharmaceutical composition essentially, exclusively and selectively targets the CSCs population. The mechanism of action is specific for iron and the iron concentration being higher in the CSCs, said pharmaceutical composition thus specifically targets the CSCs. "Targeting the CSCs" means selectively, exclusively and selectively destroying CSCs. In preferred embodiments, the target cell contains high level of iron, more specifically $Fe^{2+}$ and $Fe^{3+}$.

As used herein, "a therapeutically effective amount" means that the agents and compositions described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition. In particular, the term "effective amount" refers to the amount of a therapy that is sufficient to result in the prevention of the development, recurrence, or onset of cancer and one or more symptoms thereof, reduce the severity, the duration of cancer, ameliorate one or more symptoms of cancer, prevent the advancement of cancer, cause regression of cancer, and/or prevent cancer metastases. In an embodiment of the invention, the amount of a therapy is effective to achieve a stabilization, reduction or elimination of the cancer stem cell population and/or eradication, removal, or control of primary cancer, metastatic cancer and/or recurrent cancer.

An effective amount of an agent or composition described herein will depend on the condition to be treated, the severity of the disease, the individual parameters of the patient, including age, physiological condition, size and weight, the duration of treatment, the type of an accompanying therapy (if present), the specific route of administration and similar factors. Accordingly, the doses administered of the agents described herein may depend on several of such parameters. In the case that a reaction in a patient is insufficient with an initial dose, higher doses (or effectively higher doses achieved by a different, more localized route of administration) may be used. The agents and compositions described herein can be administered to patients to treat or prevent a cancer disease, e.g., a cancer disease such as described herein characterized by the presence of CSCs containing high level of iron $Fe^{2+}$.

In a preferred embodiment, the invention concerns the method as defined above, wherein said composition prevents drug-resistance and tumor recurrence in said mammal by specifically targeting CSCs.

In another preferred embodiment, the invention concerns the method as defined above, wherein said composition is co-administered with radiation therapy or chemotherapy.

In the context of the invention, "co-administered" means administered in combination. As used herein, the term "combination" in the context of the administration of a therapy refers to the use of more than one therapy or therapeutic agent. The use of the term "in combination" does not restrict the order in which the therapies or therapeutic agents are administered to a subject. A therapy or therapeutic agent can be administered prior to, concomitantly with, or subsequent to the administration of a second therapy or therapeutic agent to a subject. Preferably, the therapies or therapeutic agents are administered to a subject in a sequence, amount and/or within a time interval such that the therapies or therapeutic agents can act together. In a particular embodiment, the therapies or therapeutic agents are administered to a subject in a sequence, amount and/or within a time interval such that they provide an increased benefit than if they were administered otherwise, in particular, independently from each other. Preferably, the increased benefit is a synergistic effect.

Treatment of cancer represents a field where combination strategies are especially desirable since frequently the combined action of two, three, four or even more cancer drugs/therapies generates synergistic effects which are considerably stronger than the impact of a monotherapeutic approach. Thus, in another embodiment of the present invention, a cancer treatment may be effectively combined with various other drugs. Among these are e.g. combinations with conventional tumor therapies, multi-epitope strategies, additional immunotherapy, and treatment approaches targeting angiogenesis or apoptosis (for review see e.g. Andersen et al. 2008: Cancer treatment: the combination of vaccination with other therapies. Cancer Immunology Immunotherapy, 57(11): 1735-1743). Sequential administration of different agents may inhibit cancer cell growth at different check points, while other agents may e.g. inhibit neo-angiogenesis, survival of malignant cells or metastases, potentially converting cancer into a chronic disease. The following list provides some non-limiting examples of anti-cancer drugs and therapies which can be used in combination with the present invention.

According to the invention, the term "chemotherapy" relates to treatment with one or more chemotherapeutic agents or combinations of chemotherapeutic agents such as cytostatic agents or cytotoxic agents. Chemotherapeutic agents according to the invention include cytostatic compounds and cytotoxic compounds. Chemotherapy is the standard of care for multiple types of cancer. The most common chemotherapy agents act by killing cells that divide rapidly, one of the main properties of cancer cells. Thus, a combination with conventional chemotherapeutic drugs such as e.g. alkylating agents, antimetabolites, anthracyclines, plant alkaloids, topoisomerase inhibitors, and other antitumor agents which either affect cell division or DNA synthesis may significantly improve the therapeutic effects of the present invention by clearing suppressor cells, reboot of the immune system, by rendering tumor cells more susceptible to immune mediated killing, or by additional activation of cells of the immune system. A synergistic anti-cancer action of chemotherapeutic and vaccination-based immunotherapeutic drugs has been demonstrated in multiple studies (see e.g. Quoix et al. 2011: Therapeutic vaccination with TG4010 and first-line chemotherapy in advanced non-small-cell lung cancer: a controlled phase 2B trial. Lancet Oncol. 12(12): 1125-33; see also Liseth et al. 2010: Combination of intensive chemotherapy and anticancer vaccines in the treatment of human malignancies: the hematological experience. J Biomed Biotechnol. 2010: 6920979; see also Hirooka et al 2009: A combination therapy of gemcitabine with immunotherapy for patients with inoperable locally advanced pancreatic cancer. Pancreas 38(3): e69-74).

The most common chemo drugs used for early breast cancer include the anthracyclines (such as doxorubicin/Adriamycin® and epirubicin/Ellence®) and the taxanes (such as paclitaxel/Taxol® and docetaxel/Taxotere®). These may be used in combination with certain other drugs, like fluorouracil (5-FU or its prodrug capecitabine), cyclophosphamide (Cytoxan®), and carboplatin.

For cancers that are HER2 positive, the targeted drug trastuzumab (Herceptin®) is often given with one of the taxanes. Pertuzumab (Perjeta®) can also be combined with trastuzumab and docetaxel for HER2 positive cancers. Trastuzumab emtasine (Kadcyla®) is an antibody-drug conjugate. There are hundreds of chemotherapeutic drugs available which are basically suitable for combination therapies. Some (non-limiting) examples of chemotherapeutic drugs which can be combined with the present invention are carboplatin (Paraplatin), cisplatin (Platinol, Platinol-AQ), crizotinib (Xalkori), cyclophosphamide (Cytoxan, Neosar), docetaxel (Taxotere), doxorubicin (Adriamycin), erlotinib (Tarceva), etoposide (VePesid), fluorouracil (5-FU), gemcitabine (Gemzar), imatinib mesylate (Gleevec), irinotecan (Camptosar), liposome-encapsulated doxorubicin (Doxil), methotrexate (Folex, Mexate, Amethopterin), paclitaxel (Taxol, Abraxane), sorafinib (Nexavar), sunitinib (Sutent), topotecan (Hycamtin), trabectidin (Yondelis, bevacizumab (Avastin).

According to the invention, the term "surgery" relates to an operation to remove the tumor—and remains the foundation of cancer treatment. Surgery can be combined with other cancer treatments in order to delete any remaining tumor cells. Combining surgical methods with subsequent immunotherapeutic treatment is a promising approach which has been demonstrated countless times.

According to the invention, the term "radiation" or "radiation therapy" relates to a component of cancer treatment with approximately 50% of all cancer patients receiving radiation therapy during their course of illness. The main goal of radiation therapy is to deprive cancer cells of their multiplication (cell division) potential. The types of radiation used to treat cancer are photons radiation (x-rays and gamma rays) and particle radiations (electron, proton and neutron beams.) There are two ways to deliver radiation to the location of the cancer. External beam radiation is delivered from outside the body by aiming high-energy rays (photons, protons or particle radiation) to the location of the tumor. Internal radiation or brachytherapy is delivered from inside the body by radioactive sources, sealed in catheters or as seeds placed directly into the tumor site. Radiation therapy techniques which are applicable in combination with the present invention are e.g. fractionation (radiation therapy delivered in a fractionated regime, e.g. daily fractions of 1.5 to 3 Gy given over several weeks), 3D conformal radiotherapy (3DCRT; delivering radiation to the gross tumor volume), intensity modulated radiation therapy (IMRT; computer-controlled intensity modulation of multiple radiation beams), image guided radiotherapy (IGRT; a technique comprising pre-radiotherapy imaging which allows for correction), and stereotactic body radiation therapy (SRBT, delivers very high individual doses of radiation over only a few treatment fractions). For a radiation therapy review, see Baskar et al. 2012: Cancer and radiation therapy: current advances and future directions. Int. J Med Sci. 9(3): 193-199.

According to the invention, the term "chemotherapeutic agent" includes taxanes such as paclitaxel and docetaxel and platinum compounds such as cisplatin and carboplatin, and combinations thereof. Preferred combinations, in particular for the treatment of breast cancer, may comprise a combination of a taxane and a platinum compound such as a combination of paclitaxel and carboplatin. Further preferred combinations, in particular for the treatment of breast cancer, in particular of breast cancer stem cell tumors, may comprise a combination of a platinum compound such as cisplatin with etoposide and/or bleomycin. According to the invention a reference to a chemotherapeutic agent is to include any prodrug such as ester, salt or derivative such as conjugate of said agent. Examples are conjugates of said agent with a carrier substance, e.g. protein-bound paclitaxel such as albumin-bound paclitaxel. Preferably, salts of said agent are pharmaceutically acceptable.

In still another embodiment, the invention relates to the method as defined above, wherein said mammal is a human being.

Actually, in certain therapeutic strategies, DFO is used. Inventors have shown that DFO chelates iron II and III and poisons the reactivity of the metal so that it depletes iron from the pool but also prevents lysosomal iron from producing ROS. In contrast, salinomycin induces a depletion of iron but the binding does not lead to inhibition of the metal, which can still promote ROS in lysosomes following ferritin degradation.

The use of compounds such as analogs of salinomycin allows concentration of iron in the lysosome. The concentration of iron in the lysosome can promote ROS generation and lead to membrane permeabilization of lysosomes (PLM) and to cell death.

To promote iron accumulation in lysosomes using this treatment strategy, salinomycin analogs can be coupled to a pump inhibitor DMT1 through which, in normal cellular function, iron is transported before diffuse into the cell.

Thus, the inventors proposed a new therapeutic strategy using a new therapeutic treatment.

The agents and compositions provided herein may be used alone or in combination with conventional therapeutic regimens such as surgery, irradiation or chemotherapy.

In another aspect, the invention relates to an iron-chelating pharmaceutical composition for use in a method for specifically and/or selectively killing CSCs.

As defined in the international application PCT/EP 2015/070975, the inventors have discovered that 20-alkyl-amino derivatives of salinomycin having the following formula (I') possess a superior activity against CSCs and TICs:

wherein:

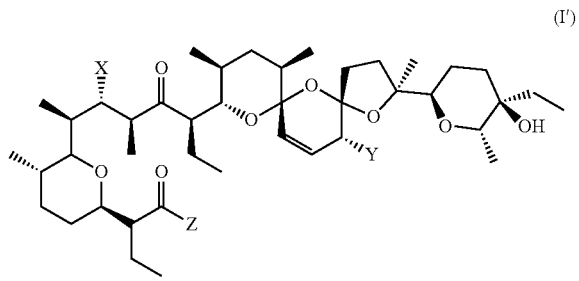

(I')

X is selected from the group consisting of OH and =O,
Y is selected from the group consisting of —NR$_1$R$_2$; —NR$_3$—(CH$_2$)$_n$—NR$_4$R$_5$; O—(CH$_2$)$_n$—NR$_4$R$_5$; —NR$_3$—(CH$_2$)$_n$—N$^+$R$_6$R$_7$R$_8$; and —O—(CH$_2$)$_n$—N$^+$R$_6$R$_7$R$_8$; and R$_1$ and R$_2$, identical or different, are selected from the group consisting of H; (C$_1$-C$_{16}$)-alkyl; (C$_3$-C$_{16}$)-alkenyl; (C$_3$-C$_{16}$)-alkynyl; aryl; heteroaryl; (C$_1$-C$_6$)-alkyl-aryl; (C$_1$-C$_6$)-alkyl-heteroaryl; or R$_1$ represents H and R$_2$ represents OR$_9$, where R$_9$ is H, (C$_1$-C$_6$)-alkyl, aryl and (C$_1$-C$_6$)-alkyl-aryl;

R$_3$ is selected from the group consisting of H; (C$_1$-C$_6$)-alkyl; (C$_1$-C$_6$)-alkyl-aryl;

R$_4$ and R$_5$, identical or different, are selected from the group consisting of H; (C$_1$-C$_6$)-alkyl; aryl; (C$_1$-C$_6$)-alkyl-aryl;

R$_6$, R$_7$ and R$_8$, identical or different, are selected from the group consisting of (C$_1$-C$_6$)-alkyl; aryl; (C$_1$-C$_6$)-alkyl-aryl;

n=2, 3, 4, 5 or 6,

Z is a functional group capable of chelating iron salts such as OH; NHNR$_9$R$_{10}$ (hydrazine), NHOC(O)R$_{11}$ (O-Acyl hydroxylamine), N(OH)—C(O)R$_{11}$ (N-acyl hydroxylamine), OOH, SR$_{12}$; 2-aminopyridine; 3-aminopyridine; —NR$_3$—(CH$_2$)$_n$—NR$_4$R$_5$; —NR$_3$—(CH$_2$)$_n$—OH; where:

R$_9$ and R$_{10}$, identical or different, are selected from the group consisting of H, (C$_1$-C$_6$)-alkyl, aryl and (C$_1$-C$_6$)-alkyl-aryl;

R$_{11}$ is selected from the group consisting of H; (C$_1$-C$_{16}$)-alkyl; (C$_3$-C$_{16}$)-alkenyl; (C$_3$-C$_{16}$)-alkynyl; aryl; heteroaryl; (C$_1$-C$_6$)-alkyl-aryl; (C$_1$-C$_6$)-alkyl-heteroaryl;

R$_{12}$ is selected from the group consisting of H; (C$_1$-C$_{16}$)-alkyl; (C$_3$-C$_{16}$)-alkenyl; (C$_3$-C$_{16}$)-alkynyl; aryl; heteroaryl; (C$_1$-C$_6$)-alkyl-aryl; (C$_1$-C$_6$)-alkyl-heteroaryl, and n=0, 2, 3 or 4.

The salinomycin derivates of said international application bear chemical modifications that favor iron binding and the Fenton reaction. The introduction of an alkyl-amine at position C-20 has proven to be very effective to improve the potency of salinomycin derivates against CSCs and their selectivity for CSCs over non-CSCs isogenic cells.

Thus, one aspect of the invention relates to an iron-chelating pharmaceutical composition that contains at least one component selected from: salinomycin and analogs of salinomycin, such as those described in the international application PCT/EP 2015/070975, and combinations thereof.

Preferably, said at least one salinomycin derivative or analog comprising an alkyl-amine at position C-20 is selected from AM5 (Sal-Propargylamine), AM23 (Sal-cyclopropylamine), and AM23S (corresponding to Sal-cyclopropylamine and further comprising an —SH group at position C-1)), as illustrated below, and combinations thereof.

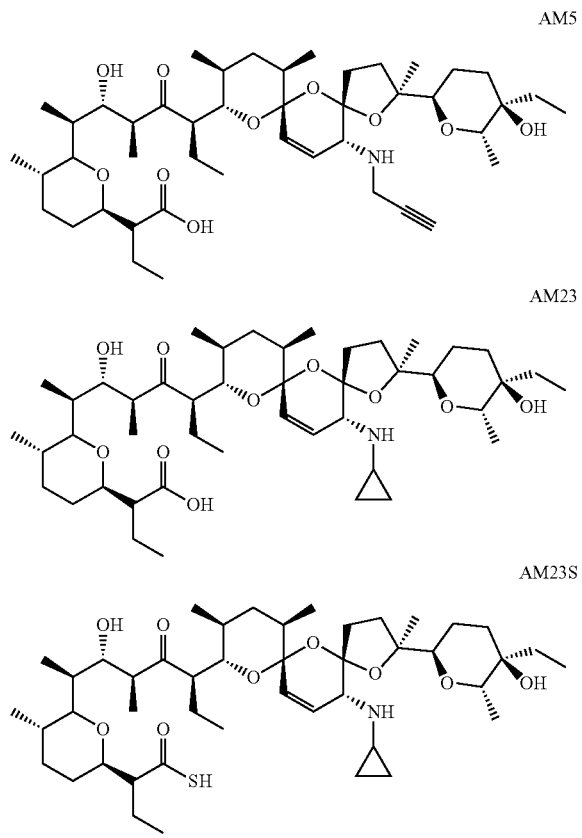

As an example, molecular editing of Sal using a chemoselective oxidation followed by a stereoselective reductive amination at C-20 led to the alkyne derivative AM5 along with its methylated counterpart AM9. The C-18-C-19 double bond was functionalized through a [π2s+π2s] photocycloaddition yielding the apolar alkyne derivative AM4.

According to a preferred embodiment, said iron-chelating composition of the invention comprises at least one component preferably selected from: salinomycin, analogs of salinomycin, more preferably AM5, AM23, or AM23S, autophagy inhibitors and combinations thereof.

According to a preferred embodiment, said iron-chelating composition of the invention consists of at least one component preferably selected from: salinomycin, analogs of salinomycin, more preferably AM5, AM23, or AM23S, autophagy inhibitors and combinations thereof.

Thus, another aspect of the invention is a method as defined above, or the iron-chelating pharmaceutical composition for use in a method for specifically and/or selectively killing CSCs, wherein said iron-chelating pharmaceutical composition contains at least one component preferably selected from: salinomycin, analogs of salinomycin, more preferably AM5, AM23, or AM23S, autophagy inhibitors, and combinations thereof.

In the context of the present invention, the autophagy inhibitors are well known by the skilled man. They can be chosen from the list, but not limited to: AKT inhibitor MK2206, RTK inhibitor sunitinib, alkylating agent temozolomide, specific inhibitor of mTOR:temsirolimus, sirolimus or vorinostat, Everolimus (RAD001), Cetuximab, alemtuzumab, mycophenolate, prednisone, pemetrexed in combination with irinotecan OSI-906, temozolomide and radiation histone deacetylases, inhibitor vorinostat, capecitabine, oxaliplatin, and bevacizumab, temozolomide, Proteasome inhibitor bortezomib, cyclophosphamide, dexamethasone, and rapamycin, EGFR inhibitor erlotinib, EGFR inhibitor gefitinib, Vinblastine panobinostat.

In a preferred embodiment, the invention concerns the method as defined above, or the iron-chelating pharmaceutical composition for use in a method for specifically and/or selectively killing CSCs, wherein said iron-chelating pharmaceutical composition contains at least one component preferably selected from: salinomycin, analogs of salinomycin, more preferably AM5, AM23, or AM23S, and combinations thereof.

In the present invention, the term "iron chelating" or "chelating agent" refers to compounds that are capable of binding total cellular iron.

Compounds that chelate iron tightly enough to prevent iron release from the lysosome, cellular iron depletion and ferritinophagy are of interest. These compounds may block Epithelial-Mesenchymale Transition (EMT) and favor Mesenchymale-Epithelial Transition (MET) instead and so block metastasis. In addition, those compounds that chelate iron but do not kill the redox potential of these compounds are of high interest since they can induce, in addition to iron depletion, the production of lethal ROS. Therefore, cell death should become proportional to iron levels and thus to stemness.

There are a variety of common chelating agents with differing affinities for different metals, physical characteristics, and biological mechanisms of action.

In the present invention, "chelation therapy" refers to a medical procedure that involves the administration of chelation agents to remove heavy metals from the body. Chelation therapy is used as a treatment for metal poisoning.

In a particular embodiment, the iron-chelating pharmaceutical composition for use in a method for treating cancer or in a method for preventing cancer progression in a subject in need thereof. Preferably, said cancer has a high risk of recurrence, a high risk of metastasis and/or is a cancer with resistance to therapy.

Another aspect of the invention relates to an iron-chelating pharmaceutical composition for use in a method for specifically killing CSCs.

In a preferred embodiment of the invention, the iron-chelating pharmaceutical composition for use is as defined above, wherein said subject is a human being.

Prognostic Use of Iron

Another aspect of the invention relates to an in vitro method for determining the prognosis of a subject diagnosed with cancer, comprising the steps:

a) Measuring the amount of total cellular iron in a biological sample from said subject after the subject has been treated with an appropriate antitumoral agent and/or an iron-chelating pharmaceutical composition;

b) Comparing said amount measured in step a) to a reference value range for total cellular iron.

In a preferred embodiment, the invention relates to the in vitro method as defined above, wherein an amount of total cellular iron as measured in step a) higher than said reference value range is indicative that the subject is at high risk of relapse, and wherein an amount of total cellular iron as measured in step a) in the reference value range is indicative that the subject has been successfully treated by said appropriate antitumoral agent and/or said iron-chelating pharmaceutical composition.

Preferably, in the in vitro method for determining the prognosis of a subject diagnosed with cancer, said cancer is a cancer having a high risk of recurrence, a high risk of metastasis and/or a cancer with resistance to therapy.

In a preferred embodiment, the appropriate antitumoral treatment is selected from: doxorubicin, paclitaxel, campothecin, actinomycin D, staurosporine, carboplatin, oxaliplatin, and combination thereof.

In a preferred embodiment, in the in vitro method as defined above, wherein if said subject is at high risk of relapse, then the method further comprises a step of re-treating said subject with said iron-chelating pharmaceutical composition alone or in combination with said appropriate antitumoral treatment or treatment with the iron chelator prior regular chemotherapy.

In the context of the invention, "high risk of relapse" or "high risk of recurrence" means that the disease subject is at risk of developing cancer, or of having remaining CSCs after treatment. In the context of the invention, the subject is at risk of relapse if the iron concentration is equal to or higher than 0.05 pg/cell, preferably higher than 0.06 pg/cell, more preferably higher than 0.07 pg/cell, more preferably higher than 0.08 pg/cell, more preferably higher than 0.09 pg/cell, more preferably higher than 0.10 pg/cell, more preferably higher than 0.11 pg/cell, more preferably higher than 0.12 pg/cell, more preferably higher than 0.13 pg/cell, more preferably higher than 0.14 pg/cell, more preferably higher than 0.20 pg/cell, more preferably higher than 0.24 pg/cell, more preferably higher than 0.30 pg/cell. According to a preferred embodiment, the subject is at risk of relapse if the iron concentration is about 0.08 pg/cell.

In a preferred embodiment, the in vitro method as defined above uses a combination of markers comprising total cellular iron and one or more biomarkers selected from: IRP2, ferritin, Wnt1, Tfr, ALDH, IRGS, and cathepsin B, to determine the risk of relapse in a human subject.

The compounds and pharmaceutical compositions described herein may be administered orally, parenterally, preferably by oral administration or administration by injection.

In some embodiments, the compound or pharmaceutical composition is administered to a subject parenterally. The term parenteral as used herein includes subcutaneous, intracutaneous, intravenous, intramuscular, intraarticular, intraarterial, intrasynovial, intrasternal, intrathecal, intralesional and intracranial injection or infusion techniques. In some embodiments, the compound or pharmaceutical composition is configured for intravenous administration.

In some embodiments, the method further comprises administering an additional cancer treatment e.g., radiation therapy, chemotherapy, or hormone therapy in combination with the compound or composition described herein. In some embodiments, the additional cancer treatment is administered simultaneously with the compound or pharmaceutical composition. In some embodiments, the additional cancer treatment is administered sequentially with the compound or pharmaceutical composition described herein. In some embodiments, the additional cancer treatment is chemotherapy. In some embodiments, the chemotherapy is a taxane, e.g., docetaxel, paclitaxel, or cabazitaxel. In some embodiments, the chemotherapy is a platinum compound, e.g., cisplatin. In some other embodiments, the chemotherapy is an anthracycline, e.g., doxorubicin.

The absolute amount will depend upon a variety of factors including the concurrent treatment, the number of doses and the individual subject parameters including age, physical condition, size and weight. These are factors well-known to those of ordinary skill in the art and can be addressed with no more than routine experimentation. It is often the case that a maximum dose be used, that is, the highest safe dose according to sound medical judgment. The dose used may be the maximal tolerated dose or a sub-therapeutic dose or any dose there between. Multiple doses of iron-chelating agent of the invention are also contemplated. When the iron-chelating agent of the invention is administered in combination, a sub-therapeutic dosage of either of the molecules, or a sub-therapeutic dosage of both, may be used in the treatment of a subject having, or at risk of developing cancer, and thus exhibiting or at risk of exhibiting CSCs. When the two classes of drugs are used together, the cancer medicament may be administered in a sub-therapeutic dose to produce a desirable therapeutic result. A sub-therapeutic dose is a dosage which is less than that dosage which would produce a therapeutic result in the subject if administered in the absence of the other agent. Thus, the sub-therapeutic dose of a cancer medicament is one which would not produce the desired therapeutic result in the subject in the absence of the administration of the molecules of the invention. Therapeutic doses of cancer medicaments are well known in the field of medicine for the treatment of cancer. These dosages have been extensively described in references such as Remington's Pharmaceutical Sciences, 18th ed., 1990; as well as many other medical references relied upon by the medical profession as guidance for the treatment of cancer.

Lower or higher doses than those recited above may be required. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Monitoring an Anticancer Therapy

The present invention provides means and methods for following the anti-cancer therapy and assessing the risk of relapse, based on the detection of the iron level in the CSCs.

Another aspect of the invention is an in vitro method for monitoring the efficacy of an antitumoral therapy in a subject undergoing said therapy, comprising at least:

a) Measuring the amount of total cellular iron in a biological sample from said subject at a time T1, b) Measuring the amount of total cellular iron in a biological sample from said subject at a time T2, c) Comparing said amount measured in step a) to said amount measured in step b) above, wherein an amount of total cellular iron as measured in step b) identical or higher than said amount measured in step a) is indicative that the subject is not responsive to said therapy, and wherein an amount of total cellular iron as measured in step b) less than said amount measured in step a) is indicative that the subject is responsive to said therapy.

The amount of total cellular iron in the biological sample can be measured by immunohistochemistry.

As used herein, T1 means before or during or after the subject has been administered said antitumoral therapy comprising an appropriate antitumoral agent and/or an iron-chelating pharmaceutical composition;

As used herein, T2 means before or during or after the subject has been administered said antitumoral therapy comprising an appropriate antitumoral agent and/or an iron-chelating pharmaceutical composition, wherein said time T2 is posterior to said time T1.

Preferably said subject has been diagnosed with cancer, said cancer having a high risk of recurrence, a high risk of metastasis and/or a cancer with resistance to therapy.

As used herein, "a subject is not responsive" meant that the subject, also called the patient, is not treated with the appropriate therapy or composition. The total cellular iron concentration is still elevated and the CSCs are not killed.

As used herein, "a subject is responsive" means that the subject, also called the patient, is treated with an appropriate therapy or composition.

In a preferred embodiment, in the in vitro method as defined above, wherein if said subject is responsive to said therapy, then the method further comprises a step of continuing said therapy, whereas if said subject is not responsive to said therapy, then the method further comprises a step of stopping said therapy.

In a preferred embodiment, the in vitro method as defined above further comprises re-performing steps a) to c).

In still another embodiment, the invention relates to said in vitro method, wherein if said subject is responsive to said therapy, then the method further comprises a step of stopping said therapy.

In still another embodiment, the invention relates to said in vitro method, wherein if said subject is not responsive to said therapy then the method further comprises stopping said therapy.

Screening for Compounds of Interest

The molecular axis involving iron is therefore a suitable target, to modulate the survival and proliferation of CSCs and, in particular, breast CSC survival. The present invention proposes a methodology for the screening of weak iron chelators that target specifically $Fe^{2+}$ and $Fe^{3+}$ in CSCs and are therefore efficient anti-cancer treatments thanks to the ROS production via degradation of ferritin which releases $Fe^{3+}$. This invention is of high interest for future medical applications.

Importantly, the compound(s) identified by the screening method of the invention would specifically affect CSCs because these cells contain a higher level of iron and are therefore more prone to this treatment.

Thus, in another aspect, of the invention, the present invention relates to a screening method for identifying compounds capable of inhibiting CSC properties such as self-renewal and proliferation, killing them specifically.

These properties may be tested by various methods such as clonogenic or sphere assays, in which single cells are assessed for their ability to differentiate and self-renew (Thomson SP, *Cancer Research*, 1982). Also, clonal cell transplantation systems can be used (Nakauchi et al, *Ann N Y Acad Sci.* 2001), as well as their ability to initiate tumor formation in vivo.

CSCs can be identified by various means. For example, it is possible to identify them by using distinctive set of cell surface markers including, CD44, CD24, E-cadherin, vimentine.

Alternatively, it is possible to identify CSCs by letting them grow in the absence of serum and without attachment to culture plates (differentiated cells fail to survive under the same conditions). Also, CSCs can be identified by their characteristic slow-cycling and quiescent properties (Horan PK, *Methods Cell Biol.* 1990).

In a preferred embodiment, the CSCs targeted by the compound of the invention are those present in cancer associated with iron surplus, in particular breast cancer, head and neck cancer, lung cancer, ovarian cancer, pancreatic cancer, colorectal carcinoma, cervical cancer, sarcomas, brain tumors, renal cancer, melanoma and skin cancer, prostate cancer, gastric cancer, multiple myeloma, leukemia and lymphoma.

In a particularly preferred embodiment, CSCs targeted by the compound of the invention are breast CSCs.

In a preferred embodiment, the in vitro method for determining the antitumoral effect of a candidate agent in a subject, comprises at least the steps of:

a) Measuring the amount of total cellular iron in a biological sample from said subject before the subject is treated with said agent;

b) Comparing said amount measured in step a) to a reference value range for total cellular iron, thereby obtaining a first value;

c) Measuring the amount of total cellular iron in a biological sample from said subject after the subject has been treated with said agent;

d) Comparing said amount measured in step c) to said reference value range for total cellular iron, thereby obtaining a second value.

In a preferred embodiment, the in vitro method as defined above further comprises a step e) of comparing the results obtained in steps b) and d), thereby selecting said candidate compound if said second value as measured in step d) is less than said first value as measured in step b).

In a more preferred embodiment, this tested compound as candidate antitumoral agent is a weak iron chelating agent, more preferably salinomycin analogs, even more preferably AM5, AM23, and AM23S, impairing the iron cell concentration. Said compound or functional analog thereof can preferably bind iron CSCs, preferably $Fe^{2+}$, $Fe^{3+}$.

Preferably said subject has been diagnosed with cancer, said cancer having a high risk of recurrence, a high risk of metastasis and/or a cancer with resistance to therapy.

In another embodiment, said in vitro method, further comprises a step e) of comparing the results obtained in steps b) and d), thereby selecting said candidate if said second value in step d) is less than said first value in step b).

The efficacy of the compounds disclosed herein can be evaluated for their efficacy by contacting test cells and control cells with the compounds of interest. The test cells and control cells are then monitored for growth and/or survival. Compounds which result in different growth rates of the test cells compared to the control cells are selected for further testing and evaluation. For example, a panel of test cells may be contacted with different doses of the compound or a panel of test cells may be contacted with the compound for different durations of time. In some embodiments, the compounds are used to produce a response curve, wherein the test dose response curve indicates the level of inhibition of the test cells by the compound at a number of different doses. This analysis can be used to determine an EC50 value for the compound against the test cells and/or the control cells. In some cases, the EC50 value for the compound against the control cells is statistically significantly less than the EC50 value for the compound against the test cells. In other cases, the EC50 value for the compound against the control cells is statistically significantly greater than the EC50 value for the compound against the test cells.

In an embodiment, the compounds of the invention may be evaluated against CSCs and/or mesenchymal cells using techniques disclosed in PCT/EP 2015/070975, which is incorporated by reference in its entirety. In an embodiment, the compounds of the invention may be evaluated against CSCs and/or mesenchymal cells using techniques disclosed in "Identification of Selective Inhibitors of CSCs by High-Throughput Screening" by Gupta et al., Cell, vol. 138, p. 645-659 (2009), which is incorporated by reference in its entirety.

Additionally, it is possible to compare the efficacy of the compound disclosed herein against control compounds, e.g., other cancer therapeutics (e.g., doxorubicin, paclitaxel, campothecin, actinomycin D, staurosporine).

FIGURES

FIG. 1. Salinomycin and AM5 sequester iron in lysosomes and trigger ferritin degradation. a, Chemical strategy to visualize small molecules in cells. b, Fluorescence microscopy images of U2OS cells showing the subcellular localization of labeled Sal derivatives AM4, AM5, and AM9. Lysotracker Deep Red stains the lysosomes and 4',6-diamidino-2-phenylindole (DAPI) stains nuclear DNA. Scale bar, 10 μm. Zoom corresponds to ×6. c, Live cell fluorescence microscopy images showing the subcellular localization of iron(II) using the fluorogenic reduction of RhoNox-1 (green) in HMLER CD24$^{low}$ cells treated with Sal or AM5 or AM9 (0.5 μM) for 48 h. Lysotracker deep red stains the lysosomes (red) and DAPI stains nuclear DNA (blue). Scale bar, 10 μm. d, Fixed cell fluorescence microscopy images showing the subcellular localization of iron(II) using the fluorogenic reduction of RhoNox-1 (green) in HMLER CD24$^{low}$ cells treated with Sal or AM5 or AM9 (0.5 μM) for 48 h. e, Quantification of lysotracker-positive vesicles colocalizing with RhoNox-1 in fixed cells was carried out by means of visual inspection. At least 75 cells were counted per condition. Data represent three independent biological replicates (n=number of lysotracker vesicles). Bars and error bars correspond to mean values and s.d. of three biological replicates, respectively. f, Immunoblotting showing levels of iron homeostasis regulatory proteins in HMLER CD24$^{low}$ cells treated as indicated. g, Fluorescence microscopy images showing the subcellular localization of ferritin in HMLER CD24$^{low}$ cells treated as indicated for 6 h. Scale bar, 10 μm. Zoom corresponds to ×6. h, Immunoblotting showing levels of ferritin in HMLER CD2$^{low}$ cells treated as indicated for 24 h. i, Detection of iron(III) with Perl's reagent in tumor tissues of mice treated as indicated. Scale bar, 50 μm. j, $^1$H-NMR spectra of Sal+/−FeCl$_2$, anthracene and bipyridine. Spectra were recorded in CD$_3$CN. Arrows indicate proton signals affected by the presence of iron. Coordination of Sal to iron is arbitrary. k, $^1$H-NMR spectra of I. AM5 (2 mM) and Napht (1.0 mol equiv.), II. AM5 and Napht in the presence of FeCl$_2$ (0.5 mol equiv.), III. AM5, Napht and Bipy (1.6 mol equiv.) in the presence of FeCl$_2$ (Bipy added after FeCl$_2$), IV. AM5 and Bipy. I, $^1$H-NMR spectra of I. Sal (2 mM) and Napht (1.0 mol equiv.), II. Sal and Napht, in the presence of FeCl$_2$ (0.5 mol equiv.), III. Sal, Napht and Bipy (1.6 mol equiv.) in the presence of FeCl$_2$ (Bipy added after FeCl$_2$), IV. Sal and Bipy. For k and I, Samples prepared in CD$_3$OD, spectra recorded at 298 K, 5 min following sample preparation (600 MHz). Stars indicate proton signals shielded by iron(II). Boxed regions highlight signals of free Napht (boxed region of I, II, and III) and free/bound Bipy, (boxed region of III and IV), respectively.

FIG. 2. Salinomycin and AM5 promote iron-dependent lysosomal cell death via ROS production. a and b, Percentage of cell death of HMLER CD24$^{low}$ cells treated as indicated for 48 h. Measurements and quantification performed FACS using Annexin V FITC and PI fluorescence. P<0.01, *P<0.001, Student's t-test. c, Quantification of cellular iron by electrothermal atomic absorption spectrometry in HMLER cells. Error bars represent s.d. (n=3). **P<0.01, Student's t-test. d, Comparative immunoblotting analysis of endogenous levels of EMT markers, TfR and cathepsin B in HMLER cells.

Figure 3:
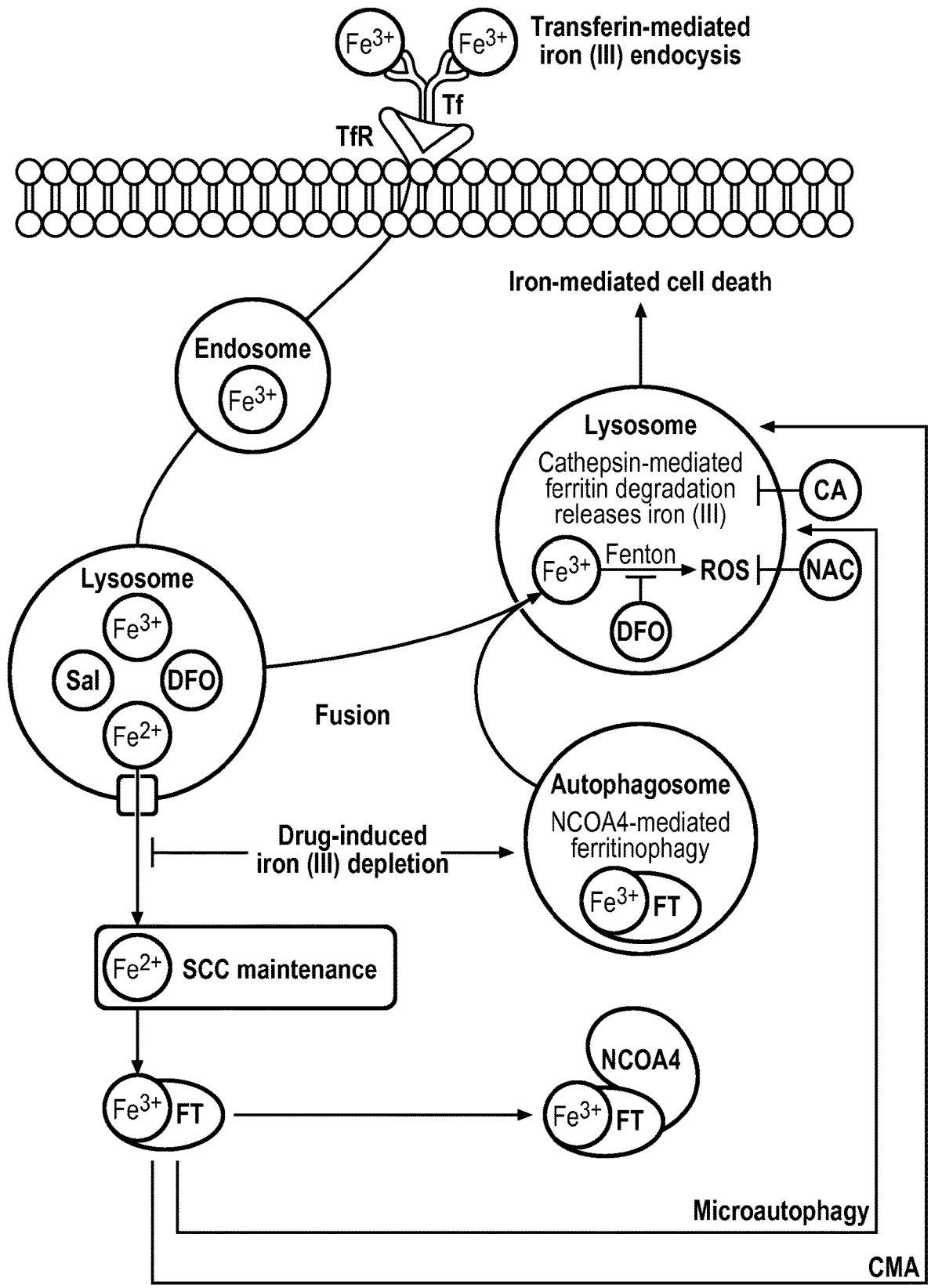

FIG. 3. Schematic illustration of salinomycin targeting iron homeostasis. Transferrin (Tf) and transferrin receptor (TfR) mediate iron endocytosis. Acidification of endocytic vesicles releases iron from transferrin, which is then reduced and exported to the cytosol. Iron can be stored as a non-toxic iron/ferritin (FT) complex. The iron chelator DFO and iron conjugated base Sal/AM5 can sequester iron in the lysosome and deplete the pool of cytosolic iron. Iron depletion triggers ferritin degradation by autophagy including NCOA4-mediated ferritinophagy and/or chaperone mediated autophagy (CMA) and/or endosome microautophagy. Although mechanisms through which ferritin was delivered to late endosomes/lysosomes remain to be fully characterized, microautophagy appears to be the central mechanism. Indeed, ferritin relocalization to the lysosomal compartment was also observed in absence of the ferritin cargo receptor NCOA4. Lysosome/autophagosome fusion or multivesicle body/lysosome fusion leads to the cathepsin-mediated degradation of ferritin to replenish the available pool of iron, an event that can be prevented by the cathepsin inhibitor CA-074 (CA). Iron promotes the production of ROS through Fenton-type chemistry, which can be prevented by iron chelation with DFO or scavenged by N-acetyl-L-cysteine (NAC). ROS induce lysosome membrane permeabilization and cell death. Black arrows indicate normal iron homeostasis. Red arrows indicate the response to Sal and AM5.

Figure 4A:
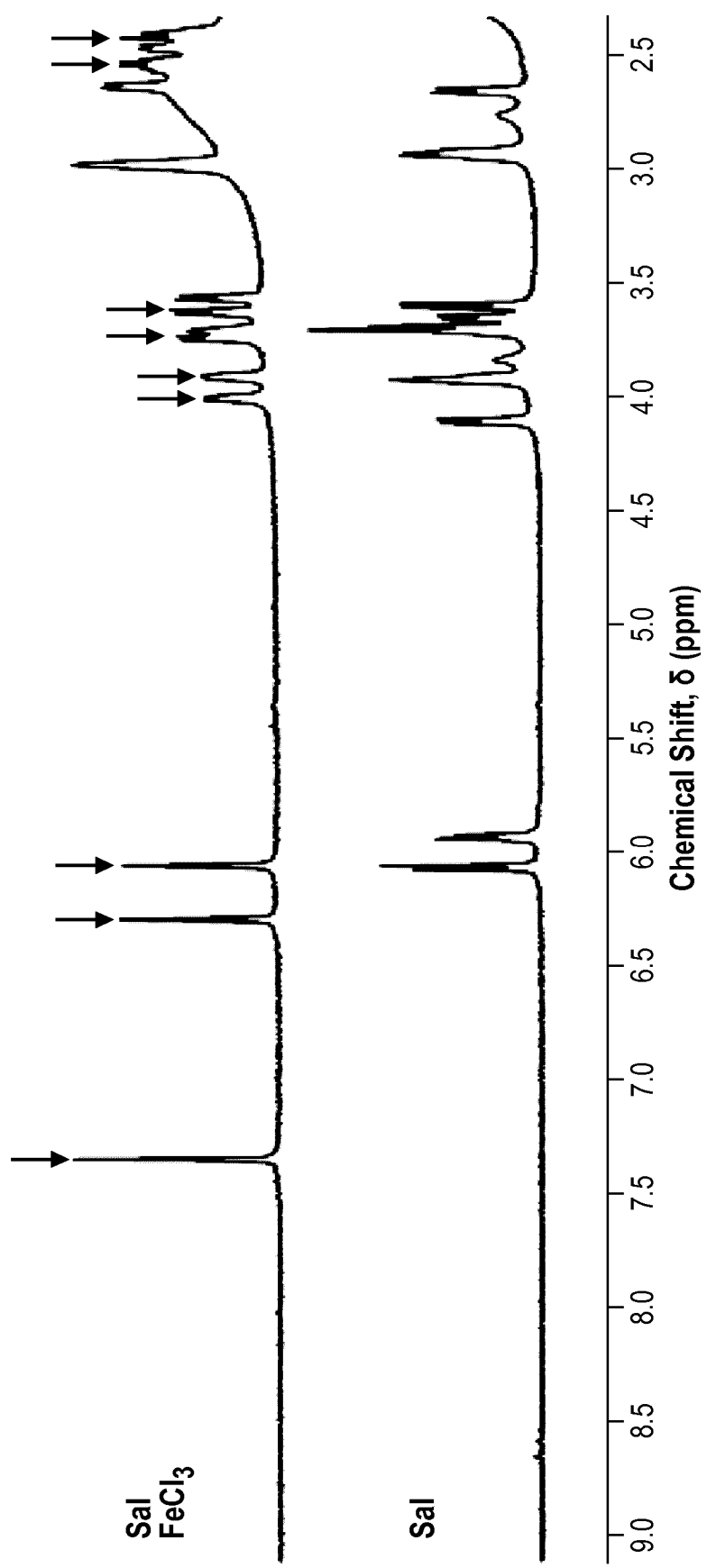
Figure 4B:
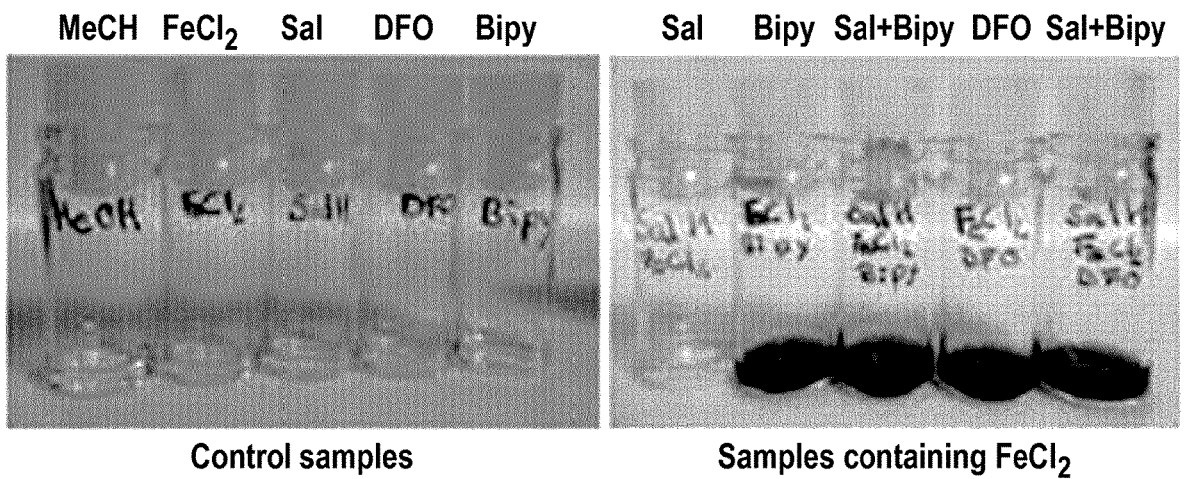
Figure 4C:
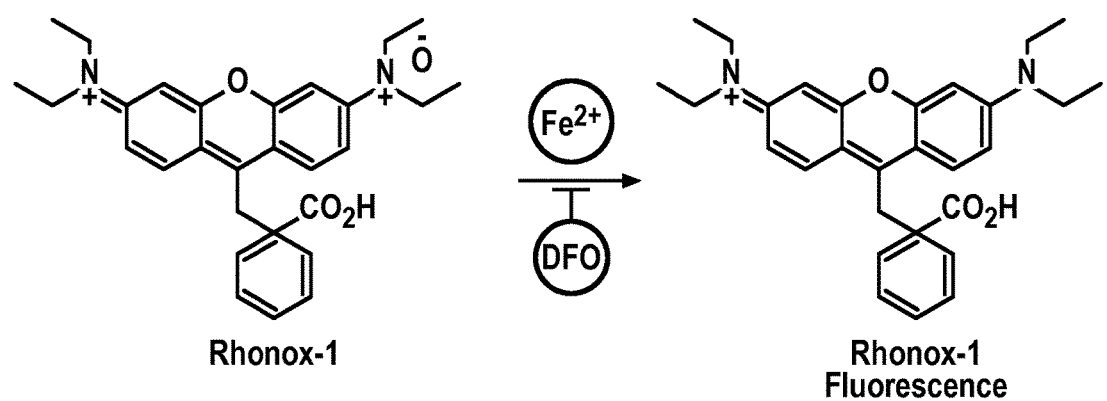

FIG. 4. Salinomycin interacts with iron without altering its reactivity.

a, $^1$H-NMR spectra of 5 mM Sal+/−FeCl$_3$ (0.5 mol equiv.). Spectra were recorded in CD$_3$CN at 298 K. Arrows indicate proton signals affected by the presence of iron. The signal at 7.4 ppm is characteristic hydrogen bonding and a more rigid supramolecular assembly of Sal with iron. b, Photographs of methanolic solutions of the indicated small molecules+/−iron(II). Color changes indicate the formation of distinct iron complexes. Picture was taken 1 minute after addition of DFO or 2,2'-bipyridyl (Bipy) when these compounds were added to vials already containing Sal and FeCl$_2$. The appearance of a color in the middle and far right vials indicates that Bipy and DFO outcompete Sal to form a complex with iron. c, Schematic illustration of the fluorogenic reduction of RhoNox-1 by iron (II) that can be inhibited by DFO. d, Quantification of the fluorogenic reduction of RhoNox-1 in the presence of iron (II) showing that DFO but not Sal poisons iron.

Figure 5:
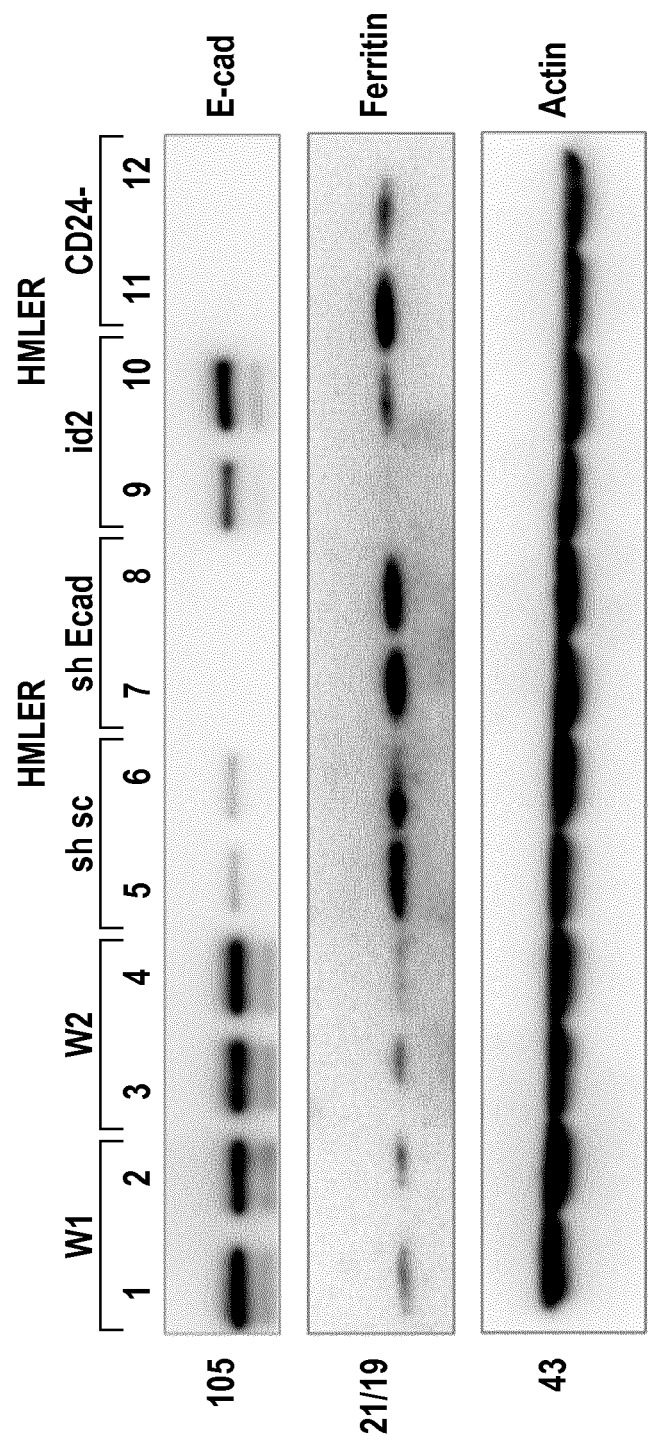

FIG. 5. Immunoblotting showing levels of E-Cad and Ferritin in parental and derivative HMLER cells.

Figure 6:
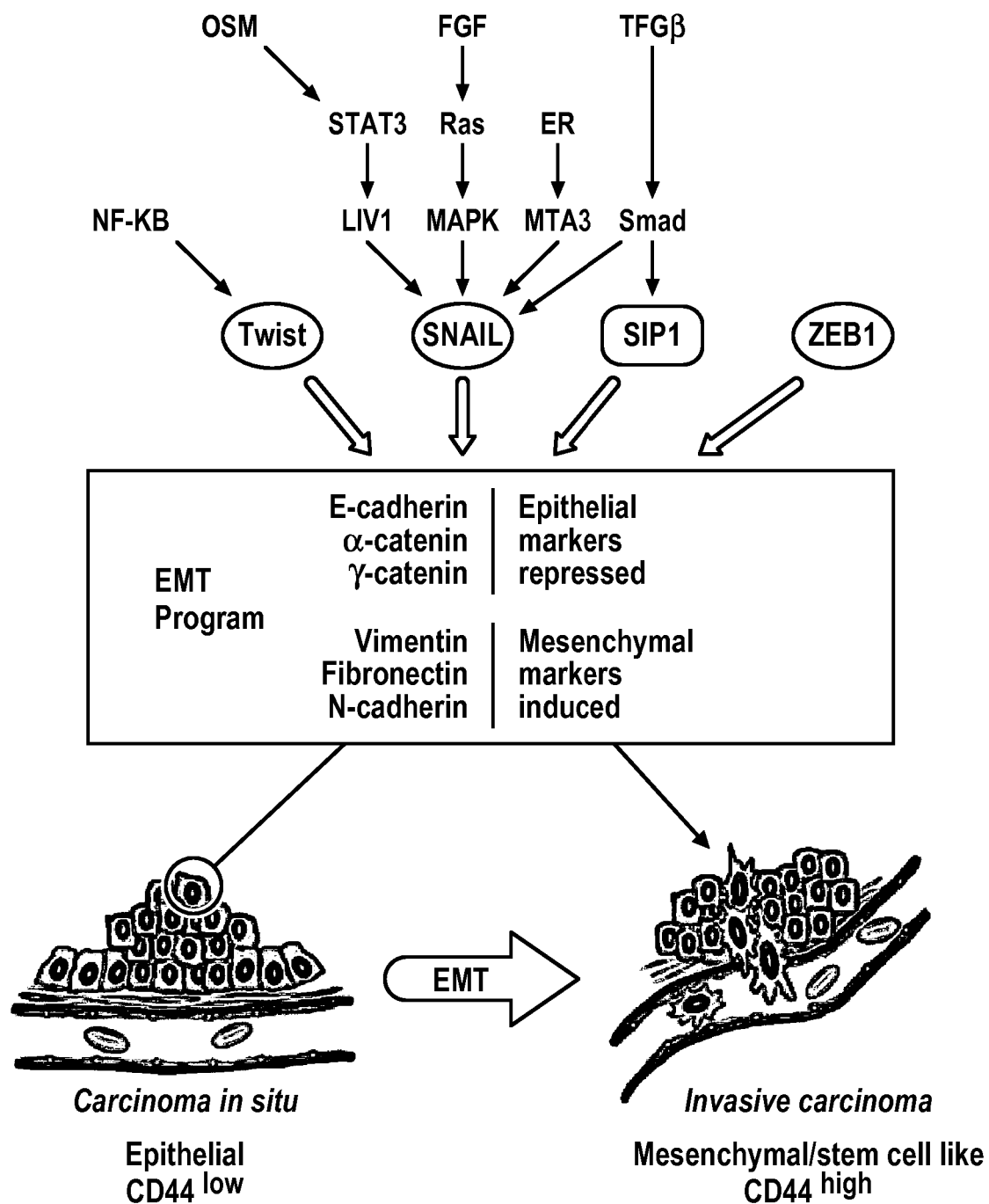

FIG. 6. Schematic representation of EMT

Figure 7:
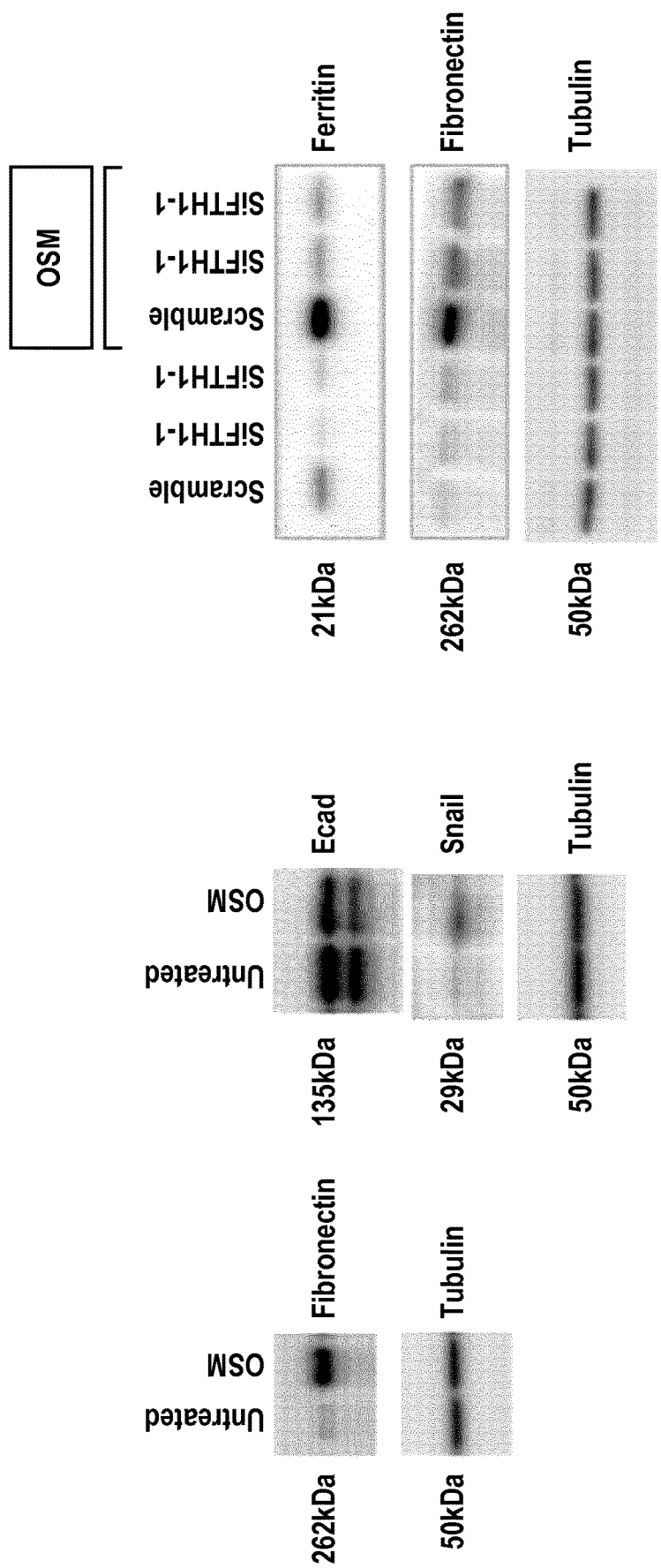

FIG. 7. Knock down of ferritin expression interferes with the OSM-mediated induction of EMT in MCF-7 cells. left, Immunoblotting showing levels of EMT markers in MCF-7 cells treated or not with 100 ng/ml of OSM for 72 h. right Immunoblotting showing levels of ferritin and fibronectin proteins in MCF-7 cells transfected with siRNA control (scramble) or siRNA targeting specifically ferritin mRNA (FTH1) during 48 h and then the cells were incubated with OSM (100 ng/ml) for 48 h. Beta-tubulin is used as loading control. MCF-7 were transfected.

FIG. 8. Knock down of ferritin expression interferes with the OSM-mediated induction of CD44$^{high}$CD24$^{low/-}$ in MCF-7 cells. MCF-7 were transfected with siRNA control or siRNA specifically targeting ferritin mRNA (FTH1) during 48 h and then the cells were incubated with OSM (100 ng/ml) for 48 h. a. Analysis of CD44 and CD24 expression by flow cytometry. Left panel, CSC indicates the percent of CD44$^{high}$/CD24$^{Low\ or\ negative\ (Low/-)}$ population gated. Right panels, histogram representations of CD44 or CD24 expression (dark grey), or by the isotype control (light grey). b. Graphs representing the percent mean of CD44$^{high}$/CD24$^{Low/-}$ population gated. c. Graphs representing the mean fluorescence intensity (IF) of CD24 and CD44, respectively. d. Quantification of the ALDH+ population in MCF-7 cells treated as indicated above, and measured by flow cytometry. Bars and error bars correspond to mean values and s.d. of two biological replicates, respectively. **P<0.01, ns, not significant, Student's t-test.

Figure 9:
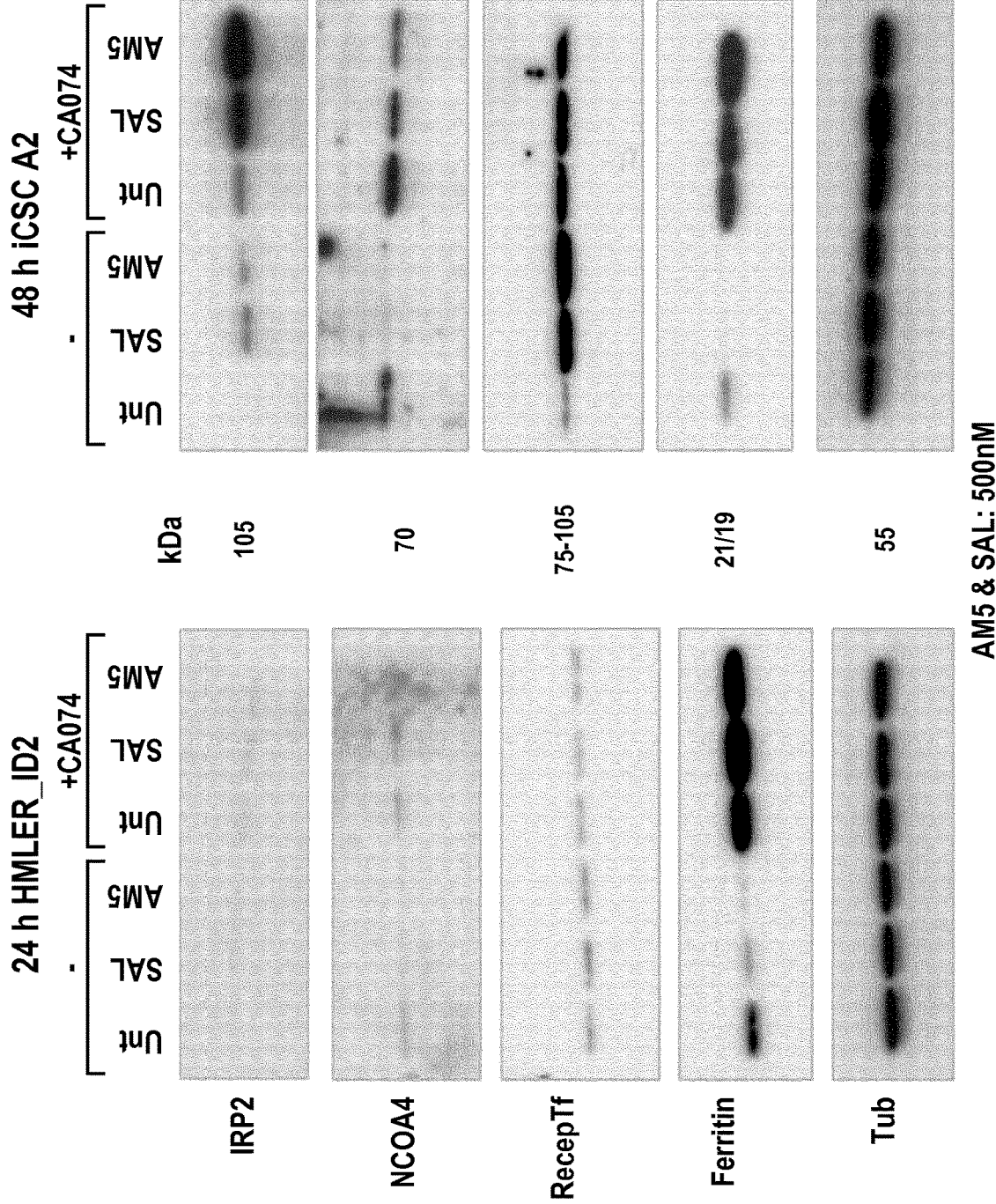

FIG. 9. Sal and AM5 effect on non-CSC and CSC cells. Immunoblotting showing levels of iron homeostasis regulatory proteins in HMLER CD44$^{Low}$ CD24$^{high}$ (HMLER_ID2) and iCSCA2 (another cancer stem cell) treated as indicated. CA 074 is cathepsin B inhibitor.

FIG. 10. HMLER CD24$^{Low}$ cells uptake transferrin more than its isogenic HMLER ID2 counterpart. Briefly, HMLER CD24$^{Low}$CD44$^{high}$ cells and its HMLER CD24$^{high}$ CD44$^{Low/-}$ ID2 counterpart are co-cultured at a ratio of 1:1 for 24 h and then are incubated with Transferrin-FITC (50 µg/mL) for the indicated times. Transferrin-FITC uptake was assessed by flow cytometry. a. CD24$^{Low}$CD44$^{high}$ HMLER cells were identified by CD44 expression (here, CD44-PE) to discriminate from ID2 cells which are CD44$^{Low/-}$. b. CD24$^{Low}$CD44$^{high}$ HMLER cells were stained by celltracker deep red dye (here, APC) to discriminate ID2 cells which are not stained before co-culture. c. Graphs representing the fluorescence intensity median of Transferrin-FITC for each population for the time indicated.

Figure 11:
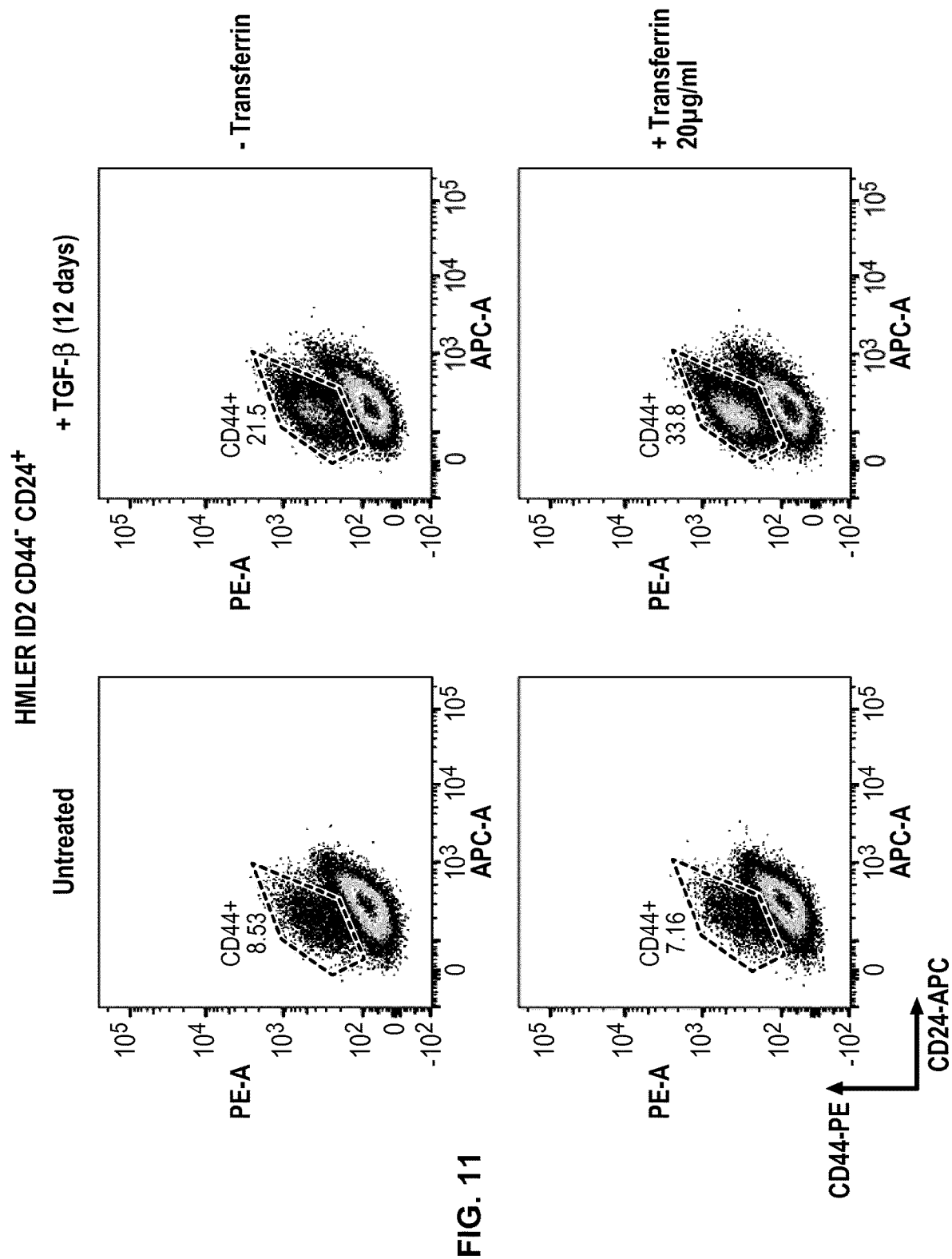

FIG. 11. Transferrin potentiates the TGF-beta-mediated induction of CD44$^{high}$CD24$^{Low/-}$ in HMLER cells. Briefly, HMLER cells were treated as indicated with TGF beta in the presence or absence of transferrin. CD44 and CD24 expression were assessed by flow cytometry. CD44$^+$ indicates the percent of CD44$^{high}$/CD24$^{Low/-}$ population gated.

FIG. 12. Sal and AM5 induce biochemical features characteristic of ferroptosis. a, Flow cytometry analysis of lipid ROS in cells treated with Sal (0.5 µM) or AM5 (0.5 µM) for 48 h. Flow cytometry analysis of 510 Annexin V-FITC (A) and Propidium Iodide (PI) fluorescence in b, HMLER CD24$^{low}$ and c, iCSCL-10A2 cells treated with Sal (0.5 µM) or AM5 (0.5 µM) for 24, 48 or 72 h. d, Primary data of the quantification of the flow cytometry analysis of e. e, Flow cytometry analysis of Annexin V-FITC (A) and Propidium Iodide (PI) fluorescence in iCSCL-10A2 cells treated with Sal (0.5 µM) or AM5 (0.5 µM) for 72 h, in the presence or absence of the indicated inhibitors. Living cells are A-/PI- and ferroptotic cells (regulated necrosis) exhibit a positive PI+ staining. Bars and error bars correspond to mean values and s.d. of two biological replicates, respectively. f, Endogenous levels of GSH in cells treated as indicated, measured as described in the Materials and Methods. Bars and error bars, mean values and s.d. of two biological replicates. *P<0.05, P<0.01, *P<0.001, ****P<0.0001, one-way ANOVA.

Figure 13:
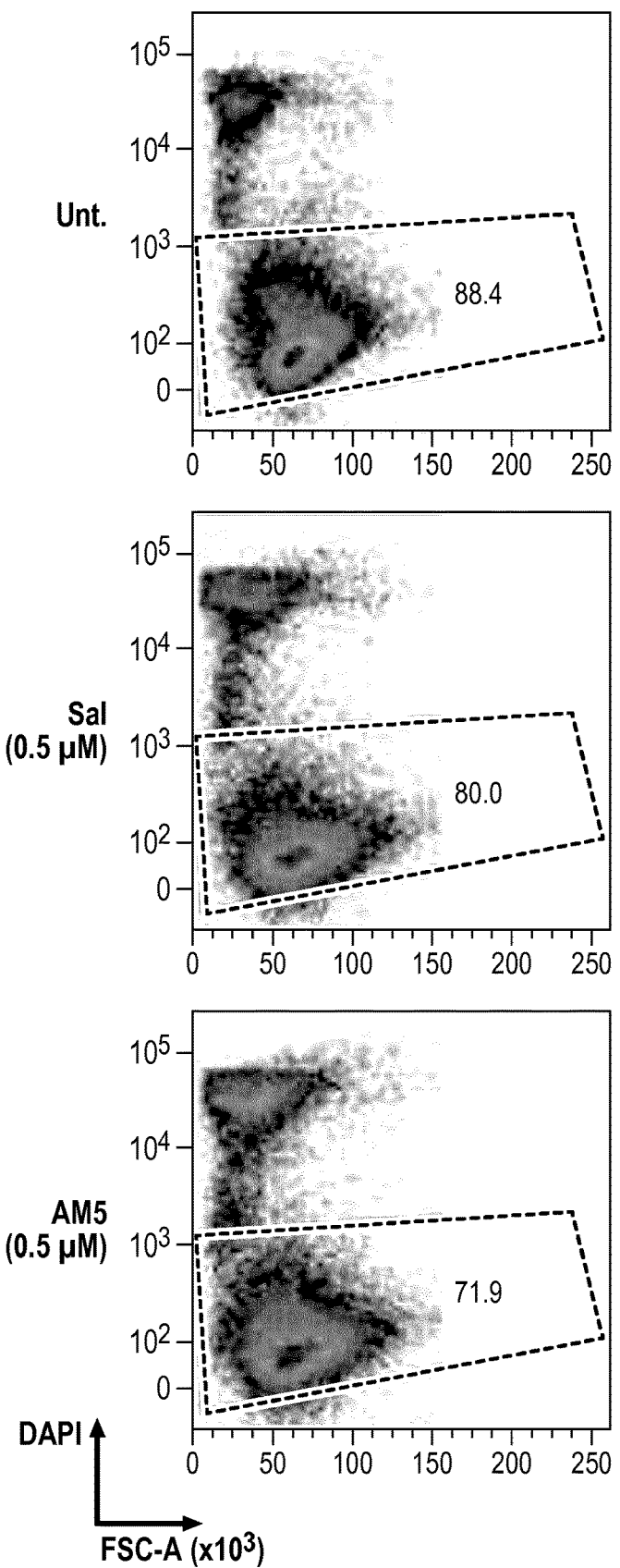
Figure 13:
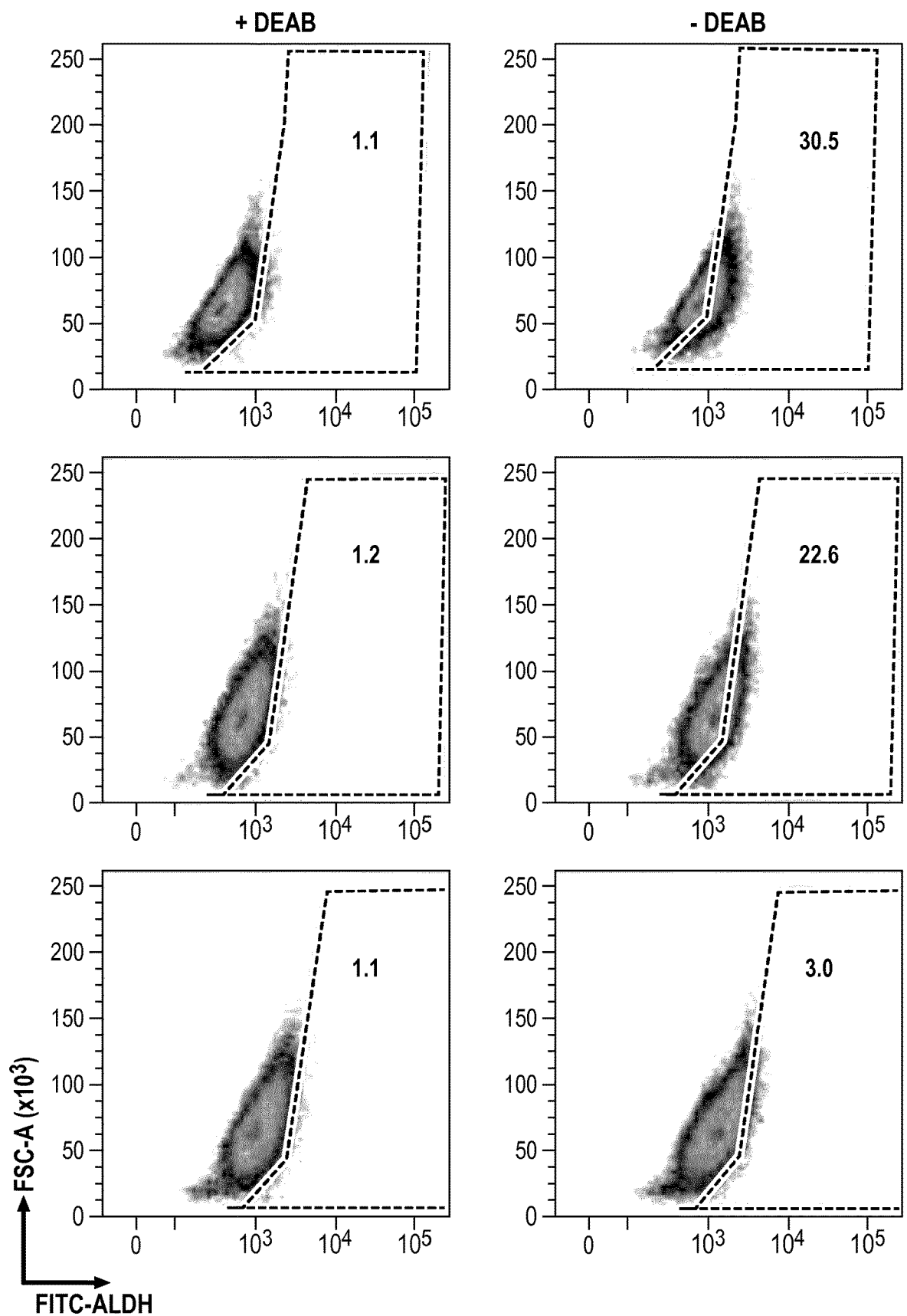

FIG. 13. Sal and AM5 effect on an ALDH+CSC cell population in vitro. Flow cytometry measurement of the effect of 0.5 µM Sal and AM5 against ALDH+ iCSCL-10A2 cell subpopulation after treated for 48 h. DEAB is the diethylaminobenzaldehyde ALDH inhibitor.

Figure 14:
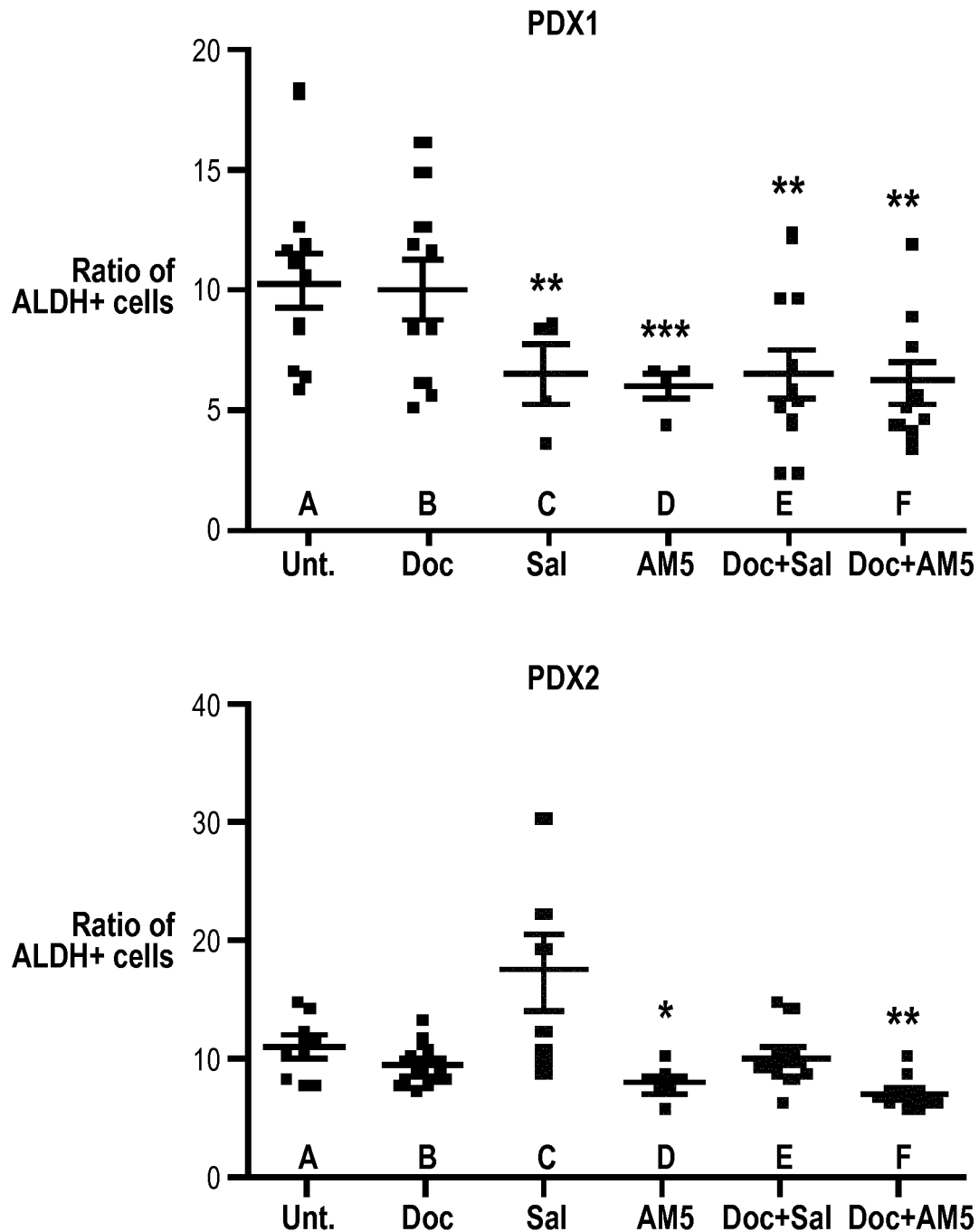

FIG. 14. Sal and AM5 alter the maintenance of CSCs in vivo in the patient derived xenograft (PDX) model. Quantification of the proportion of residual ALDH+ cells in PDX treated by means of intra-peritoneal injections (n>4 per condition per PDX in NOD/scid mice) measured by flow cytometry. Bars and error bars correspond to mean values and s.d., respectively. *P<0.05, P<0.01, *P<0.001, Student's t-test.

Figure 15:
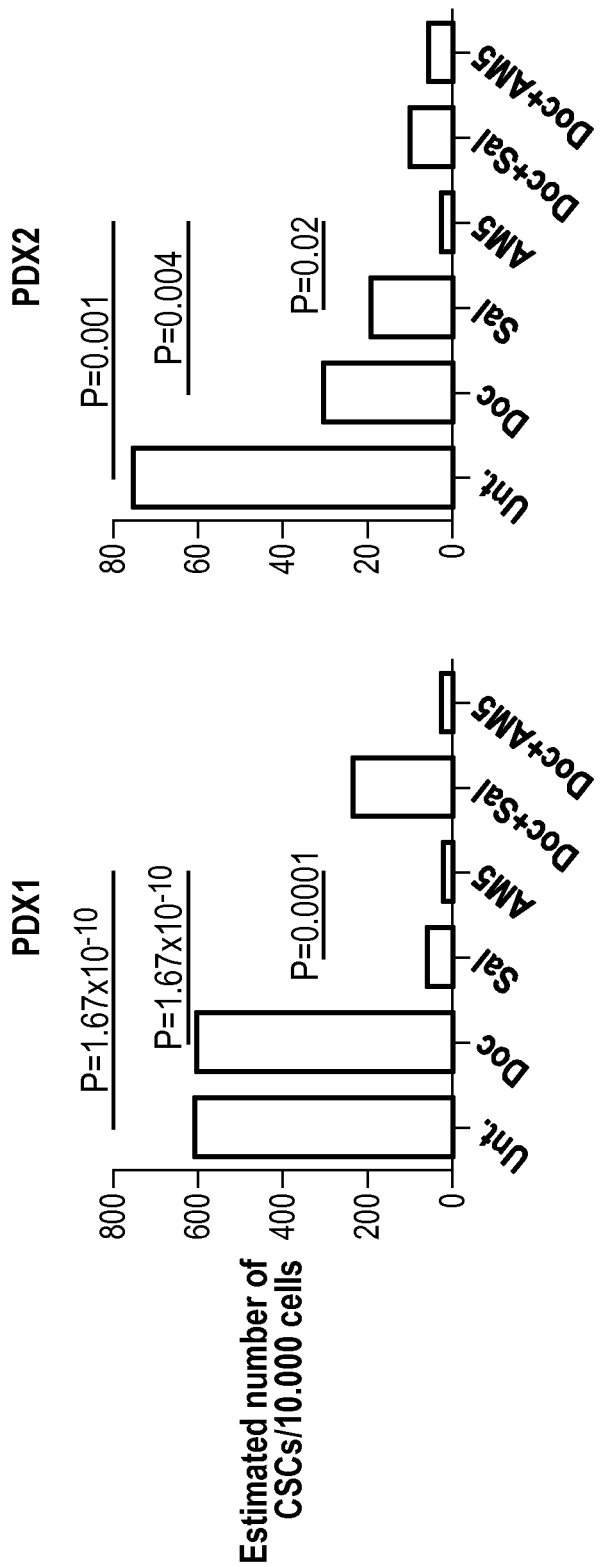

FIG. 15. In vivo antitumor effect of Sal and AM5 against PDX in nude mice. Tumor-seeding capacity of cells treated in vivo by means of intra-peritoneal injections (n>4 per condition per PDX in NOD/scid mice) and estimated number of CSCs calculated by extreme limiting dilution analysis (ELDA) software. P values, $\chi^2$ pairwise test.

Figure 16:
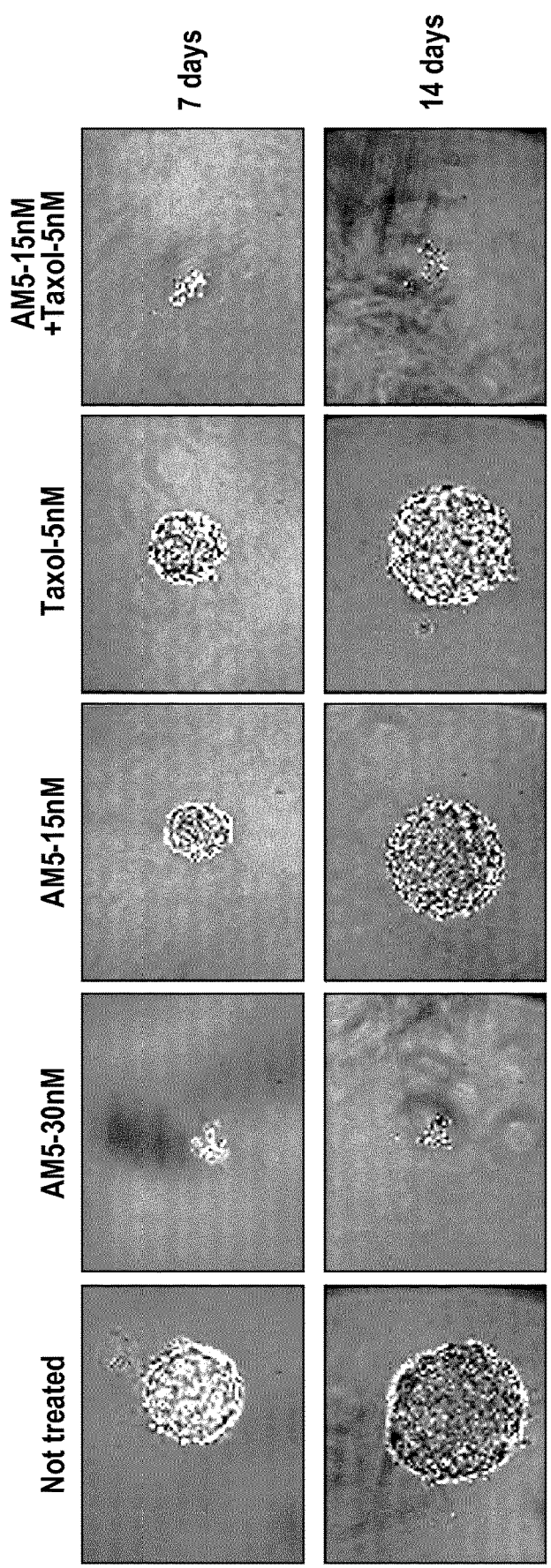
Figure 16:
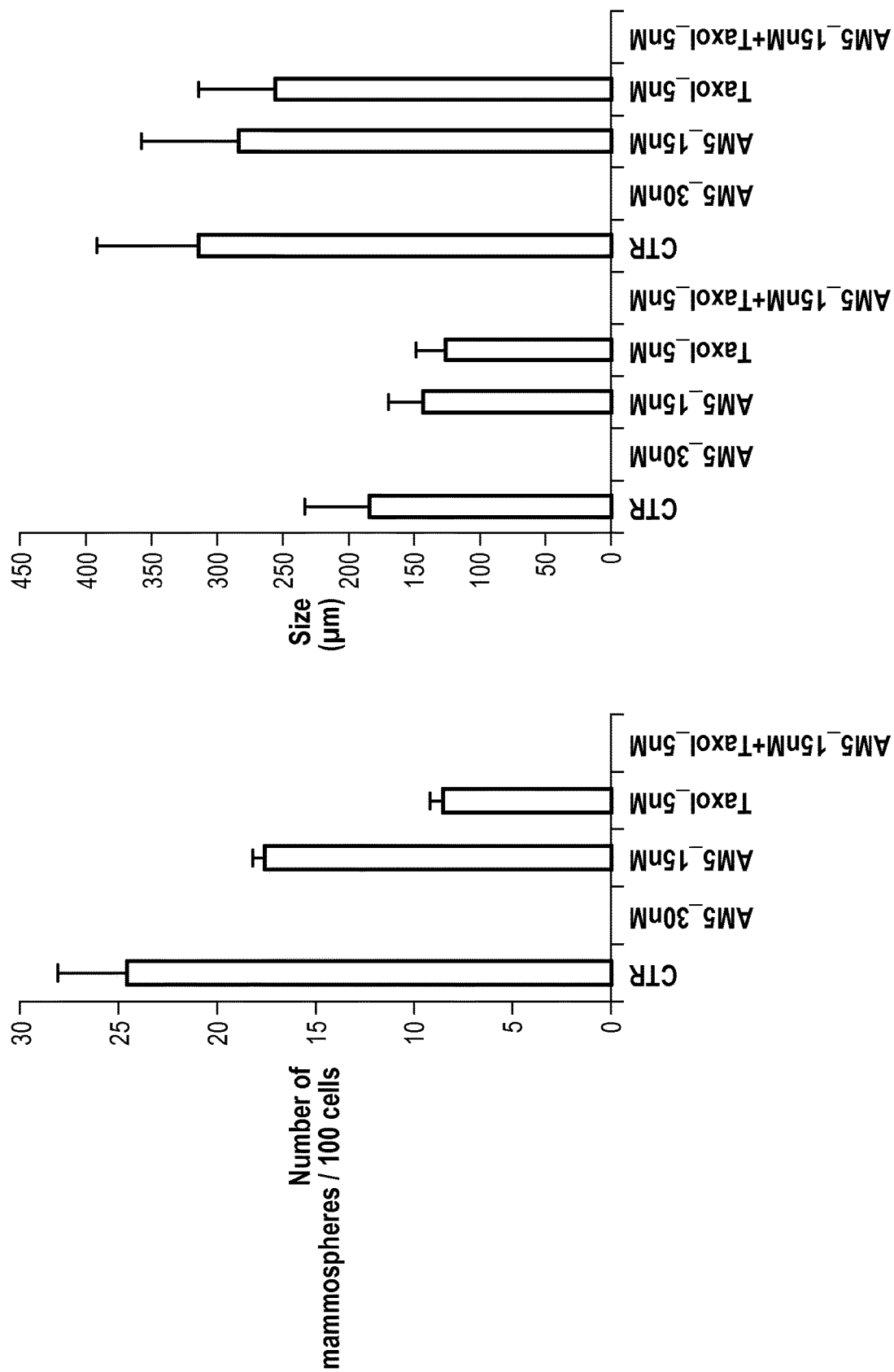

FIG. 16. Effect of AM5 and/or Taxol on mammosphere formation. a. Representative phase contrast photomicrographs of mammospheres formed after 7 or 14 days in the absence of any added compound (Not treated) or in the presence of a defined amount of salinomycin, AM5, Taxol or the combination of AM5 and Taxol. A smaller mass indicates cell death and regression of the mammosphere. b. Quantification of the number and the size of the mammospheres. The combination of AM5 at 15 nM and Taxol at 5 nM decreases the number and the size of mammospheres with a higher efficacy than AM5 alone at 15 nM or 5 nM.

EXAMPLES

Material and Methods:

Cell culture. Dulbecco's Phosphate-Buffered Saline (14190-094, 500 mL, Gibco), DMEM/F12 (31331-028, 500 mL, Gibco), DMEM high glucose with UltraGlutamine (BE12-604F/U1, BioWhittaker, Lonza), McCoy's 5A (Modified) Medium (26600-023, Gibco), RPMI 1640 with L-glutamine (BE12-702F/U1, BioWhittaker, Lonza), Fetal Bovine Serum (FBS, 10270-106, Gibco), Hydrocortisone (H0888, Sigma), Insulin (10516, Sigma or 19278, Sigma), BD human recombinant Epidermal growth factor (hEGF, 354052, BD Biosciences), PEN-STREP (DE17-602E, BioWhittaker, Lonza), Puromycin dihydrochloride (A11138-02, Life Technologies). Human osteosarcoma U2OS cell line (ATCC®, HTB-96™) was cultured in McCoy's 5A medium supplemented with 1×PEN-STREP and 10% FBS. MCF-7 (ATCC®, HTB-22™) was maintained in RPMI medium supplemented with 1×PEN-STREP and 10% FBS. The human mammary epithelial cell line infected with a retrovirus carrying hTERT, SV40 and the oncogenic allele HrasV12, named HMLER CD44$^{high}$/CD24$^{low}$ cells, not expressing E-cadherin and expressing Vimentin (referred to as HMLER CD24$^{low}$) was a generous gift from A. Puisieux (INSERM). See ref 5 of the main text. HMLER CD24$^{low}$ cells or isogenic non-stem HMLER CD24$^{high}$ cells were cultured in DMEM/F12 supplemented with 10% FBS, 10 µg/mL insulin, 0.5 µg/mL hydrocortisone, 10 ng/mL hEGF, and 0.5 µg/mL puromycin. A *mycoplasma* test was performed using PCR *mycoplasma* detection kit (G238, Applied Biological Materials).

Cell viability assay. Cell viability assay was carried out by plating 1000 cells/well in 96-well plates. Cells were treated as indicated for 72 h. CellTiter-Blue® Reagent (G8081, Promega) was added after 72 h treatment and cells were incubated for 1 h before recording fluorescence intensities (Excitation, 560/20 nm; Emission, 590/10 nm) using a Perkin Elmer Wallac 1420 Victor2 Microplate Reader.

Clonogenic assay. HMLER CD24$^{low}$ cells were plated in 6-well plates and incubated with various concentrations of Sal and derivatives for 72 h. Single-cell suspensions were mixed with an equal volume of 0.7% soft agar and plated in 6-well plates (2500 cells/well) for 10 days. After staining with 3-(4,5-dimethyl-2-thiazolyl)-2,5-diphenyl-2H-tetrazolium bromide (MTT, M2128, Sigma). Colonies with a diameter of more than 0.5 mm were counted.

Chemical labeling of Sal derivatives and fluorescence microscopy. U2OS cells were cultured at ~80% confluence and were treated for 6 h with 2 M compounds unless stated otherwise. LysoTracker® Deep Red (L12492, Molecular Probes®) and MitoTracker Red CMXRos (M7512, Molecular probes) were added 1 h prior cell fixation. Cells were fixed 12 min with 2% PFA/PBS, washed with PBS and permeabilized for 10 min with 0.1% Triton X-100/PBS, then washed three times with 1% BSA/PBS. Methanol fixation was used instead of formaldehyde fixation for specific antibodies according to the manufacturer protocol. Briefly, cells were incubated in absolute methanol (HPLC grade) at −20° C. for 15 min prior permeabilization. The click reaction cocktail was prepared from Click-iT® EdU Imaging kits (C10337, Life Technologies) according to the manufacturer's protocol. Briefly, mixing 430 µL of 1× Click-iT® reaction buffer with 20 µL of $CuSO_4$ solution, 1.2 µL Alexa Fluor® azide, 50 µL reaction buffer additive (sodium ascorbate) to reach a final volume of ~500 µL. Cover-slips were incubated with the click reaction cocktail in the dark at RT for 30 min, then washed three times with PBS. For immunofluorescence, cells were blocked with 5% BSA, 0.2% Tween-20/PBS (blocking buffer) for 10 min at RT. Cover-slips were incubated with 100 µL of diluted primary antibodies in blocking buffer (e.g., ERp72, RCAS1, LC3, Ferritin) overnight at 4° C. Cover-slips were then washed three times with blocking buffer and incubated as described above with the appropriate secondary antibodies for 30 min. Cover-slips were washed three times with PBS and mounted using Vectashield Mounting Medium with DAPI (H-1200, VECTOR Laboratories). High resolution fluorescence images were acquired using a Deltavision real-time microscope (Applied Precision). 60×/1.4NA and 100×/1.4NA objectives were used for 2D and 3D acquisitions that were deconvoluted using SoftWorx software (Ratio conservative—15 iterations, Applied Precision). ImageJ was used for further image processing.

Tumorsphere assay. HMLER CD24$^{low}$ cells were plated as single-cell at $10^3$ cells/mL in ultra-low attachment culture dishes using serum-free DMEM/F12 supplemented with B-27 (17504044, Invitrogen, 1:50), 20 ng/mL hEGF, 4 µg/mL insulin and 0.5 µg/mL hydrocortisone. After 7 days, tumorspheres were enzymatically dissociated with 0.05% trypsin (15090, Gibco) for 15 minutes at 37° C. to obtain a single-cell suspension. Sphere formation was assessed 7 days after seeding cells individually in 96-well ultralow attachment plates (Corning), which were treated as indicated. The number and the size of tumorspheres were analyzed under a light microscope.

Xenograft tumor formation experiments. MCF-7 cell cultures were collected, enzymatically dissociated, washed with PBS, and re-suspended in a PBS/Matrigel mixture (1:1 v/v). The mixture (0.1 mL) was then implanted in the mammary fat pad of 5-week-old female AthymicNude-Fox1nu mice bilaterally (Harlan, France). Mice were maintained in individually-ventilated cages (Tecniplast, France) under constant temperature and humidity. All experiments were performed under laminar flow (Tecniplast France). Mice received estradiol supplementation (0.4 mg/kg) the same day and 7 days from cell injection, and were observed and palpated for tumor appearance. Mice were treated with AM5 (3 mg/kg body weight/day) by means of intraperitoneal injections every 5 opened days of the week. Tumor growth was measured weekly using calipers. Tumor volume was determined using the standard formula: $L \times W^2 \times 0.52$, where L and W are the longest and shortest diameters, respectively. All animal studies were approved by the Direction des services Vétérinaires, Prefecture de Police, Paris, France (authorization number A75-14-08) and the ethical committee (number 34) of Paris Descartes University. No randomization was used and experimenters were blinded to drug treatments and tissue analyses.

Patient derived xenografts (PDXs). PDXs were established as previously described in Charafe-Jauffret et al., Cancer Res. 73, 7290-7300 (2013) from tissue samples collected prospectively at the Institut Paoli-Calmettes (IPC). Samples of human origin and associated data were obtained from the IPC/CRCM Tumor Bank that operates under authorization #AC-2007-33 granted by the French Ministry of Higher Education and Research. Before scientific use of samples and data, patients were appropriately informed and asked to consent in writing, in compliance with French and European regulations. The project was approved by the IPC Institutional Review Board. Cells from 2 different patient-derived xenografts (PDX 1 and 2) were transplanted orthotopically into fat pads of 4-week-old female non-obese diabetic/severe combined immunodeficient (NOD/SCID) mice (NOD.CB17-Prkdcscid/J, Charles River France) after mechanical treatment and enzymatic digestion using collagenase/hyaluronidase (StemCell Technologies) to generate single-cell suspension suitable for implantation in vivo. PDXs were primarily established as previously described in Caraft-Jauffret et al., and evaluated for ALDEFLUOR-positive CSCs. We injected single cancer cells into fat pads of NOD/SCID mice and monitored tumor growth. When tumor size reached approximately 150 $mm^3$, Sal and AM5 treatments were performed as indicated above for FIGS. 14 and 15. Tumor growth was compared with that of docetaxel and placebo-treated controls. After 4 weeks of treatment, the animals were sacrificed and the proportion of ALDE-FLUOR-positive CSCs was measured in each residual tumor. All animal studies were approved by the French Ministry of Higher Education and Research (authorization number D130554) and ethical committee (number 14), of Aix-Marseille Université. No randomization was used and experimenters were blinded to drug treatments and tissue analyses.

Aldefluor assay. The analysis was processed on single-cell suspension from the PDXs obtained as described above. The ALDEFLUOR Kit (Stemcell™ Technologies) was used to isolate the population with high aldehyde dehydrogenase enzymatic activity using an LSR2 cytometer (Becton Dickinson Biosciences), as previously described in Charafe-Jauffret et al. To eliminate cells of mouse origin from the PDXs, we used staining with an anti-H2Kd antibody (BD Biosciences, 1:200, 20 min on ice) followed by staining with a secondary antibody labeled with phycoerythrin (PE; Jackson Laboratories, 1:250, 20 min on ice).

Limiting dilution assay. Cells from 4-week treated mice were re-implanted into one to four secondary NOD/SCID mice with injection of 10, 50, 500 or 5000 cells for each treated tumor to functionally evaluate the proportion of residual CSCs in each treatment group (Unt., Doc, Sal, AM5) for the PDX 1 and 2. Each mouse that developed a tumor reaching a size of 10 mm was considered as a tumor-bearing mouse.

Estimation of number of CSCs in vivo. The number of mammary gland outgrowths obtained in a fat pad after cell re-implantation is currently used to evaluate the number of stem cells able to repopulate this fat pad. It is based on self-renewal and differentiation abilities, two hallmarks of stem cells. In the same manner, estimation of the number of CSCs can be obtained from tumor outgrowth data collected after limited dilution re-implantation of each group of treatments, based on tumor-initiating capacities of CSCs. For calculation, an online tool is available using Extreme Limiting Dilution Analysis (ELDA) (http://bioinf.wehi.edu.au/software/elda/) for limiting dilution analysis based on the Poisson single-hit model according to the number of outgrowths observed and the number of pat pad re-implanted for each cell dilution.

Histology. Organs from mice were removed at time of sacrifice. For morphological analyses, organs were fixed with 4% paraformaldehyde, paraffin embedded, and 4-μm sections were stained with hematoxylin and eosin (H&E). Sections were scanned at high resolution using a slide scanner (NanoZoomer 2.0-HT, Hamamatsu, Massy, France).

Localization of intracellular iron(II). RhoNox-1 was synthesized according to the original procedure described in Naujokat and Steinhart, J. Biomed. Biotechnol. 2012. Cells were seeded on p-Dishes, then treated as indicated in FIG. 1. Cells were washed with 1× Hank's Balanced Salt Solution (HBSS, 14025-092, Life technologies) three times, then incubated with 5 μM of RhoNox-1/HBSS for 1 h at 37° C., 5% $CO_2$ and washed with HBSS. Co-staining was performed by adding 100 nM LysoTracker Deep Red and Hoechst 33342 (H1399, Sigma, final concentration of 1 μg/mL) in HBSS. Experiments were performed with a 60×APO TIRF oil immersion objective of Nipkow Spinning Disk confocal system.

Immunoblotting. Cells were treated as indicated, then washed twice with PBS and lysed with 2× Laemmli buffer. Cell extracts were heated at 95° C. for 5 min, sheared through a 26-gauge needle and quantified with a Nanodrop 2000 (Thermo Scientific). Protein lysates (~100 μg) were resolved by SDS-PAGE electrophoresis and transferred onto PVDF membranes (Amersham). Membranes were blocked with 5% BSA, 0.1% Tween-20/TBS for 1 h. The blots were then probed with the relevant primary antibodies in 5% BSA, 0.1% Tween-20/TBS at 4° C. overnight with gentle agitation. Membranes were washed with 0.1% Tween-20/TBS for 30 min and were incubated with secondary antibodies for 1 h at RT. Antigens were detected by ECL (Amersham). Imaging was performed using a ChemiDoc™ XRS+ System (Biorad).

Perl's reaction. Tumors from mice were removed at time of sacrifice. Tumors were fixed with 4% PFA and embedded in paraffin. To monitor accumulation of ferric iron, 4-μm sections were processed for standard Prussian blue staining. Briefly, slides were deparaffinized in xylenes, rehydrated through a graded ethanol series, and subjected to a 1:1 potassium ferrocyanide solution (2%)/hydrochloric acid solution (2%) for 20 min. Then, slides were washed with distilled water (5 min). Nuclear fast red solution was used to stain nuclei. Images were acquired by light microscopy using an inverted microscope (Eclipse Ti—S, Nikon) and 10×/0.30, 20×/0.50 or 40×/0.785 Plan Fluor objectives (Nikon). Images were captured using a Super high definition cooled colour camera head DS-Ri1 (Nikon) and NIS Elements software (Nikon).

This allows the detection of iron III in tumor tissue.

Lysosomal membrane permeabilization assay. Lysosomal membrane permeabilization (LMP) was assessed by monitoring the release of FITC-Dextran (FD10S, 10 kDa, Sigma) from lysosomes. In brief, cells were incubated with 1 mg/mL FITC-Dextran for 2 h at 37° C. Cells were washed, chased with culture medium for 2 h and treated as indicated for 48 h or with CQ (positive control) for 3 h. Cells were then fixed with 2% formaldehyde/PBS, washed with PBS, mounted and acquired with a 60×APO TIRF oil immersion objective of Nipkow Spinning Disk confocal system.

Annexin V/PI assay. Cells were treated as indicated. After treatment, cell death was quantified using Annexin V-FITC/Propidium Iodide (PI) assay according to the manufacturer's protocol (FITC Annexin V Apoptosis Detection Kit II, 556570, BD Pharmingen™) and analyzed by a LSR-Fortessa™ flow cytometer (BD Bioscience, San Jose, Calif.). The data were processed using Cell Quest software (BD Biosciences).

Lipid ROS measurements. Cells were treated with Sal or AM5 (0.5 μM) as indicated. Then, cells were trypsinized and washed with PBS. Subsequently, cells were incubated with Bodipy-C11® (D3861, Thermo Fisher Scientific, 2 μM) at 37° C. for 60 min. Next, cells were washed twice with PBS. Oxidation of Bodipy-C11 resulted in a shift of the fluorescence emission peak from 590 nm to 510 nm proportional to lipid ROS generation that was analyzed by LSRFortessa™ flow cytometer (BD Biosciences, San Jose, Calif.). The data were processed using Cell Quest software (BD Biosciences) and FlowJo software (FLOWJO, LLC). For cell imaging, cells were treated as indicated in the main figure (Bodipy-C11®, 1 μM, 1 h), then fixed with formaldehyde (2% in PBS, 12 min) and analyzed by fluorescence microscopy (ex. 488 nm).

Intracellular GSH level quantification. Cells were treated with Sal or AM5 (0.5 μM) as indicated, then harvested and counted. The intracellular GSH level was measured using a commercial kit (ab205811, Abcam) according to the manufacturer's protocol.

RhoNox-1 reduction assay. Experiments were carried in 96-well plate dishes. Reagent stock solutions were freshly prepared using Milli-Q water. 50 μL of solutions of Sal (800 μM), DFO (800 μM) and $FeSO_4$ (80 μM) were mixed prior to addition of 50 μL of RhoNox-1 (40 μM) and completed with the appropriate volume of water to reach a final volume of 200 μL per well. Measurements were performed 30 min after addition of RhoNox-1 to the mix and were recorded using the PARADIGM™ Microplate Detection Platform (ex. 492 nm; em. 580 nm).

Electrothermal atomic absorption spectrometry. Cells were harvested, the supernatant was removed, cell pellets were dried and mineralized by adding 100 μL of concentrated nitric acid (PlasmaPure® 67-69% $HNO_3$, SCP Science, Baie-d'Urfé, Canada) at 80° C. and further diluted with 400 μL of ultrapure water (Milli-Q®, Millipore, Molsheim, France). Iron was determined in cell mineralizates by means of Electrothermal Atomic Absorption Spectrometry (ETAAS) on a PinAAcle® 900Z spectrometer (Perkin Elmer, Les Ulis, France). This method allows the quantification of cellular iron (total iron).

Small interfering RNA transfection. Suitable small interfering RNAs (siRNA) were designed with the Qiagen RNA interference designer tool for specific down-regulation of FTH1. The sequence used for FTH1 was 5'-GUCCAUGU-CUUACUACUUUTT-3' (S100300251) targeting the sequence following 5'-CTGTCCATGTCTTACTACTTT-3' and a negative control siRNA for FTH1 (5'-CAUUAGUUUGGGCAGUAUAUTT-3', (S103089212). Subconfluent cells were transfected with siRNA in Opti-MEM using the Oligofectamine™ reagent (Invitrogen) for 48 h. Then, cells were treated with OSM (100 ng/mL for 48 h) prior to protein or RNA extraction and flow cytometry analysis for markers as indicated.

Statistical analysis. Data were compared using a two-tailed Student's t-test or a one-way ANOVA as indicated. Data are presented as mean values. Two groups were considered to be significantly different if P<0.05.

Example 1: Lysosomal Iron Localization

Figure 1B:
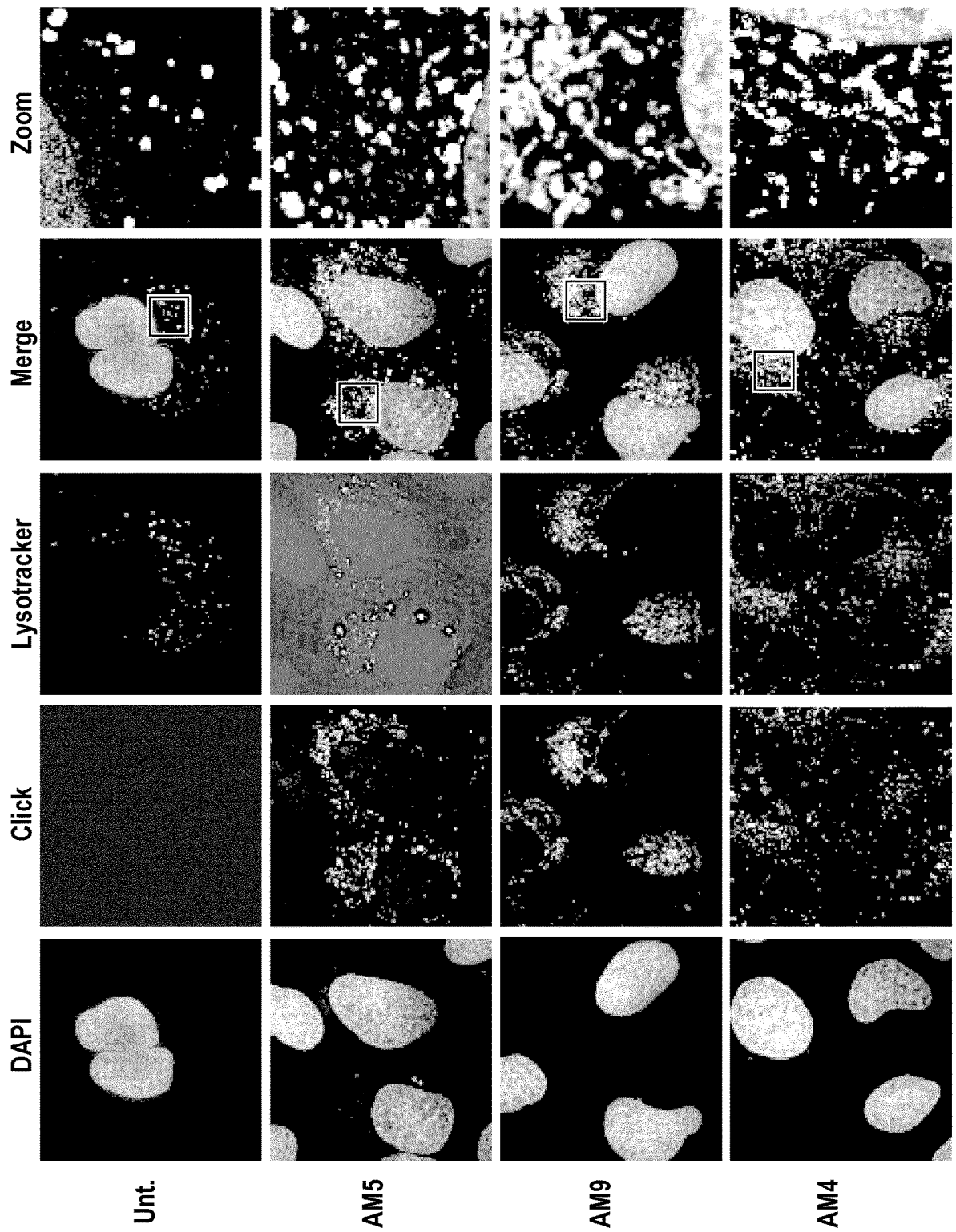

The inventors functionalized alkynes in cells by means of in situ click chemistry to detect otherwise invisible compounds, a strategy virtually applicable to any molecule (FIG. 1a). Sal surrogates co-localized with a marker of lysosome in U2OS cells, demonstrating that these compounds physically accumulated in the lysosomal compartment irrespective of the overall charge and without altering the lysosomal pH (FIG. 1b).

Figure 1C:
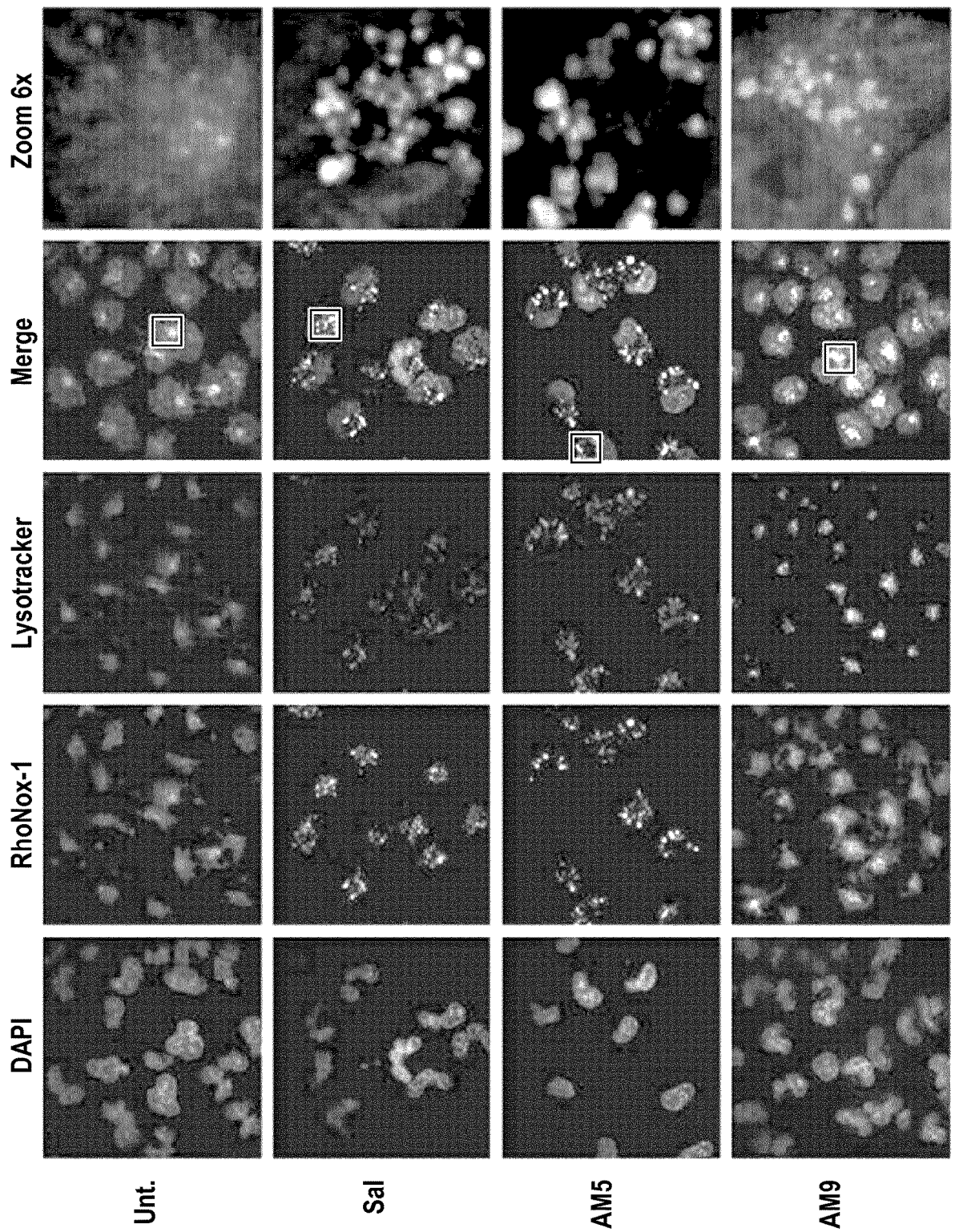
Figure 1D:
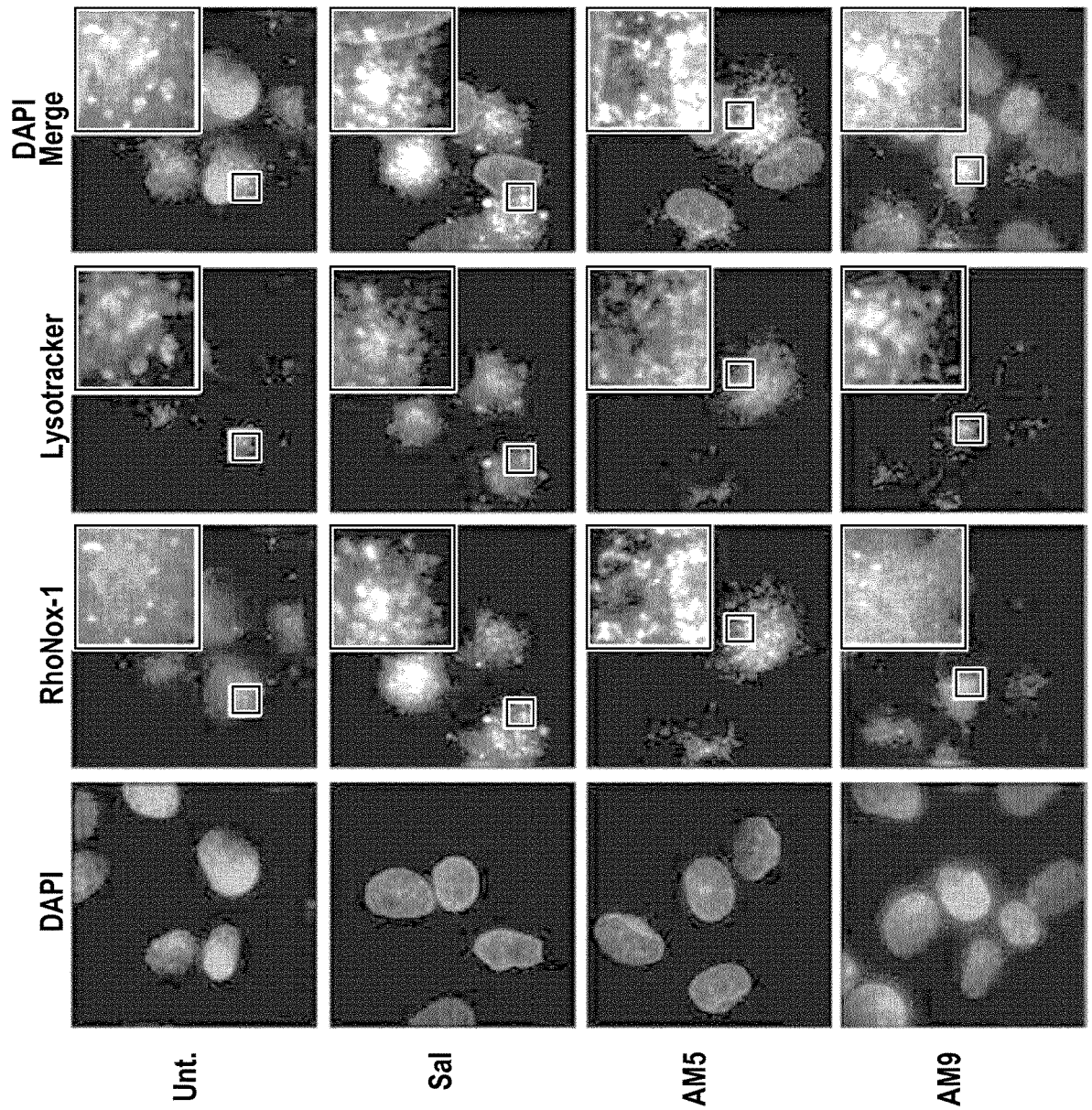
Figure 1E:
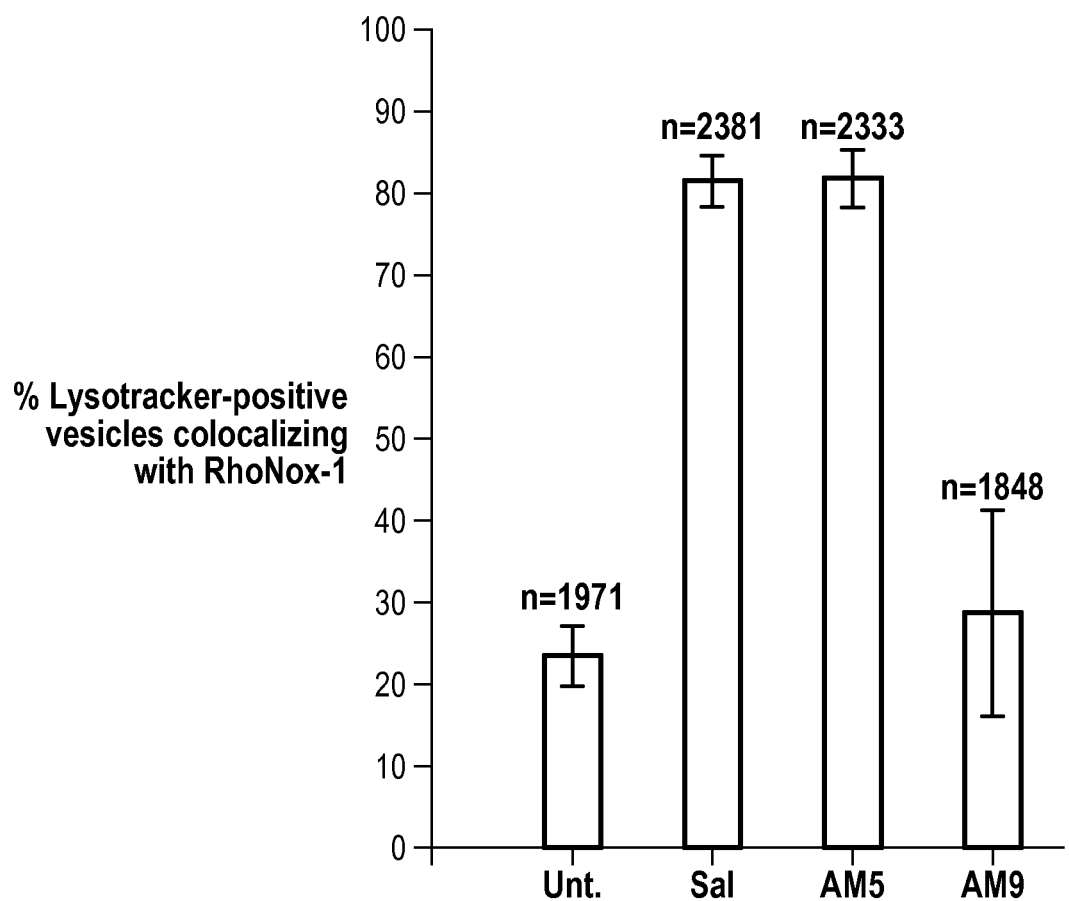
Figure 1F:
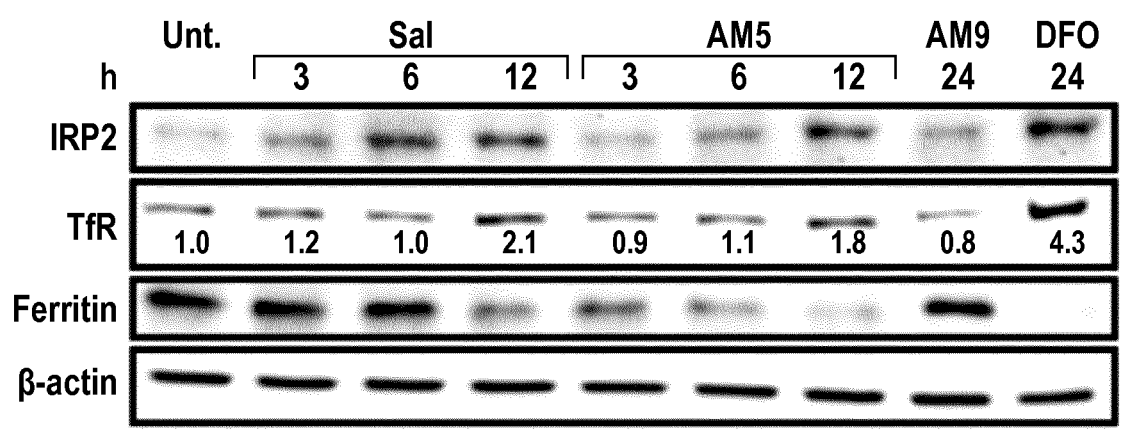
Figure 1G:
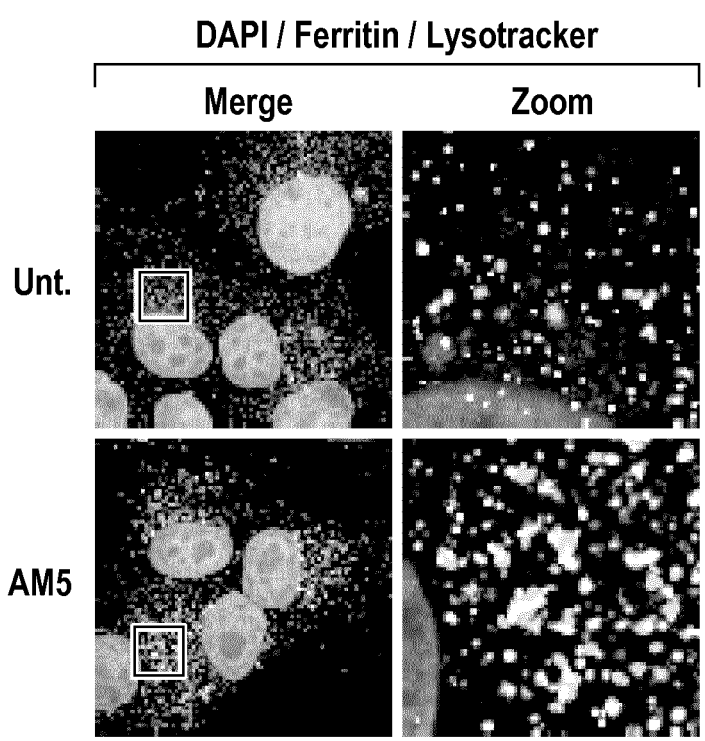

In particular, the closely related derivative AM4, devoid of a protonable amine, also accumulated in lysosomes lending strong support to the notion that Sal targets lysosomes. In comparison, AM5 did not target the other organelles studied. Since Sal can interact with alkali metals, and given that intracellular iron is tightly regulated and transits through the lysosomal compartment, we explored the effect of Sal on iron homeostasis starting with the subcellular localization of iron(II) using the specific RhoNox-1 fluorogenic probe. While the staining of iron(II) was diffuse in both untreated HMLER CD24$^{low}$ cells and in cells treated with AM9, treatment with Sal or AM5 led to a staining that was restricted to the lysosomal compartment (FIG. 1c and FIG. 1d). Indeed, approximately 80% of lysotracker-positive vesicles (e.g. lysosomes) colocalized with the RhoNox-1 probe following treatment with Sal or AM5, whereas only 20-30% of lysotracker-positive vesicles showed colocalization following treatment with AM9 or no treatment (FIG. 1e). Thus, Sal and AM5 sequester iron in lysotracker-positive vesicles (i.e. lysosomes). Treatment with Sal and AM5 also induced a response characteristic of a cytosolic depletion of iron, including increased levels of iron-responsive element-binding protein 2 (IRP2) and transferrin receptor (TfR) along with reduced levels of ferritin (FIG. 1f). A similar response was also observed when cells were treated with the iron(III) chelator deferoxamine (DFO).

Figure 1H:
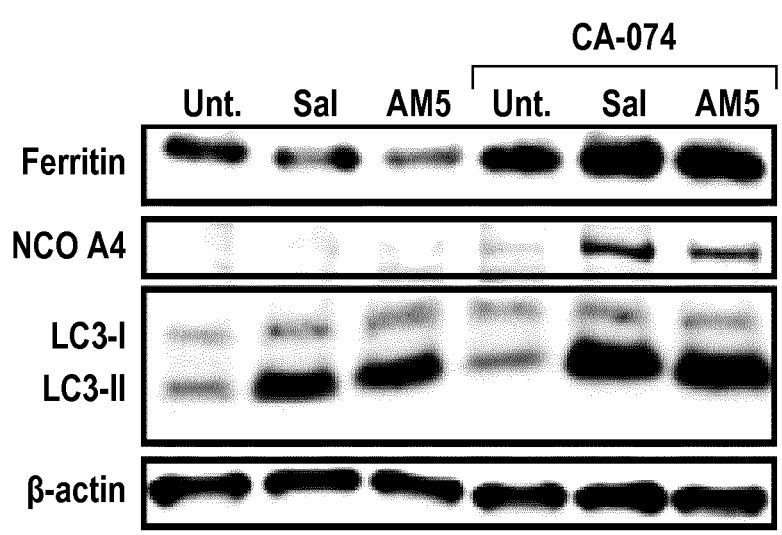
Figure 1I:
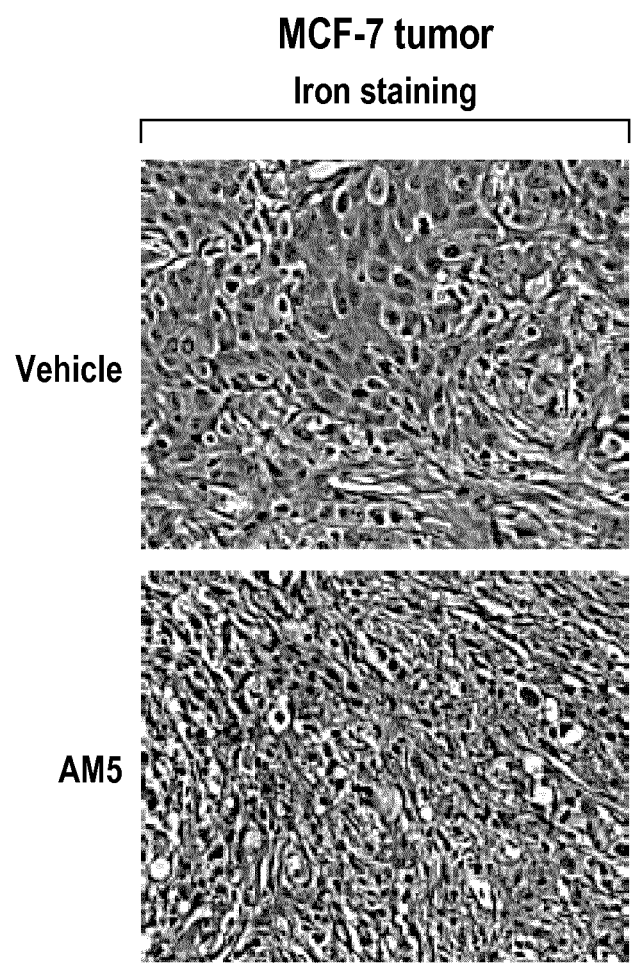
Figure 1J:
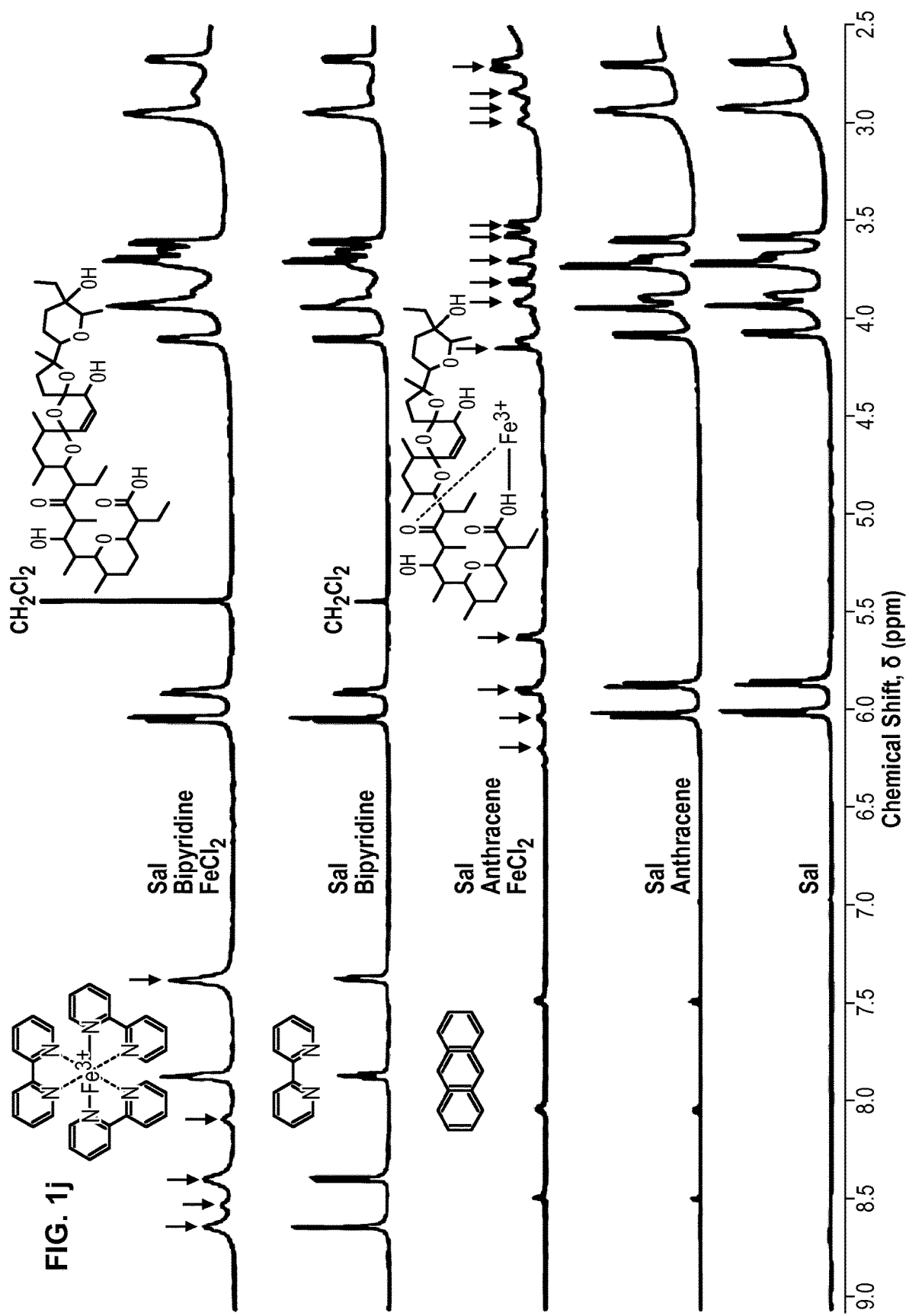
Figure 1K:
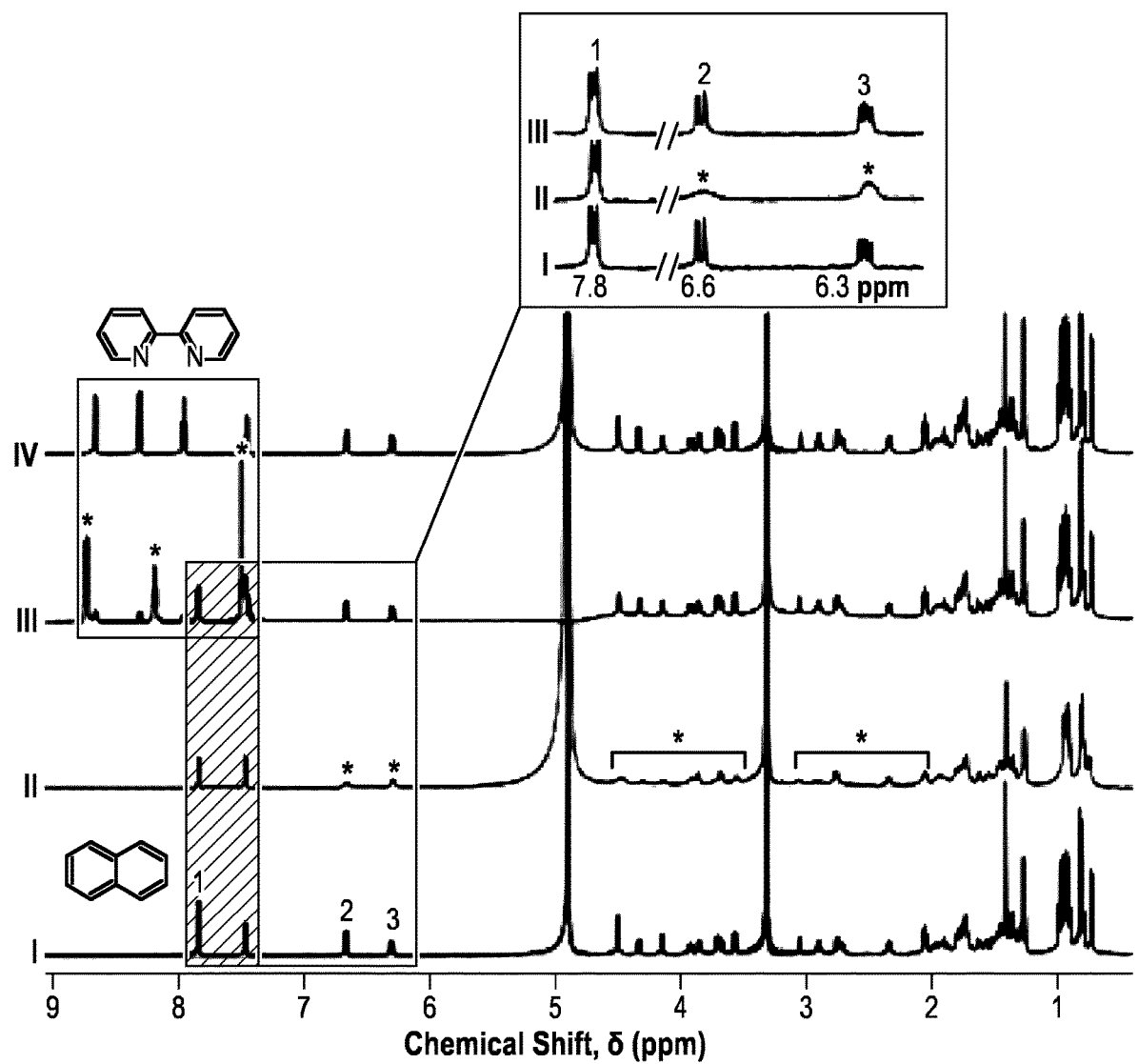
Figure 1I:
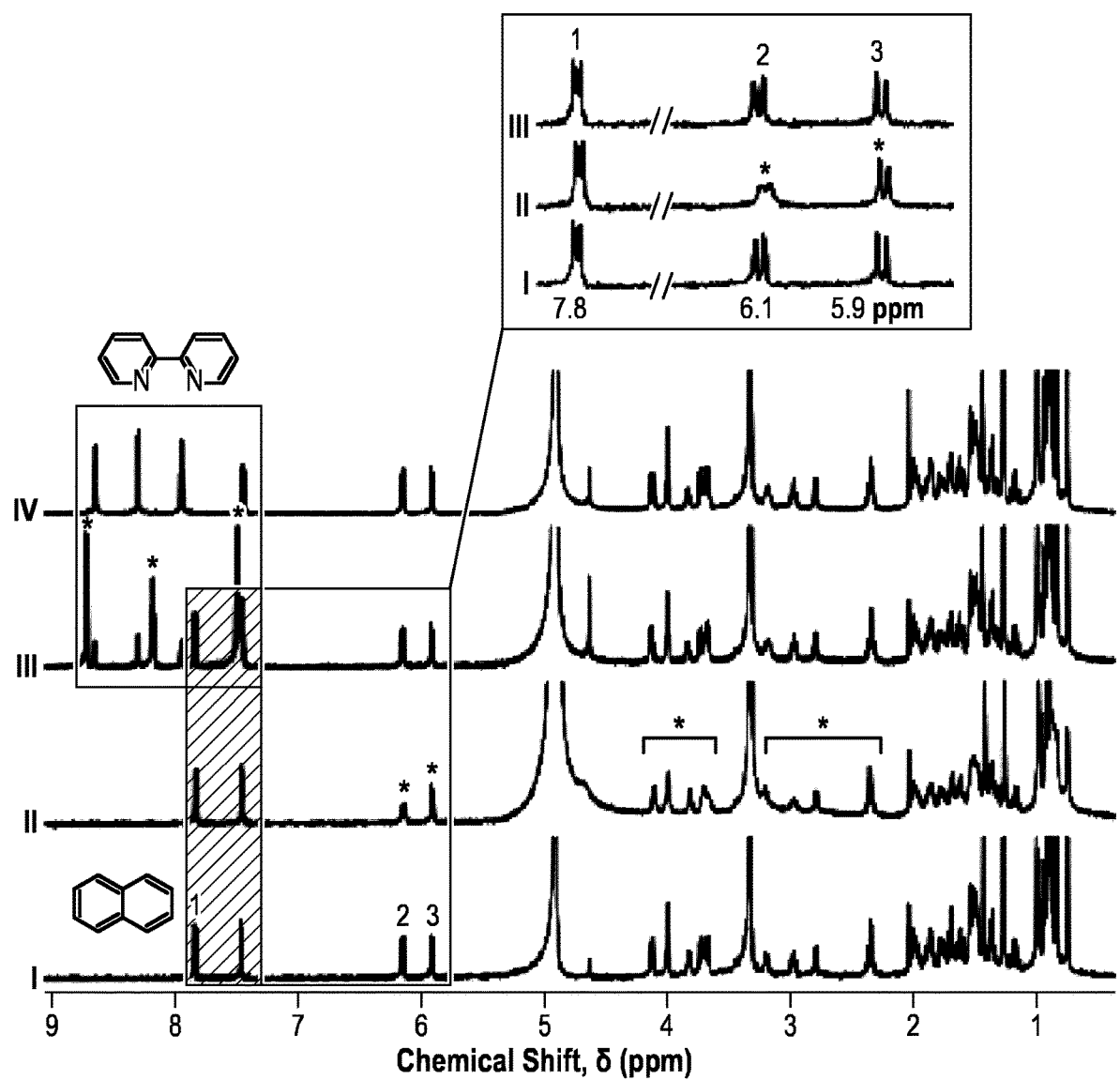

These results were consistent with the idea that Sal prevented the release of iron(II) from lysosomes. Remarkably, AM5 promoted a re-localization of ferritin to the lysosomal compartment (FIG. 1g), whose degradation was prevented by pharmacological inhibition of the lysosomal protease cathepsin B using CA-074 (FIG. 1h). The protein NCOA4 has been identified as a cargo receptor of ferritin and is required for its degradation by a selective form of autophagy named ferritinophagy. In strong agreement with the notion that Sal and AM5 activated ferritinophagy, NCOA4 could be detected by western blotting when cells were treated with these drugs in conjunction with an inhibitor of cathepsin B (FIG. 1h). Additionally, Sal and AM5 increased the level of autophagy marker protein LC3-II, which was more pronounced upon inhibition of cathepsin B (FIG. 1h), and ferritin co-localized with LC3 in cells co-treated with AM5 and CA-074 (data not shown). Furthermore, the accumulation of iron(III) in MCF-7 tumors treated with AM5 reflected a cellular response to the targeting of iron homeostasis (FIG. 1i). In line with Sal interacting with iron(II) in cells, nuclear magnetic resonance (NMR) revealed that proton signals of Sal were shifted upon titration with iron(II), whereas signals of the internal standard anthracene remained unaffected, demonstrating that Sal interacted with iron(II) ex cellulo. Conversely, the presence of bipyridine as a competitor prevented Sal from interacting with iron(II) (FIG. 1j). NMR further revealed that addition of 0.5 mol equiv. of $FeCl_2$ to a methanolic solution of AM5 induced broadening and flattening of specific proton signals (FIG. 1k), including that of the C18-C19 vinylic protons at 6.6 and 6.3 ppm. This data, characteristic of the effect of a paramagnetic metal on the relaxation of protons in close proximity, indicated interactions between AM5 and iron(II) in solution. Interestingly, previous X-ray crystallography studies have revealed that the vinylic protons are topologically close to the sodium ion inside the cavity formed by Sal around the metal in a co-crystal. Thus, the pronounced effect of iron(II) onto the signals of these two protons suggested that iron(II) may occupy a similar position inside the folded molecule. The sub-stoichiometric amount of $FeCl_2$ required to promote this effect was consistent with a 2:1 AM5:iron(II) stoichiometry. However, this data could also reflect a time-averaged set of signals between bound and free AM5, indicating a fast exchange that cannot be resolved within the timescale of the NMR experiment. In comparison, the proton signals of naphthalene (Napht), an organic small molecule devoid of heteroatoms and therefore unable to chelate iron, remained unaffected, and thus could be used as internal standard (e.g. unaltered signal at 7.8 ppm) to compare the intensity of signals of AM5 between samples. Strikingly, addition of a slight excess of the iron(II) chelator 2,2'-bipyridine (Bipy) to a mixture of AM5, Napht and $FeCl_2$, led to the occurrence of new proton signals of free and bound Bipy along with the concomitant rescue of the signals previously observed for the unbound AM5. These data indicated that under these conditions, Bipy displaces the metal from AM5, in line with the fact that AM5 is a looser iron interacting partner compared to Bipy. It is noteworthy that a similar trend was observed for Sal (FIG. 1l), although the shielding effect of iron(II) was more pronounced on the proton signals of AM5. Moreover, while iron(II) promoted the formation of byproducts of Sal over time, AM5 was found to be stable under these conditions. These properties of AM5 provides a rationale for the higher potency of this synthetic derivative compared to Sal.

Altogether, these data supported a model whereby the lipophilic natural product accumulated in the lysosomal compartment and interacted with iron, thereby preventing release of the metal into the cytosol and initiating the appropriate response to replenish the available pool of iron.

Example 2: Iron Concentration, Iron Chelation and Iron Related Biomarkers

Iron can catalyze the production of reactive oxygen species (ROS) via Fenton chemistry. Treatment of U2OS, HMLER CD24$^{low}$, and iCSCL-10A2 cells with Sal and AM5 led to a significant increase in lysosomal ROS in all cell lines, which mirrored the accumulation of iron in this organelle (data not shown).

Figure 12A:
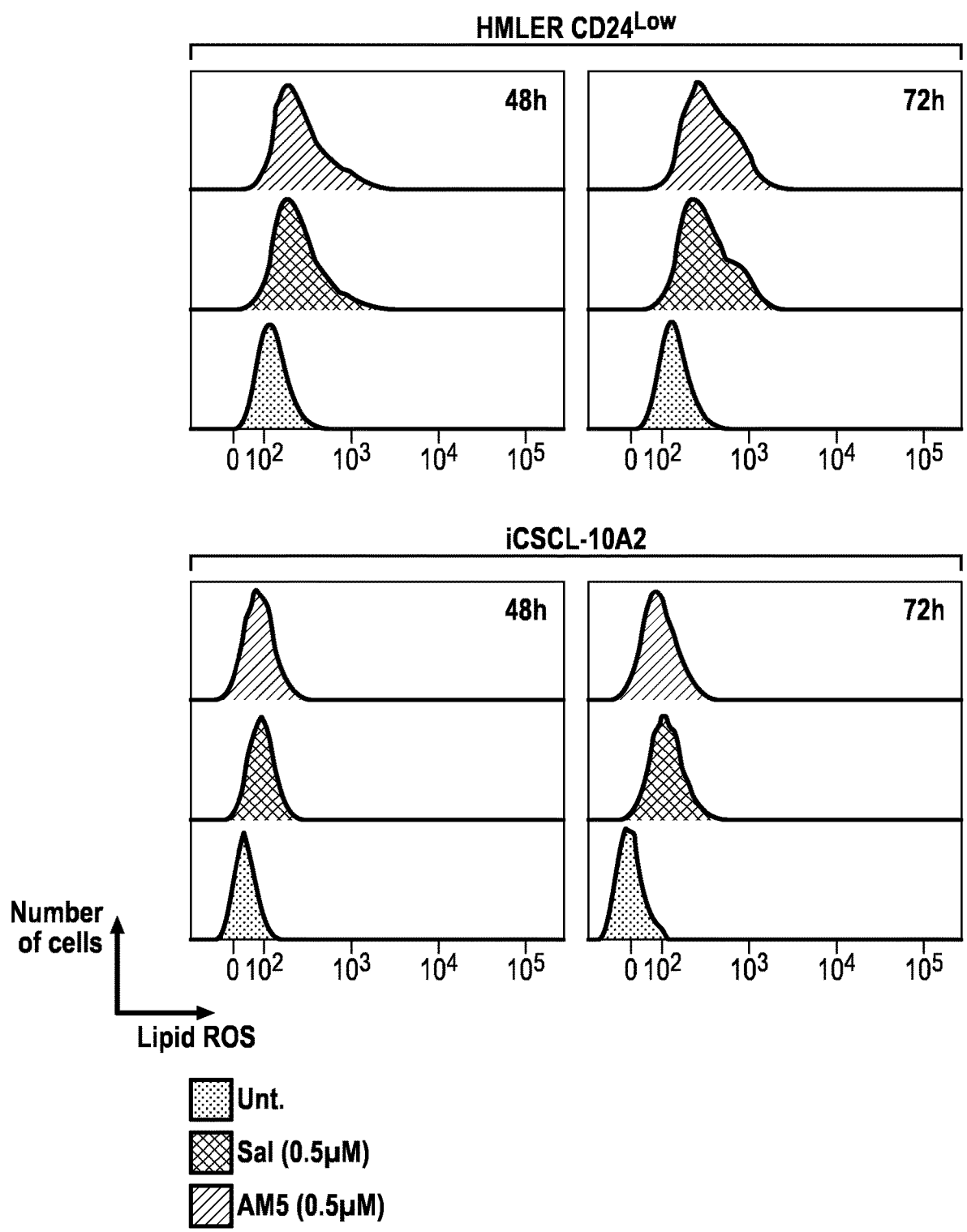
Figure 12D:
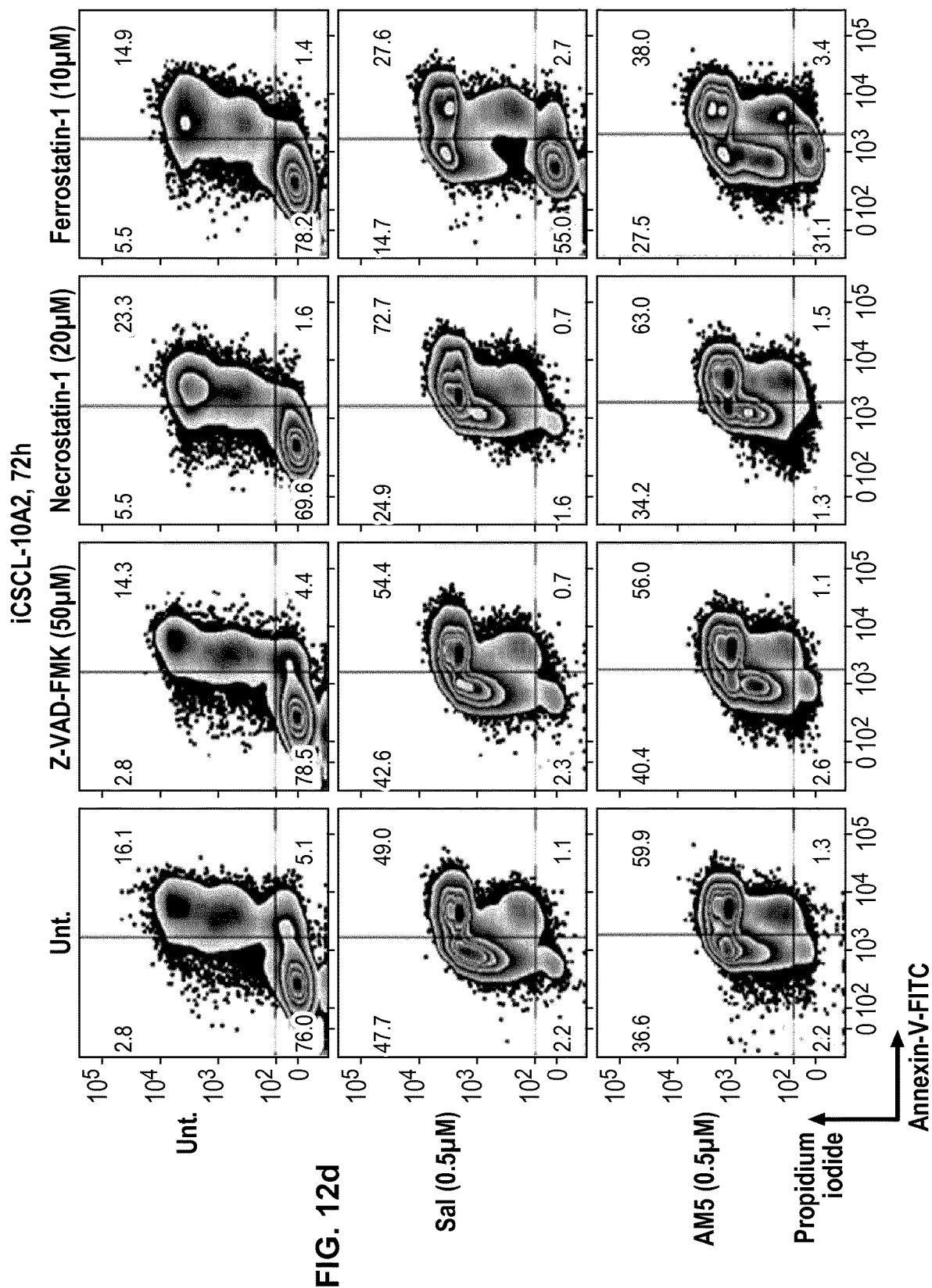
Figure 12E:
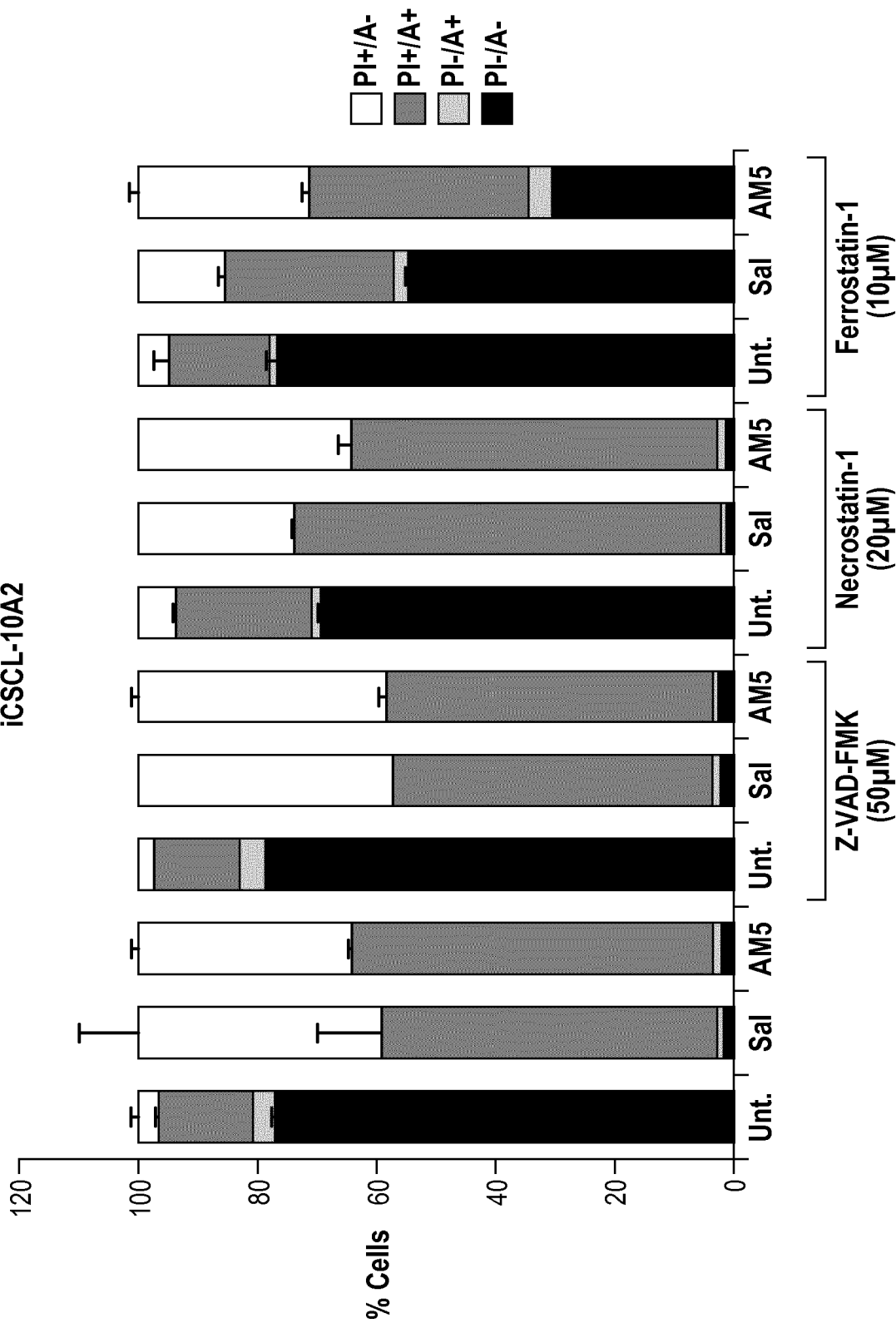
Figure 12F:
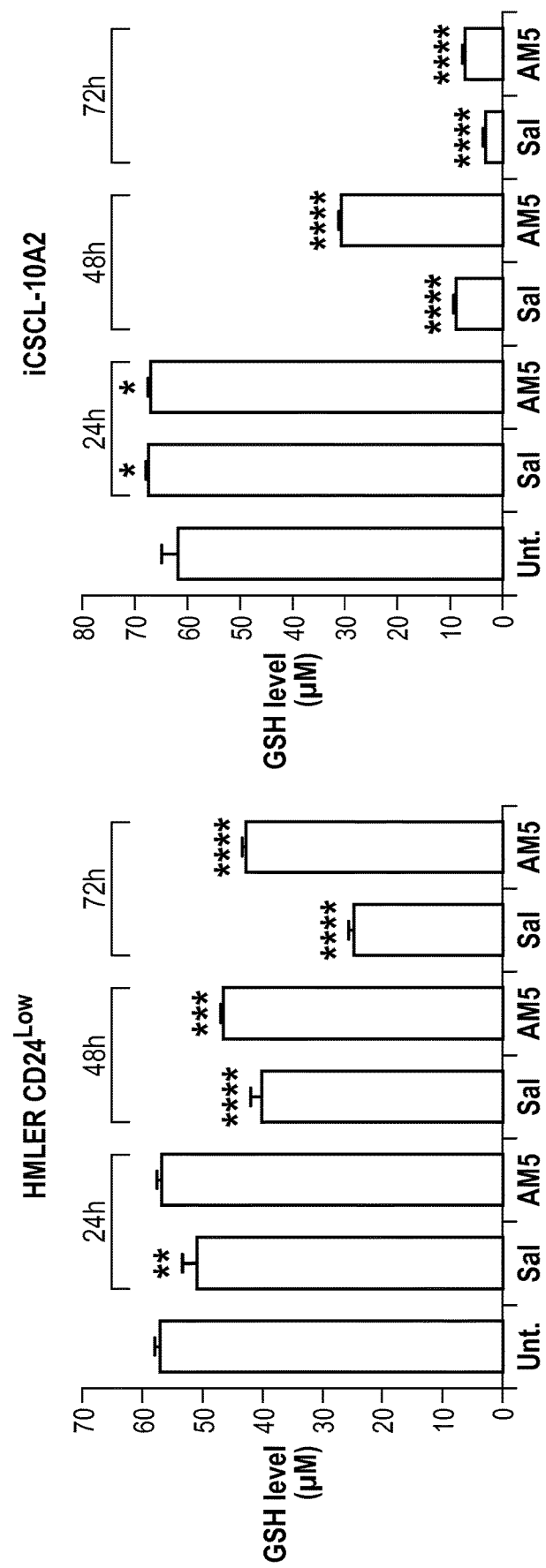

The implication of iron and ROS in the phenotype induced by Sal and AM5 hinted towards the activation of a regulated form of necrotic cell death, termed ferroptosis, detected in HMLER CD24$^{low}$ and iCSCL-10A2 cells after 72 h treatment (FIGS. 12b and c). In support of this, Bodipy-C11 staining indicated the presence of lipid peroxidation in HMLER CD24$^{low}$ and iCSCL-10A2 cells treated with Sal or AM5 (FIG. 12a). In addition, cell death induced by Sal or AM5 could be partially prevented by the ferroptosis inhibitor ferrostatin-1, whereas the apoptosis and necrosis inhibitors Z-VAD-FMK and necrostatin-1, respectively, had no effect on the cell death profiles (FIGS. 12d and e). Furthermore, diminution of endogenous levels of the ROS scavenger glutathione (GSH), a hallmark of ferroptosis, could be detected in HMLER CD24$^{low}$ and iCSCL-10A2 cells treated with Sal or AM5 (FIG. 12f).

Figure 2A:
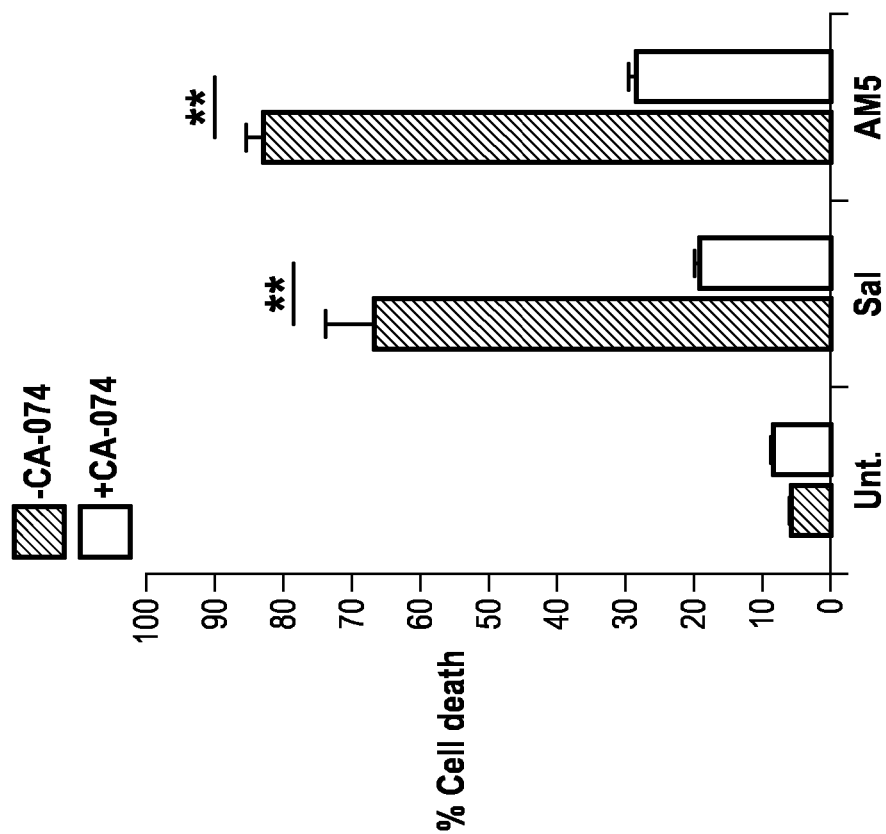
Figure 2B:
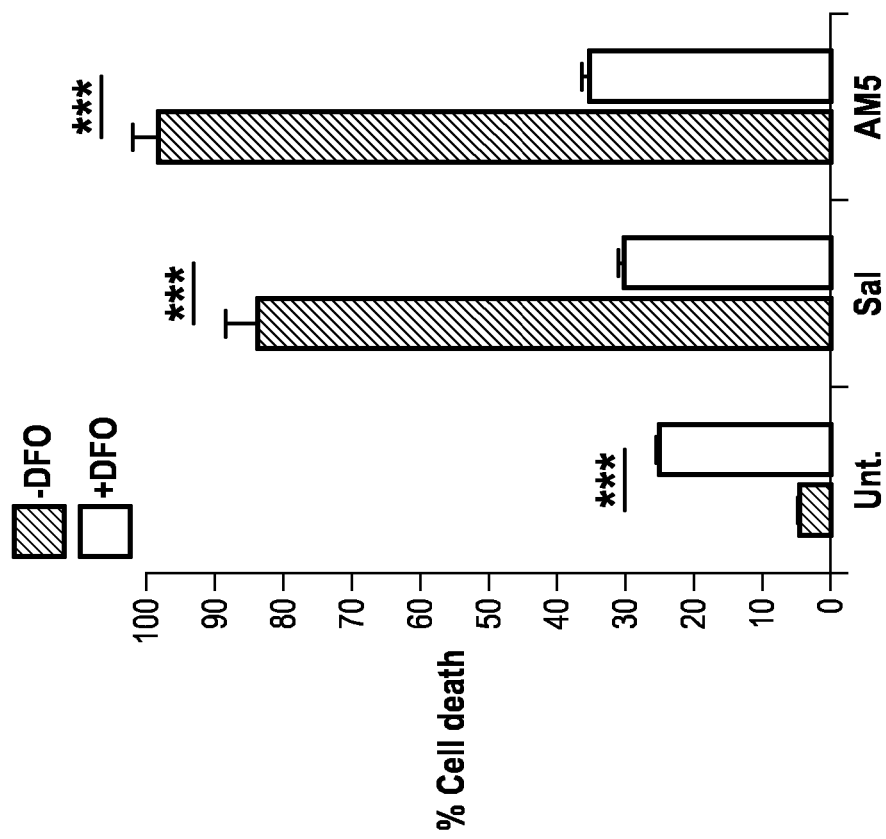
Figure 2C:
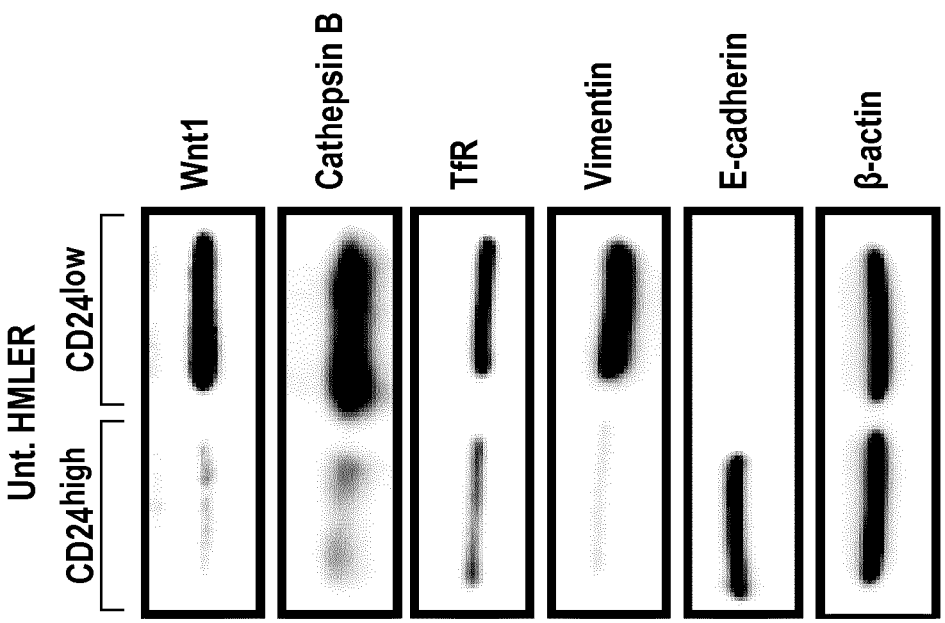
Figure 2D:
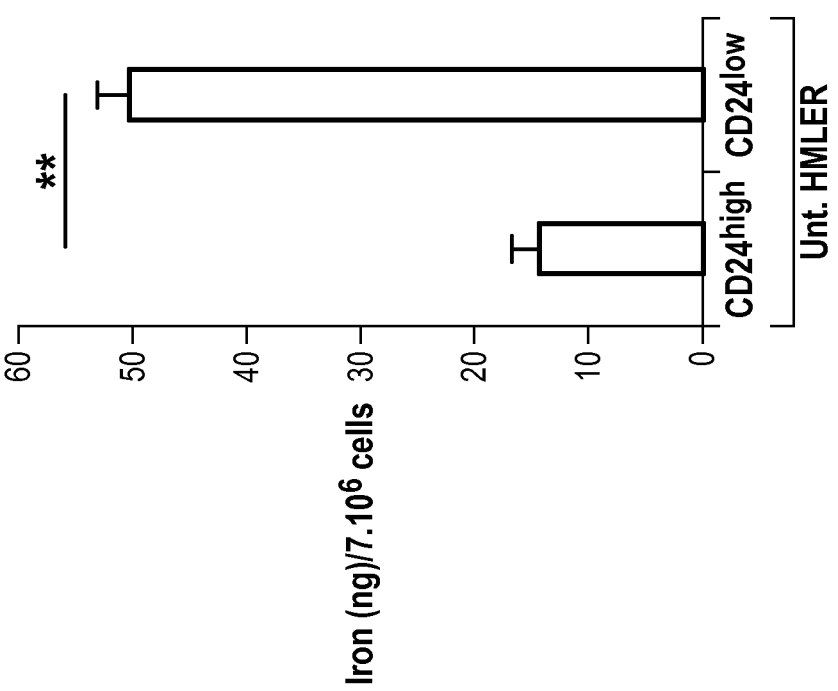

Sal and AM5 also induced a permeabilization of the lysosomal membrane of HMLER CD24$^{low}$ cells as observed from the release of bulky lysosomal dextran into the cytosol (data not shown). Co-treatment with the ROS scavenger N-acetyl-L-cysteine (NAC) partly prevented Sal and AM5 from killing these cells (data not shown), and DFO reduced ROS levels in treated cells (data not shown), exhibiting a protective effect against Sal and AM5 (FIG. 2a). Finally, cathepsin B inhibition decreased the ability of AM5 to induce the production of ROS (data not shown) and rescued cell viability (FIG. 2b). These data indicated that the accumulation of iron in lysosomes promoted by Sal and AM5 led to the production of lysosomal ROS followed by lysosomal dysfunction and cells death. Strikingly, HMLER CD24$^{low}$ cells contained significantly higher levels of iron, iron-uptake protein TfR and active cathepsin B compared to control cells (FIGS. 2c and 2d). These findings underlie the selective effect of Sal on HMLER CD24$^{low}$ cells and raise a putative role of iron in the maintenance of CSCs.

Wnt1 protein level was higher in HMLER CD24$^{low}$ compared to control cells pointing towards iron as a potential driver of CSCs (FIG. 2d).

Example 3: Sal and Sal Analogs Alter CSC Maintenance in the In Vivo PDX Model

AM5 selectively targeted the ALDH+ subpopulation of another model of CSCs, namely iCSCL-10A2 cells, more effectively than Sal (FIG. 13), and exhibited little toxicity against primary breast cells (data not shown). These data illustrate the general susceptibility of AM5 to selectively target CSCs. Sal and AM5 were further shown to reduce tumor growth in two early passage patient-derived xenografts (PDXs), where the clinically approved drug docetaxel (Doc) was less effective (data not shown). This effect was associated with a reduced ratio of ALDH+ cells (FIG. 14), and a decreased tumor-seeding capacity of tumor cells treated in vivo without detectable toxicity at effective doses, with AM5 being more potent than both Sal and Doc (FIG. 15). In particular, treatment with Doc alone shows a lower response than treatment with either AM5 or AM5+Doc. These data further provide solid evidence that Sal analogs, such as AM5, selectively target CSCs in vivo.

Example 4: Effect of AM5, Taxol and Combination Thereof on the Proliferation of HMLER Cd24-Cells AM5, Taxol and a combination of AM5 and Taxol were also assessed for their capability to inhibit cell proliferation and formation of mammospheres (FIG. 16). The combination of AM5 at 15 nM and Taxol at 5 nM inhibits cell proliferation and mammosphere formation with an improved efficacy as compared to AM5 alone at either 15 nM or 5 nM.

Example 5: Iron Concentration in Various Breast Cells Lines and Tumorsphere Formation Table 1 below represents the measurement of iron in a wide range of cell lines. Iron concentration is measured as in Example 2.

TABLE 1

| Tumor cell Subtype | Cell model | Iron Total Iron per 3 × 10$^6$ cells (ng) | Total Iron per cell (pg) | Sphere | Sensibility to AM5 |
|---|---|---|---|---|---|
| Non-tumoral | HBL100 | 114 | 0.04 | + | First |
| Immortalized | HMLE W2 | 99 | 0.03 | +++ | |
| h Tert + T and t SV40 + ras | HMLER CD24$^{low}$ | 290 | 0.10 | +++ | |
| h Tert + T and t de SV40 + ras + sh ECAD | HMLER shECAD | 150 | 0.05 | ++ | |
| h Tert+T and t SV40 + ras + sh gfp | HMLER shGFP | 115 | 0.04 | ++ | |
| CSTN | BT549 | 116 | 0.04 | ++ | Resistant |
|  | MDA-MB-361 | 120 | 0.04 | +++ | Second |
| h Tert + T and t SV40 + ras | HMLER CD24$^{high}$ | 69 | 0.02 | ++ | First |
| H+ | MCF-7 | 83 | 0.03 | ++ | First |
|  | MDA-MB-134 | 65 | 0.02 | ++ | Second |
| CSTN | MDA-MD-157 | 79 | 0.03 | +/− | Second |
|  | BT474 | 60 | 0.02 | + | Second |
| H+ | T47D | 97 | 0.03 | ++ | Resistant |
| H+ | Zr75.1 | 57 | 0.02 | +/− | First |
| CSTN | MDA-MB-231 | 34 | 0.01 | − | Second |
| Colon | SW620 | 38 | 0.01 | + | Third |
| Colon | SW480 | 52 | 0.02 | ++ | Third |

| Subtype | Cell model | Iron Total iron per 7 × 10$^6$ cells (ng) | Total iron per cell (pg) |
|---|---|---|---|
| h Tert + T and t SV40 + ras | HMLER CD24$^{low}$ | 553 ± 29 | 0.08 |
| h Tert + T and t SV40 + ras | HMLER CD24$^{high}$ | 143 ± 20 | 0.02 |

TABLE 2

| Name | Essential specificities |
| --- | --- |
| HBL100 | Human mammary epithelial cell line obtained from primary cultures of cells derived from an early lactation sample of human milk (from ATCC). |
| HMLE W2 | Human mammary epithelial cell line infected with a retrovirus carrying hTERT, SV40 (R. A. Weinberg, Whitehead Institute, Massachusetts Institute of Technology, USA) |
| HMLER ID2 | Human mammary epithelial cell line infected with a retrovirus carrying hTERT, SV40 and the oncogenic allele HrasV12 (R. A. Weinberg, Whitehead Institute, Massachusetts Institute of Technology, USA) |
| HMLER CD24$^{low}$ | HMLER CD44$^{high}$/CD24$^{low}$ not expressing E-cadherin and expressing Vimentin (was obtained from A. Puisieux INSERM) |
| HMLER shGFP (ctrl) | HMLER cells expressing a control shRNA (shCtrl). Generated by infection with retrovirus encoding the pWZL-GFP plasmid. (R. A. Weinberg, Whitehead Institute, Massachusetts Institute of Technology, USA) |
| HMLER shECAD | Transformed HMLER breast cancer cells displaying a short hairpin RNA (shRNA)-mediated inhibition of the human CDH1 gene, which encodes E-cadherin. Generated by infection with retrovirus encoding the pWZL-GFP plasmid. (R. A. Weinberg, Whitehead Institute, Massachusetts Institute of Technology, USA) |
| MCF-7 | Human ductal breast epithelial tumor cell line classified in Estrogen/Progesterone Receptor (ER/PR) positive group and luminal A (from ATCC). |
| Zr75.1 | Human ductal breast epithelial tumor cell line, classified in Estrogen/Progesterone Receptor (ER/PR) and HER-2 positive group and luminal A (from ATCC). |
| MDA-MB-361 | Human ductal breast epithelial tumor cell line, classified in Progesterone Receptor (PR) and HER-2 positive group and luminal B (from ATCC). These cells were isolated from a metastatic site in the brain. |
| MDA-MB-134 | Human ductal breast epithelial tumor cell line classified in Estrogen/Progesterone Receptor (ER/PR) positive group and luminal B (from ATCC). |
| MDA-MD-157 | Human ductal breast epithelial tumor cell line, classified in Estrogen/Progesterone Receptor (ER/PR) and HER-2 negative group and Basal (from ATCC). |
| MDA-MB-231 | Human ductal breast epithelial tumor cell line, classified in Estrogen/Progesterone Receptor (ER/PR) and HER-2 negative group and Basal (from ATCC). |
| BT474 | Human ductal breast epithelial tumor cell line, classified in Progesterone Receptor (PR) and HER-2 positive group and luminal B (from ATCC). |
| Hs578T | Human ductal breast epithelial tumor cell line, classified in Estrogen/Progesterone Receptor (ER/PR) and HER-2 negative group and Basal (from ATCC). |
| BT20 | Human ductal breast epithelial tumor cell line, classified in Estrogen/Progesterone Receptor (ER/PR) and HER-2 negative group and Basal (from ATCC). |
| SW620 | Colon tumor cells; derived from metastatic site: lymph node (from ATCC). |
| SW480 | Colon tumor cells; derived from a primary adenocarcinoma of the colon (from ATCC). |
| BT549 | Human ductal breast epithelial tumor cell line, classified in Estrogen/Progesterone Receptor (ER/PR) and HER-2 negative group and Basal (from ATCC). |
| T47D | Human ductal breast epithelial tumor cell line classified in Estrogen/Progesterone Receptor (ER/PR) positive group and luminal A (from ATCC). |

These results highlight the link between the concentration of iron and tumorsphere formation.

Example 6: Iron Homeostasis would be a Driver of Cancer Stem Cell Phenotype

1. Wnt1 protein level was higher in HMLER CD24$^{low}$ compared to control cells (FIG. 2d).
2. E-cadherin (E-cad) is essential to maintenance of epithelial layers. E-cad expression is a marker of EMT. E-cad protein level was higher in W1, W2 and HMLER ID2 compared to HMLER stem-like CD24$^{low}$ cells (FIG. 5). In contrast, ferritin protein level was higher in HMLER stem-like CD24$^{low}$ cells compared to parental isogenic cells (W1, W2 and HMLER ID2). The loss of E-cadherin and gain of ferritin may be associated with cancer stem cell phenotype.
3. The connection between epithelial-mesenchymal (E-M) plasticity and CSC properties has been paradigm-shifting, linking tumor cell invasion and metastasis with therapeutic recurrence. Cytokines top the list of tumor-associated secreted factors, and are likely to have important effects on the pathways that govern CSC and E-M plasticity. In addition to TGFβ, additional cytokines and growth factors including Oncostatin M (OSM) have also been implicated in inducing EMT (FIG. 6) and by extension, CSC properties. The ability of these cytokines and growth factors to induce CSC properties concomitant with EMT may explain why their presence in the TME correlates with poor patient outcomes.

To investigate whether iron homeostasis play a role in inducing CSC properties concomitant with EMT, the Inventors performed OSM treatment to promote EMT in breast cancer MCF-7 cells. EMT induction was examined by both the increase of two EMT markers Fibronectin and Snail, and the decrease of E-cad protein levels (FIG. 7 left). It could be observed that OSM also induces an increase in ferritin protein level in MCF7 cells (FIG. 7 right). The knock-down of Ferritin expression by RNAi slows down the OSM-induced increase of fibronectin protein level. These data indicate that ferritin expression is associated with EMT.

Figure 8A:
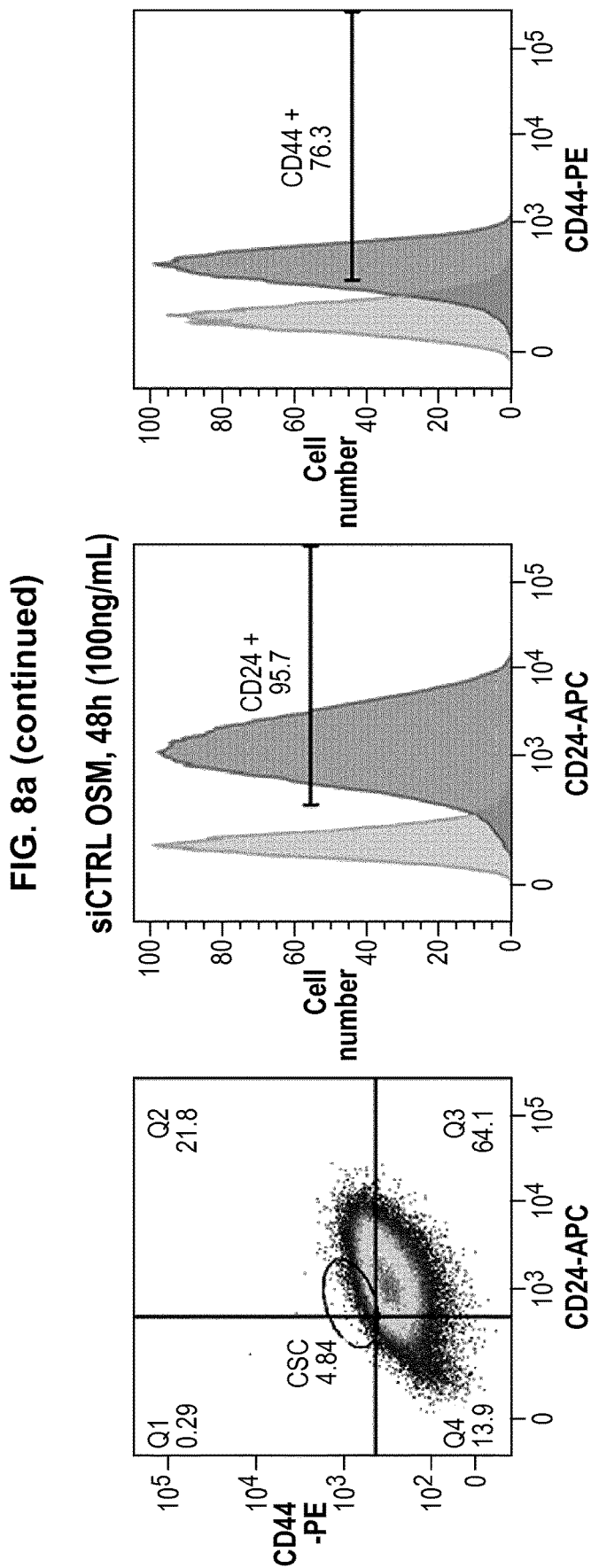
Figure 8A:
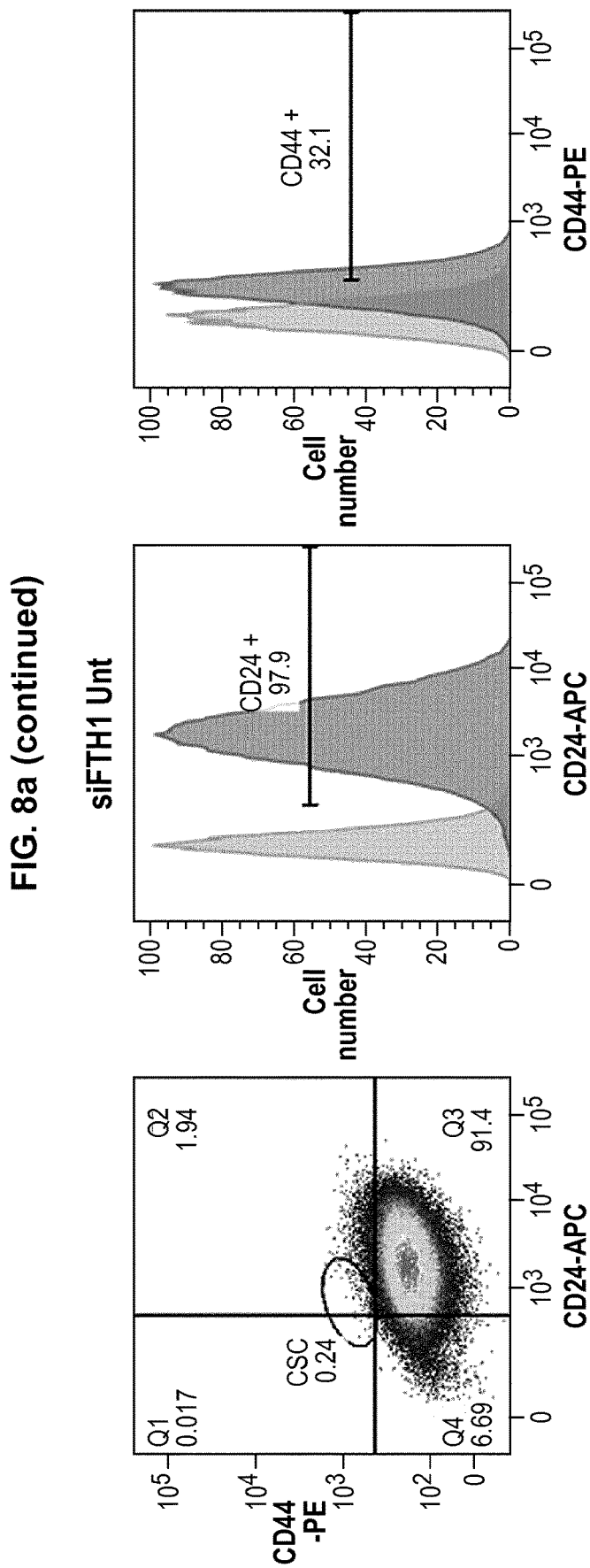
Figure 8A:
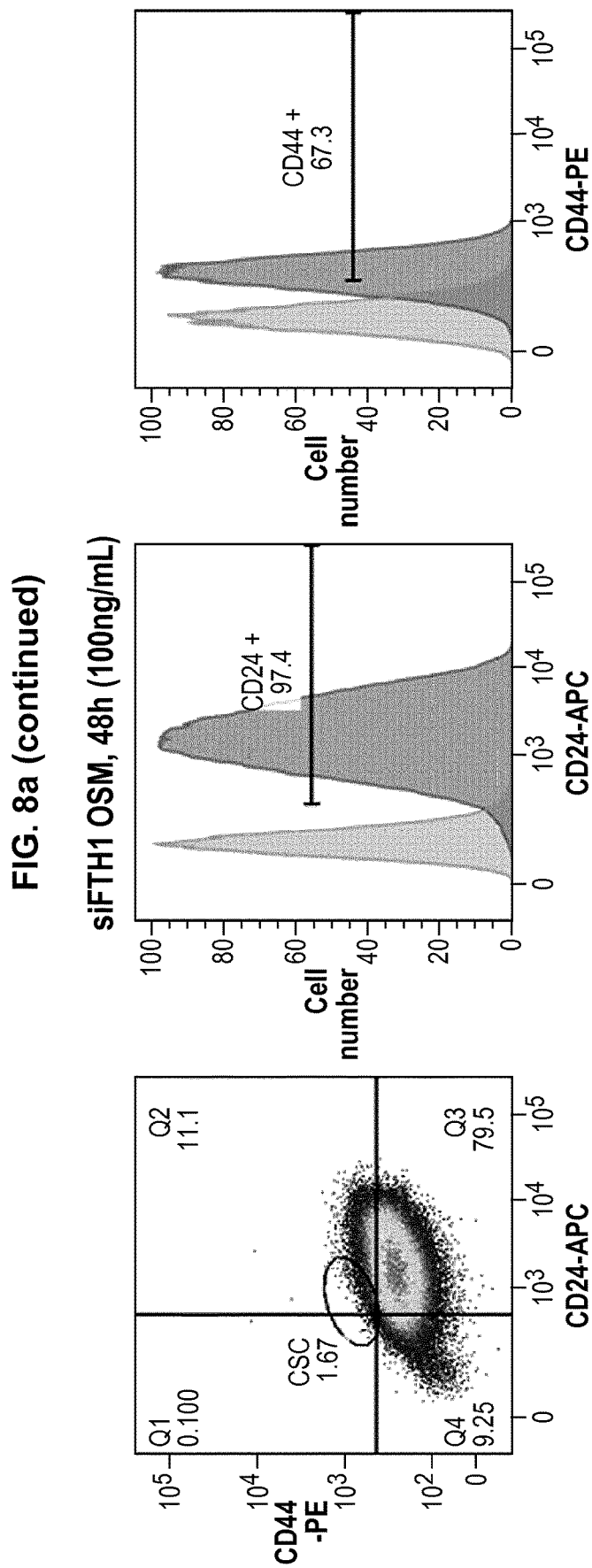
Figure 8B:
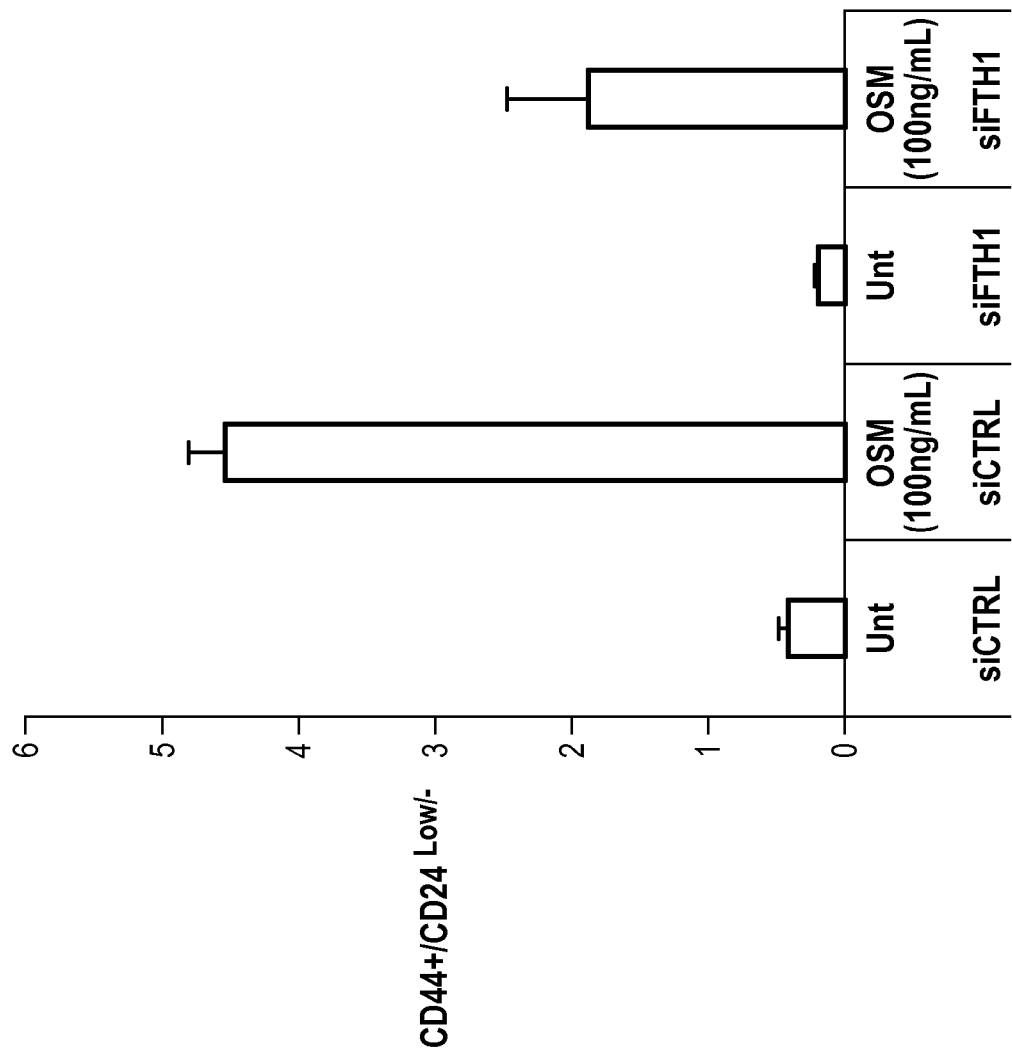
Figure 8C:
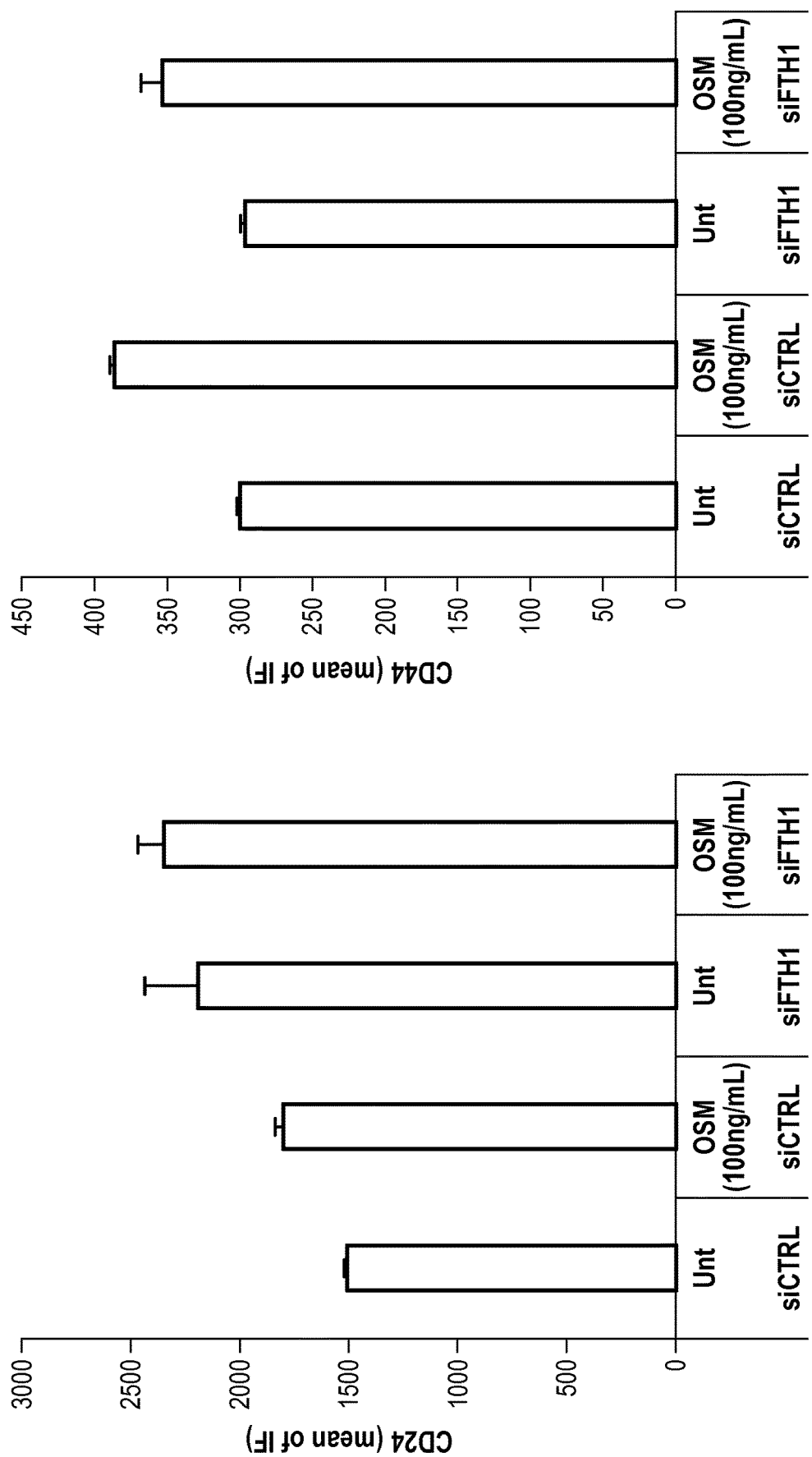

4. The Inventors next performed OSM treatment to increase the CD44$^{high}$CD24$^{Low/-}$ cancer stem cell (CSC) population in breast cancer MCF7 cells (FIGS. 8a & 8b: % of CSC shift from 0.42% to 4.84%). Whereas the % of CD44$^{high}$ population increases from 33% to 76%, the % of CD24$^{high}$ population remains unchanged (FIG. 8a). Similar to these data, it was observed that the mean fluorescence intensity (IF) increases for CD44 in the OSM treated cells but not for the CD24 population. Knock down of Ferritin expression by RNAi alone slightly increases the IF of the CD24 population, but not for the CD44 population (FIG. 8a). Interestingly, it was observed that the Knock down of Ferritin expression interferes with the OSM-mediated induction of CD44$^{high}$CD24$^{Low/-}$ in MCF-7 cells (FIGS. 8a and 8b). Furthermore, knocking down ferritin impaired the ability of cytokine oncostatin M (OSM) to induce a stem-like phenotype as defined by the percentage of ALDH+cells (FIG. 8d), indicating that CSC generation in inhibited.
5. To investigate functional difference between non-CSCs and CSCs, we first examined the effect of Sal and AM5 treatment on matched isogenic non-CSCs (HMLER CD24$^{high}$) cells, CSCs (HMLER CD24$^{low}$) cells and a new CSC model available in the laboratory. In HMLER CD24$^{low}$ (see FIG. 1f) and iCSCA2 cells, Sal and AM5 induced a response characteristic of a cytosolic depletion of iron, including increased levels of iron-responsive element-binding protein 2 (IRP2) and transferrin receptor (TfR) along with reduced levels of ferritin (FIG. 1f and FIG. 9). Although Sal and AM5 reduced the level of ferritin in non-CSC (HMLER $CD24^{high}$ ID2) cells, we did not observe a response characteristic of a cytosolic depletion of iron, including increased levels of IRP2 and TfR.

6. The Inventors next examined the transferrin uptake difference between non-CSC and CSC. To do this, HMLER $CD44^{high}CD24^{Low}$ cells and their counterpart (HMLER $CD44^{Low/-}$ $CD24^{high}$ ID2) are co-cultured and transferrin uptake assessed. HMLER $CD44^{high}$ $CD24^{Low}$ stem like cells were identified by CD44 expression to discriminate ID2 cells.

Figure 10A:
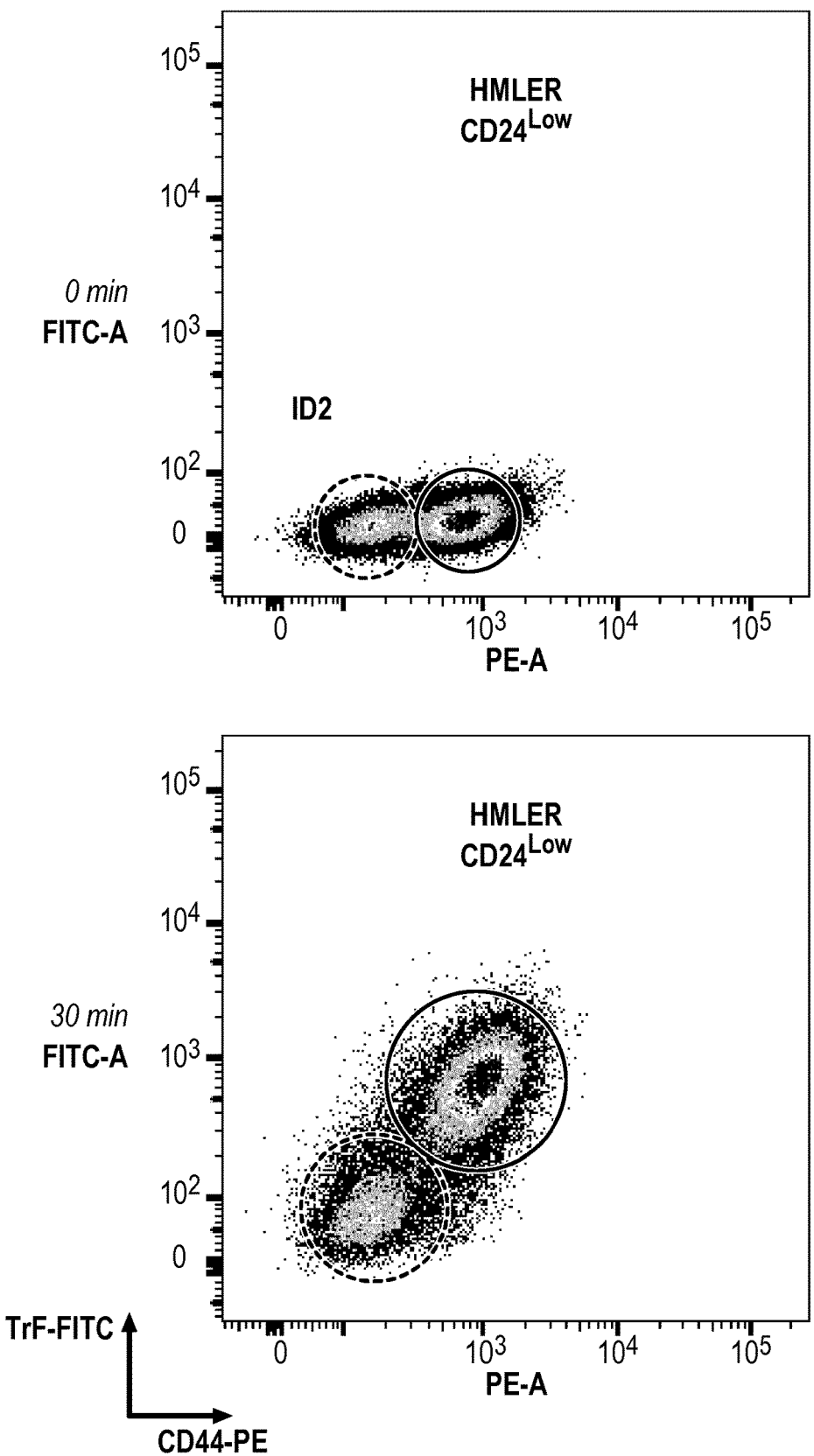
Figure 10A:
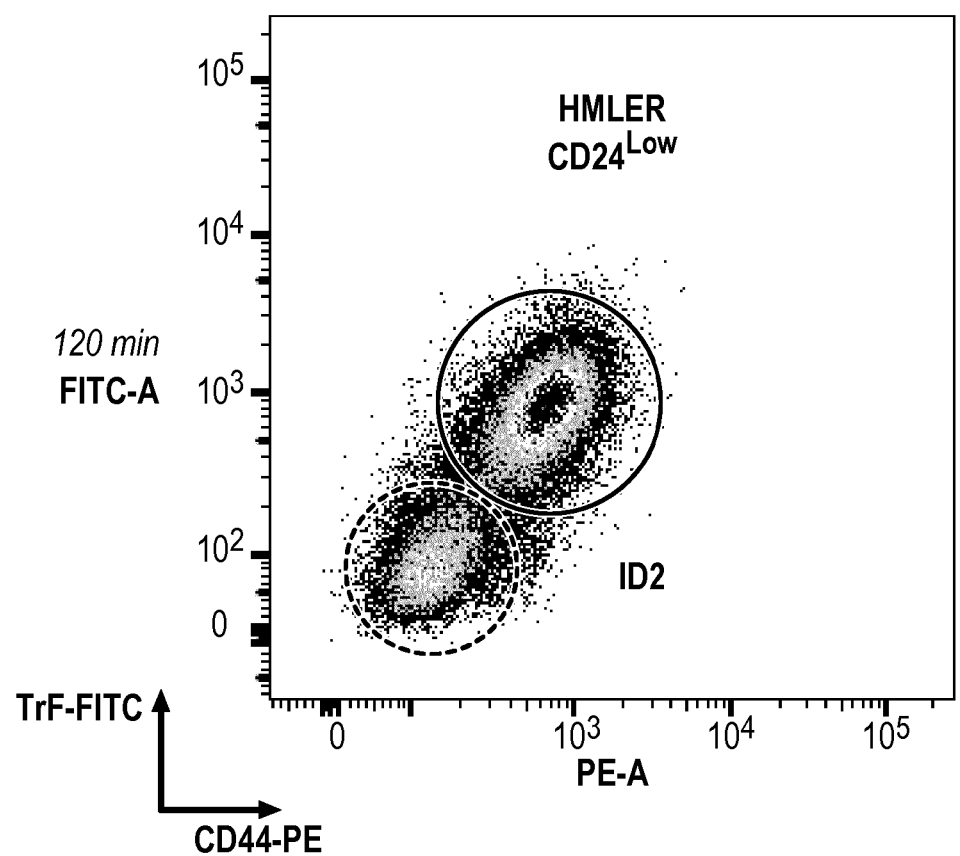
Figure 10B:
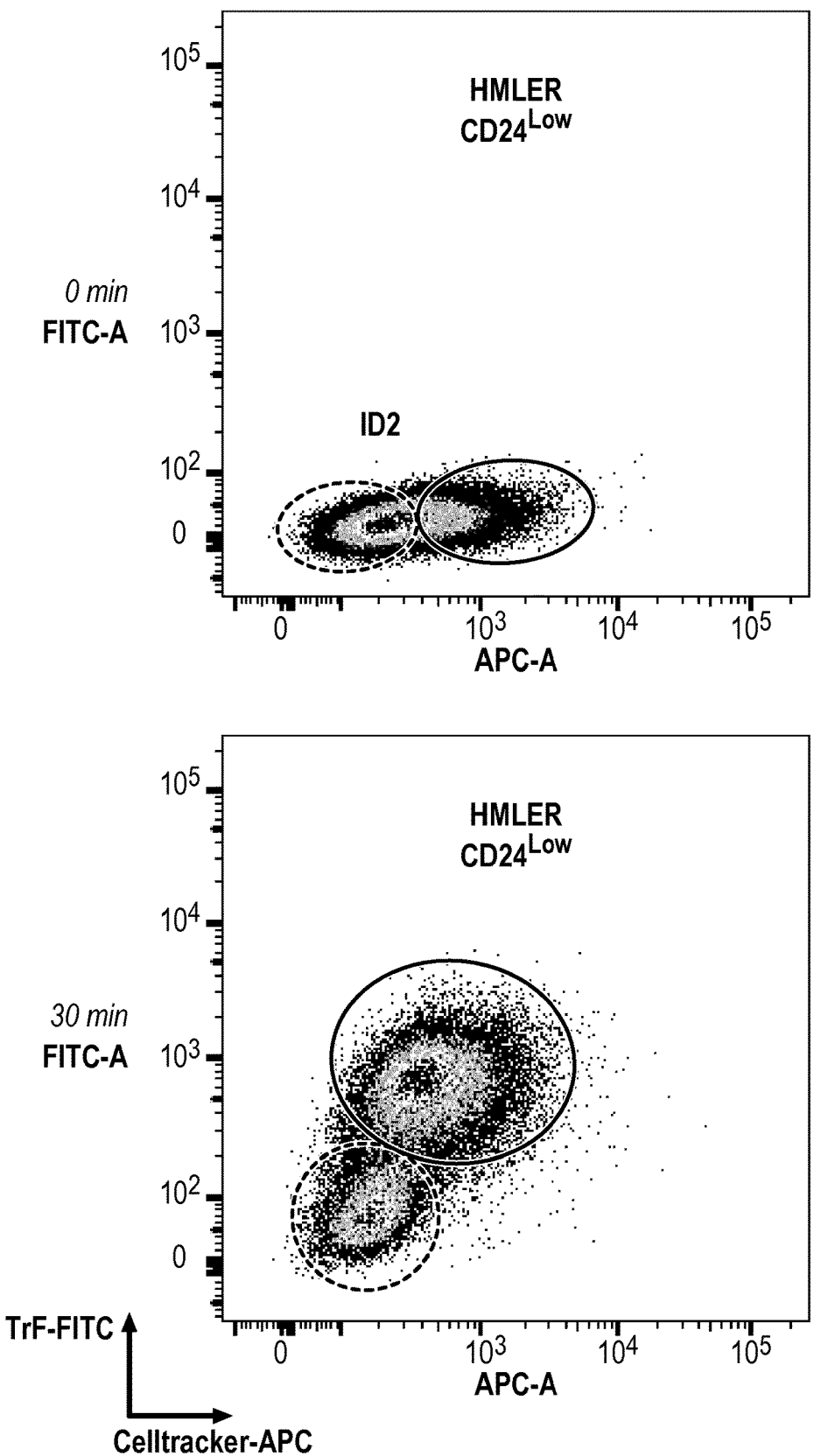
Figure 10B:
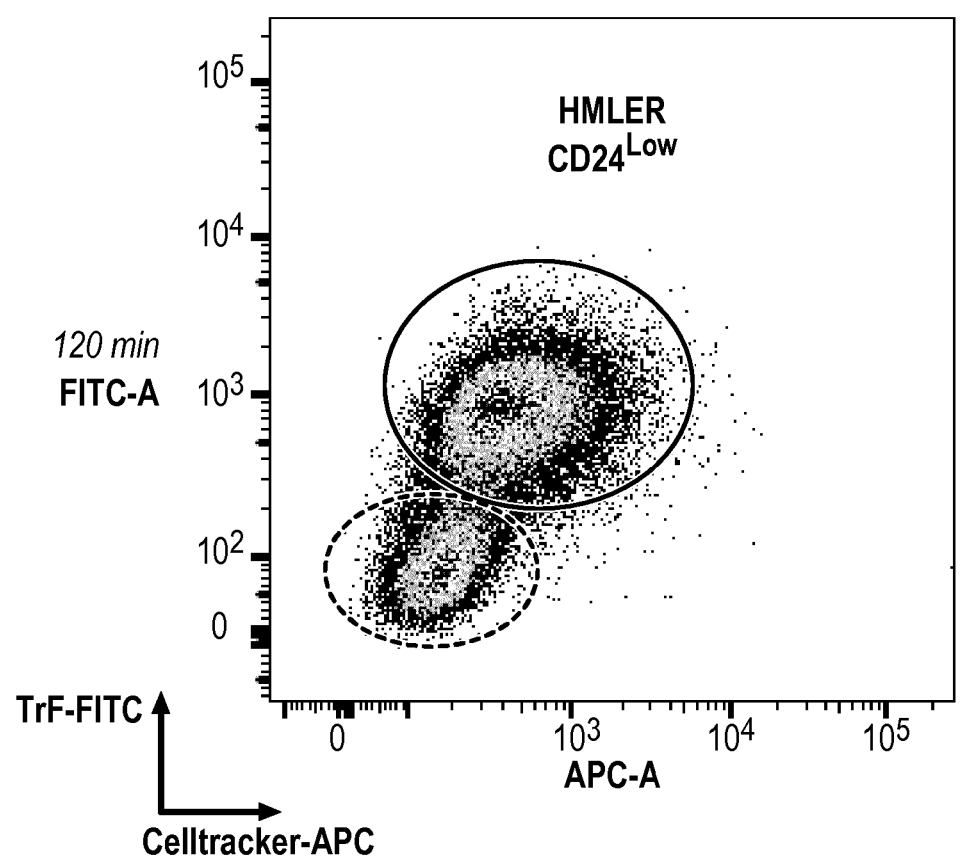
Figure 10C:
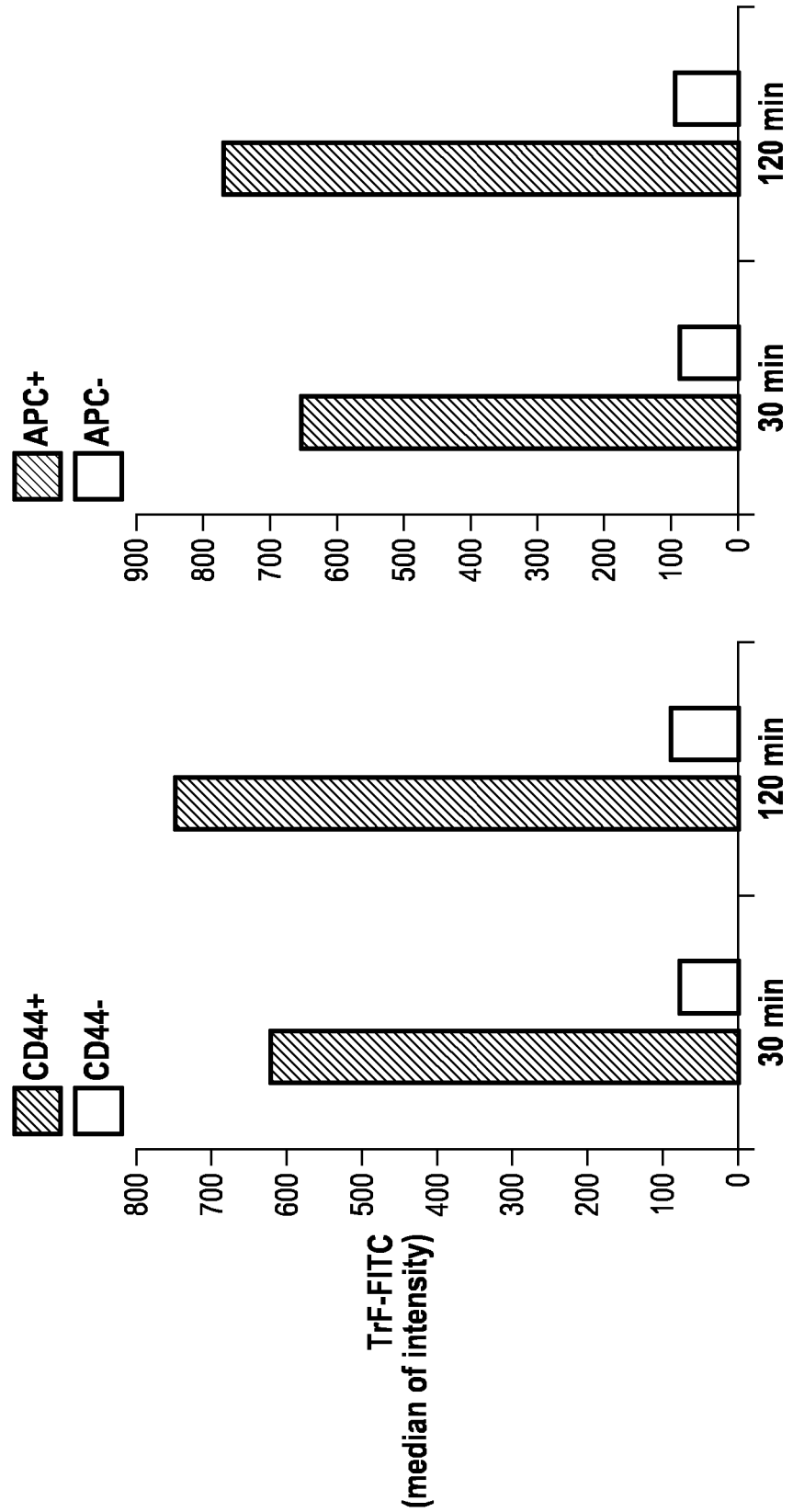

Interestingly, $CD44^{high}$ cells uptake transferrin more than $CD44^{Low}$ (FIGS. 10a and c left). They next used cell tracker method staining to discriminate HMLER $CD44^{high}$ $CD24^{Low}$ stem-like cells from ID2 cells (FIGS. 10a and c left). APC positive cells uptake transferrin more than APC negative cells. These data indicate that HMLER $CD44^{high}$ $CD24^{Low}$ stem-like cells uptake transferrin more than their isogenic HMLER ID2 counterpart.

7. The Inventors then investigated the effect of transferrin to induce CSC properties. It could be demonstrated that TGF-31 increases the percent of $CD44^{high}/CD24^{Low/-}$ population (8% VS 21%). Transferrin uptake potentiates the TGF-beta-mediated induction of $CD44^{high}CD24^{Low/-}$ in HMLER cells. These data indicate that iron homeostasis would be a driver of cancer stem cell phenotype.

8. The Inventors finally investigated the specific targeting of CSCs. It was shown that AM5 selectively targets ALDH+ CSCs, leading to a decreased ratio of ALDH+ cells and a decreased tumor-seeding capacity (FIG. 13-15). Of note, AM5+ Doc treatment generates a higher response than treatment with Doc alone. Similarly, AM5+ Taxol generates a higher response than treatment with Taxol alone, as determined according to number and size of in vitro mammosphere formation (FIG. 16).

REFERENCES

Perou et al. 2000, Molecular portraits of human breast tumours, Nature 406, 747-752.
Gusterson et al. 2005, Immunohistochemistry: Basics and Methods, Cancer treatment: the combination of vaccination with other therapies.
Andersen et al. 2008, Cancer Immunology Immunotherapy, 57(11): 1735-1743.
Horan P K et al, Fluorescent cell labeling for in vivo and in vitro cell tracking Methods Cell Biol. 1990.
Quoix et al. 2011, Therapeutic vaccination with TG4010 and first-line chemotherapy in advanced non-small-cell lung cancer: a controlled phase 2B trial., Lancet Oncol. 12(12): 1125-33.
Liseth et al. 2010, Combination of intensive chemotherapy and anticancer vaccines in the treatment of human malignancies: the hematological experience.
Hirooka et al. 2009, A combination therapy of gemcitabine with immunotherapy for patients with inoperable locally advanced pancreatic cancer, Pancreas 38(3): e69-74.
Baskar et al., Cancer and Radiation Therapy: Current Advances and Future Directions, Int. J Med Sci. 9(3): 193-199.
Gupta et al., 2009, Identification of Selective Inhibitors of Cancer Stem Cells by High-Throughput Screening, Cell, vol. 138, p. 645-659.
Charafe-Jauffret et al., 2013, ALDH1-positive cancer stem cells predict engraftment of primary breast tumors and are governed by a common stem cell program. Cancer Res. 73, 7290-7300.
Naujokat and Steinhart, 2012, Salinomycin as a drug for targeting human cancer stem cells. J. Biomed. Biotechnol. DOI: 10.1155/2012/950658.
Miller et al., 2011, An Iron Regulatory Gene Signature Predicts Outcome in Breast Cancer, Cancer Res. 71(21): 6728-6737.

The invention claimed is:
1. A method for selectively killing CSCs in a mammal, comprising administering to said mammal an iron-chelating pharmaceutical composition, comprising at least one component selected from 20-alkyl-amino derivatives of salinomycin of formula (I')

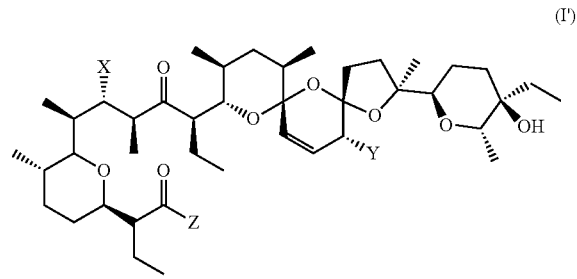

wherein:
X is selected from the group consisting of OH and =O,
Y is selected from the group consisting of —$NR_1R_2$; —$NR_3$—$(CH_2)_n$—$NR_4R_5$; —O—$(CH_2)_n$—$NR_4R_5$; —$NR_3$—$(CH_2)_n$—$N^+R_6R_7R_8$; and —O—$(CH_2)_n$—$N^+R_6R_7R_8$; and
$R_1$ and $R_2$, identical or different, are selected from the group consisting of H; ($C_1$-$C_{16}$)-alkyl; ($C_3$-$C_{16}$)-alkenyl; ($C_3$-$C_{16}$)-alkynyl; aryl; heteroaryl; ($C_1$-$C_6$)-alkyl-aryl; ($C_1$-$C_6$)-alkyl-heteroaryl; or $R_1$ represents H and $R_2$ represents $OR_9$, where $R_9$ is H, ($C_1$-$C_6$)-alkyl, aryl and ($C_1$-$C_6$)-alkyl-aryl;
$R_3$ is selected from the group consisting of H; ($C_1$-$C_6$)-alkyl; ($C_1$-$C_6$)-alkyl-aryl;
$R_4$ and $R_5$, identical or different, are selected from the group consisting of H; ($C_1$-$C_6$)-alkyl; aryl; ($C_1$-$C_6$)-alkyl-aryl;
$R_6$, $R_7$ and $R_8$, identical or different, are selected from the group consisting of ($C_1$-$C_6$)-alkyl; aryl; ($C_1$-$C_6$)-alkyl-aryl;
n=2, 3, 4, 5 or 6,
Z is a functional group capable of chelating iron salts such as OH: $NHNR_9R_{10}$ (hydrazine), $NHOC(O)R_{11}$ (O-Acyl hydroxylamine), N(OH)—C(O)$R_{11}$ (N-acyl hydroxylamine), OOH, $SR_{12}$; 2-aminopyridine; 3-aminopyridine; —$NR_3$—$(CH_2)_n$—$NR_4R_5$; —$NR_3$—$(CH_2)_n$—OH; where:
$R_9$ and $R_{10}$, identical or different, are selected from the group consisting of H, ($C_1$-$C_6$)-alkyl, aryl and ($C_1$-$C_6$)-alkyl-aryl;

$R_{11}$ is selected from the group consisting of H; ($C_1$-$C_{16}$)-alkyl; ($C_3$-$C_{16}$)-alkenyl; ($C_3$-$C_{16}$)-alkynyl; aryl; heteroaryl; ($C_1$-$C_6$)-alkyl-aryl; ($C_1$-$C_6$)-alkyl-heteroaryl;

$R_{12}$ is selected from the group consisting of H; ($C_1$-$C_{16}$)-alkyl; ($C_3$-$C_{16}$)-alkenyl; ($C_3$-$C_{16}$)-alkynyl; aryl; heteroaryl; ($C_1$-$C_6$)-alkyl-aryl; ($C_1$-$C_6$)-alkyl-heteroaryl, n=0, 2, 3 or 4, AM5, AM23, AM23S, and combinations thereof.

2. The method of claim 1, wherein said iron-chelating pharmaceutical composition binds total cellular iron under the form of ferrous ($Fe^{2+}$) and ferric ($Fe^{3+}$) iron in said mammal, thereby inducing ferritinophagy and reactive oxygen species (ROS) production responsible for specific and/or selective CSC death in said mammal.

3. The method of claim 1, wherein said iron-chelating pharmaceutical composition binds total cellular iron under the form of ferrous ($Fe^{2+}$) and ferric ($Fe^{3+}$) iron in said mammal while preventing drug-resistance in said mammal by selectively targeting CSCs.

4. The method of claim 1, wherein said iron-chelating pharmaceutical composition binds total cellular iron under the form of ferrous ($Fe^{2+}$) and ferric ($Fe^{3+}$) iron in said mammal while preventing drug-resistance in said mammal by selectively targeting CSCs.

5. A method according to claim 1, wherein the mammal having CSCs is selected according to an in vitro method for diagnosing cancer having a high risk of recurrence, a high risk of metastasis, and/or a cancer with resistance to therapy, in a subject, comprising at least:

a) measuring the amount of total cellular iron, preferably under the form of ferrous iron ($Fe^{2+}$), in a biological sample from a subject; and b) comparing said amount measured in step a) to a reference value range for total cellular iron, wherein an amount of total cellular iron as measured in step a) is higher than said reference value range is indicative of the presence of CSCs, thereby indicating that said subject has a cancer.

6. A method according to claim 5, wherein the amount of total cellular iron as measured in step a) of the in vitro method, which is indicative of the presence of CSCs, is superior or equal to 0.05 pg/cell, preferably superior to 0.06 pg/cell, preferably superior to 0.07 pg/cell, preferably superior to 0.08 pg/cell, preferably superior to 0.09 pg/cell, preferably superior to 0.10 pg/cell, preferably superior to 0.11 pg/cell, preferably superior to 0.12 pg/cell, preferably superior to 0.13 pg/cell, preferably superior to 0.14 pg/cell, preferably superior to 0.20 pg/cell, preferably superior to 0.24 pg/cell, more preferably higher than 0.30 pg/cell.

7. A method according to claim 1, wherein said composition is co-administered with radiation therapy or chemotherapy.

8. A method according to claim 1, for selectively killing breast CSCs in a mammal.

* * * * *